US011464856B2

(12) United States Patent
Wischhusen et al.

(10) Patent No.: US 11,464,856 B2
(45) Date of Patent: *Oct. 11, 2022

(54) COMBINATION THERAPY USING INHIBITORS OF HUMAN GROWTH AND DIFFERENTIATION FACTOR 15 (GDF-15) AND IMMUNE CHECKPOINT BLOCKERS

(71) Applicant: JULIUS-MAXIMILIANS-UNIVERSITÄT WÜRZBURG, Würzburg (DE)

(72) Inventors: Jörg Wischhusen, Würzburg (DE); Markus Haake, Estenfeld (DE); Reinhard Dummer, Zürich (CH); Matthias Mehling, Basel (CH); Tina Schäfer, Würzburg (DE); Martina Selle, Würzburg (DE)

(73) Assignee: JULIUS-MAXIMILIANS-UNIVERSITÄT Würzburg, Würzburg (DE)

( * ) Notice: Subject to any disclaimer, the term of this patent is extended or adjusted under 35 U.S.C. 154(b) by 736 days.

This patent is subject to a terminal disclaimer.

(21) Appl. No.: 15/765,176

(22) PCT Filed: Sep. 30, 2016

(86) PCT No.: PCT/EP2016/073520
§ 371 (c)(1),
(2) Date: Mar. 30, 2018

(87) PCT Pub. No.: WO2017/055613
PCT Pub. Date: Apr. 6, 2017

(65) Prior Publication Data
US 2019/0160169 A1 May 30, 2019

(30) Foreign Application Priority Data

Oct. 2, 2015 (GB) .................... 1517531
Apr. 29, 2016 (GB) .................... 1607801

(51) Int. Cl.
*A61K 39/395* (2006.01)
*C07K 16/22* (2006.01)
*C07K 16/28* (2006.01)
*G01N 33/574* (2006.01)
*G01N 33/50* (2006.01)
*A61K 45/06* (2006.01)
*A61P 35/00* (2006.01)
*A61K 31/7105* (2006.01)
*A61K 31/713* (2006.01)
*A61K 39/00* (2006.01)

(52) U.S. Cl.
CPC ........ *A61K 39/3955* (2013.01); *A61K 31/713* (2013.01); *A61K 31/7105* (2013.01); *A61K 45/06* (2013.01); *A61P 35/00* (2018.01); *C07K 16/22* (2013.01); *C07K 16/2818* (2013.01); *C07K 16/2878* (2013.01); *G01N 33/505* (2013.01); *G01N 33/5064* (2013.01); *G01N 33/574* (2013.01); *A61K 2039/505* (2013.01); *A61K 2039/507* (2013.01); *A61K 2039/55* (2013.01); *C07K 2317/34* (2013.01); *C07K 2317/76* (2013.01); *G01N 2500/10* (2013.01)

(58) Field of Classification Search
None
See application file for complete search history.

(56) References Cited

U.S. PATENT DOCUMENTS

| 8,003,099 B2 | 8/2011 | Auer et al. |
| 2006/0148709 A1 | 7/2006 | Unsicker et al. |
| 2007/0128636 A1 | 6/2007 | Baker et al. |
| 2010/0278843 A1 | 11/2010 | Breit et al. |
| 2011/0262444 A1 | 10/2011 | Kim |
| 2014/0193427 A1 | 7/2014 | Lerner et al. |
| 2014/0271546 A1 | 9/2014 | Warf et al. |
| 2014/0378665 A1 | 12/2014 | Xiong et al. |

FOREIGN PATENT DOCUMENTS

| WO | 2005/099746 A1 | 10/2005 |
| WO | 2009/021293 A1 | 2/2009 |
| WO | 2011/127219 A1 | 10/2011 |
| WO | 2012/162561 A2 | 11/2012 |
| WO | 2013/012648 A1 | 1/2013 |
| WO | 2014/049087 A1 | 4/2014 |
| WO | 2014/100689 A1 | 6/2014 |
| WO | 2015/108907 A2 | 7/2015 |
| WO | 2015/144855 A1 | 10/2015 |
| WO | 2016/049470 A1 | 3/2016 |

OTHER PUBLICATIONS

Darvin et al. (2018) Experimental & Molecular Medicine 30: 165 pp. 1-11.*
Jerby-Arnon et al., "A Cancer Cell Program Promotes T Cell Exclusion and Resistance to Checkpoint Blockade", Cell, vol. 175, pp. 984-997, Nov. 1, 2018, doi: 10.1016/j.cell.2018.09.006.
Long et al., "Epacadostat Plus Pembrolizumab Versus Placebo Plus Pembrolizumab in Patients With Unresectable or Metastatic Melanoma (ECHO-301-KEYNOTE-252): A Phase 3, Randomised, Double-Blind Study", Lancet Oncology, vol. 20, No. 8, pp. 1083-1097, Aug. 2019, doi: 10.1016/S1470-2045(19)30274-8.
Spranger et al., "Tumor-Intrinsic Oncogene Pathways Mediating Immune Avoidance", OncoImmunology, vol. 5, No. 3, e1086862, 2016, doi: 10.1080/2162402X.2015.1086862.
Thompson et al., "Human Anti-CD40 Antibody and Poly IC:LC Adjuvant Combination Induces Potent T Cell Responses in the Lung of Nonhuman Primates", The Journal of Immunology, 2015, 195: 1015-1024.

(Continued)

*Primary Examiner* — Michael D Pak
(74) *Attorney, Agent, or Firm* — Dechert LLP; Andrew T. Wilkins; Victoria E. Pedanou

(57) ABSTRACT

The present invention relates to uses of inhibitors of human Growth and Differentiation Factor 15 (GDF-15), and to combined uses of such inhibitors with immune checkpoint blockers, in the treatment of solid cancers.

18 Claims, 21 Drawing Sheets
Specification includes a Sequence Listing.

(56) References Cited

OTHER PUBLICATIONS

Yoshida et al., "New Immune Checkpoint Inhibitors Human Anti-PD-1 Antibody Nivolumab (Opujibo® intravenous infusion 20 mg, 100 mg) of the Pharmacological Properties and Clinical Efficacy", Japanese Pharmacology Magazine, vol. 146, Issue 2, pp. 106-114, doi: 10.1254/fpj.146.106.
Adkins, C. et al (2015) "A novel preclinical method to quantitatively evaluate early-stage metastatic events at the murine blood-brain barrier," Cancer Prev Res (Phila) 8(1):68-76.
Altschul et al. (1990) "Basic local alignment search tool," Journal of Molecular Biology 215:403-410.
Altschul et al.: (1997) "Gapped BLAST and PSI-BLAST: a new generation of protein database search programs," Nucleic Acids Res. 25:3389-3402.
Angell, H. et al. (2013) "From the immune contexture to the Immunoscore: the role of prognostic and predictive immune markers in cancer," Curr Opin Immunol. (2):261-7.
Arbabi, G. et al. (1997) "Selection and identification of single domain antibody fragments from camel heavy-chain antibodies." FEBS Lett. 414(3):521-6.
Artz, A. et al. (2016) "GDF-15 inhibits integrin activation and mouse neutrophil recruitment through the ALK-5/TGF-βRII heterodimer," Blood. 128(4):529-41.
Bauskin, A. et al. (2005) "The propeptide mediates formation of stromal stores of PROMIC-1: role in determining prostate cancer outcome," Cancer Res. 65(6):2330-6.
Boehm: Nivolumab beim Nierenzellkarzinom in der Zweitlinie—verlängertes Überleben mit Immuntherapie. Medscape. Sep. 28, 2015.
Brown, D. et al. (2009) "Macrophage inhibitory cytokine 1: a new prognostic marker in prostate cancer," Clin Cancer Res. 15(21):6658-64.
Chen, S. et al. (2007) "Prostate-derived factor as a paracrine and autocrine factor for the proliferation of androgen receptor-positive human prostate cancer cells," The Prostate. 67(5):557-71.
Cheng, P. et al. (2015) "Data mining the Cancer Genome Atlas in the era of precision cancer medicine," Swiss Med Wkly. 145:w14183.
Chothia, C. et al. (1987) "Canonical structures for the hypervariable regions of immunoglobulins," J Mol Biol. 196(4):901-17.
Chothia, C. et al. (1989) "Conformations of immunoglobulin hypervariable regions," Nature. 342(6252):877-83.
Clackson, T et al. (1991) "Making antibody fragments using phage display libraries." Nature. 352(6336):624-8.
Cong M.et al. (2015) Advertorial: "Novel Bioassay to Assess PD-1/PD-L1 Therapeutic Antibodies in Development for Immunotherapy Bioluminescent Reporter-Based PD-1/PD-L1 Blockade Bioassay." (http://www.genengnews.com/gen-articles/advertorial-novel-bioassay-to-assess-pd-1-pd-l1-therapeutic-antibodies-in-development-for-immun/5511/).
Corre, J. et al. (2013) "Concise Review: Growth Differentitaion Factor 15 in Pathology: A Clinical Role," Stem Cells Translational Medicine. 2:946-952.
Cully, M. (2015) "Combinations with checkpoint inhibitors at wavefront of cancer immunotherapy," Nat Rev Drug Discov. 14(6):374-5.
Eisenauer et al. (2009) "New response evaluation criteria in solid tumours: revised RECIST guideline (version 1.1)," Eur. J. Cancer. 45(2):228-47.
Gajewski, T. et al. (2013) "Cancer immunotherapy strategies based on overcoming barriers within the tumor microenvironment," Curr Opin Immunol. 25(2):268-76.
Garber, K. (2015) "Predictive biomarkers for checkpoints, first tests approved," Nat Biotechnol. 33(12):1217-1218.
Gentles, A. et al. (2015) "The prognostic landscape of genes and infiltrating immune cells across human cancers," Nat Med. (8):938-945.
Gouttefangeas, C. et al. (2015) "Flow Cytometry in Cancer Immunotherapy: Applications, Quality Assurance and Future," Cancer Immunology: Translational Medicine from Bench to Bedside (N. Rezaei editor). Springer. Chapter 25: pp. 471-486.
Guidicelli, V. et al. (2004) IMGT/V-QUEST, an integrated software program for immunoglobulin and T cell receptor V-J and V-D-J rearrangement analysis. Nucleic Acids Res. 32(Web Server issue):W435-40.
Herbertz, S. et al. (2015) "Clinical development of galunisertib (LY2157299 monohydrate), a small molecule inhibitor of transforming growth factor-beta signaling pathway," Drug Des Devel Ther. 9:4479-99.
Herbst, R. et al. (2014) "Predictive correlates of response to the anti-PD-L1 antibody MPDL3280A in cancer patients," Nature. 515(7528):563-7.
Holliger, P. et al. (1993) "Diabodies: small bivalent and bispecific antibody fragments." Proc Natl Acad Sci U S A. 90(14):6444-8.
Holt, L. et al. (2003) "Domain antibodies: proteins for therapy," Trends Biotechnol. 21(11):484-90.
Huang, C. et al. (2007) "Molecular alterations in prostate carcinomas that associate with in vivo exposure to chemotherapy: identification of a cytoprotective mechanism involving growth differentiation factor 15." Clin Cancer Res.13(19):5825-33.
Huh, S. et al. (2010) "Macrophage inhibitory cytokine-1 regulates melanoma vascular development," Am J Pathol. 176 (6):2948-57.
International Search Report and Written Opinion for PCT/EP16/73520.
Jackson, A. et al. (2010) "Recognizing and avoiding siRNA off-target effects for target identification and therapeutic application," Nat Rev Drug Discov. 9(1):57-67.
Ji, R. (2011) "An immune-active tumor microenvironment favors clinical response to ipilimumab," Cancer Immunol Immunother. 61(7):1019-31.
Johnen, H et al. (2007) "Tumor-induced anorexia and weight loss are mediated by the TGF-beta superfamily cytokine MIC-1," Nat Med. 13(11):1333-40.
Jones, P. et al. (1986) "Replacing the complementarity-determining regions in a human antibody with those from a mouse." Nature. 321(6069):522-5.
Joshi, J. et al. (2011) "Growth Differentiation Factor 15 (GDF15)-Mediated HER2 Phosphorylation Reduces Trastuzumab Sensitivity of HER2-Overexpressing Breast Cancer Cells," Biochem Pharmacol. 82(9): 1090-1099.
Junker, M. (2015) Development and characterization of monoclonal antibodies to GDF-15 for potential use in cancer therapy. Ph.D. Thesis.
Kanasty, R. et al. (2013) "Delivery materials for siRNA therapeutics," Nat Mater. 12(11):967-77.
Kempf, T. et al. (2011) "GDF-15 is an inhibitor of leukocyte integrin activation required for survival after myocardial infarction in mice," Nat Med.17(5):581-588.
Knoepfel, S. et al. (2012) "Selection of RNAi-based inhibitors for anti-HIV gene therapy," World J Virol. 1(3):79-90.
Köhler, G. (1975) "Continuous cultures of fused cells secreting antibody of predefined specificity," Nature. 256 (5517):495-7.
Lasithiotakis, K. et al. (2006) "The incidence and mortality of cutaneous melanoma in southern Germany," Cancer. 107(6):1331-9.
Lavaud, P. et al. (2014) "Strategies to overcome trastuzumab resistance in HER2-overexpressing breast cancers: focus on new data from clinical trials," BMC Medicine 12:132, 10 pp.
Li, B et al. (2011) "RSEM: accurate transcript quantification from RNA-Seq data with or without a reference genome," BMC Bioinformatics. 12:323, 16 pp.
Llopiz et al. (2008) "Combined immunization with adjuvant molecules poly(I:C) and anti-CD40 plus a tumor antigen has potent prophylactic and therapeutic antitumor effects," Cancer Immunology & Immunotherapy. 57(1):19-29.
Maier, J. et al. (2015) "Knockdown of platinum-induced growth differentiation factor 15 abrogates p27-mediated tumor growth delay in the chemoresistant ovarian cancer model A2780cis," Cancer Med. 4(2):253-67.
Marks, J. et al. (1991) "By-passing immunization: Human antibodies from V-gene libraries displayed on phage." J Mol Biol. 222(3):581-97.

(56) References Cited

OTHER PUBLICATIONS

Miller, J. et al. (2015) "The journey from discoveries in fundamental immunology to cancer immunotherapy," Cancer Cell. 27(4):439-49.
Mimeault, K. et al. (2010) "Divergent molecular mechanisms underlying the pleiotropic functions of macrophage inhibitory cytokine-1 in cancer," J Cell Physiol. 224(3):626-35.
Mimeault, M et al. (2013) "Marked improvement of cytotoxic effects induced by docetaxel on highly metastatic and androgen-independent prostate cancer cells by downregulating macrophage inhibitory cytokine-1." Br J Cancer. 108 (5):1079-91.
Motz, G. et al. (2014) "Tumor endothelium FasL establishes a selective immune barrier promoting tolerance in tumors," Nat Med. 20(6):607-15.
Motzer, R. et al. (2015) "Nivolumab versus Everolimus in Advanced Renal-Cell Carcinoma," N Engl J Med. 373 (19):1803-13.
Neuzillet, C. et al. (2015) "Targeting the TGFβ pathway for cancer therapy," Pharmacol Ther.147:22-31.
Reardon, D. et al. (2013) "An Update of Vaccine Therapy and Other Immunotherapeutic Approaches to Glioblastoma," Expert Rev Vaccines. 12(6):597-615.
Ribas, A. et al. (2015) "Pembrolizumab versus investigator-choice chemotherapy for ipilimumab-refractory melanoma (KEYNOTE-002): a randomised, controlled, phase 2 trial," Lancet Oncol. 16:908-18.
Riechmann, L. et al. (1988) "Reshaping human antibodies for therapy," Nature. 332(6162):323-7.
Rizvi, N. et al. (2015) "Cancer immunology: Mutational landscape determines sensitivity to PD-1 blockade in non-small cell lung cancer," Science. 348(6230):124-8.
Robert, C. et al. (2015) "Pembrolizumab versus Ipilimumab in Advanced Melanoma," N Engl J Med. 372:2521-2532.
Rothschild, S. et al. (2016) "SAKK 16/14: Anti-PD-L1 antibody durvalumab (MEDI4736) in addition to neoadjuvant chemotherapy in patients with stage IIIA(N2) non-small cell lung cancer (NSCLC)—A multicenter single-arm phase II trial," Journal of Thoracic Oncology vol. 11, Suppl. 4S: S106-S112.
Saerens, D et al. (2008) "Single-domain antibodies as building blocks for novel therapeutics," Curr Opin Pharmacol. 8(5):600-8.
Search Report Under Section 17 for GB1607801.6.
Siegel, D. (2002) "Recombinant monoclonal antibody technology." Transfus Clin Biol. 9(1):15-22.
Stefanescu R. et al. (2007) "Mass spectrometric approaches for elucidation of antigenantibody recognition structures in molecular immunology," Eur. J. Mass Spectrom. 13:69-75.
Suchard, S. et al. (2013) "A monovalent anti-human CD28 domain antibody antagonist: preclinical efficacy and safety," J Immunol. 191:4599-4610.
Suckau, D. et al. (1990) "Molecular epitope identification by limited proteolysis of an immobilized antigen-antibody complex and mass spectrometric peptide mapping," Proc Natl Acad Sci U S A. 87(24): 9848-9852.
Tanno, T. et al. (2011) "The TGF-β Family Member Growth Differentiation Factor 15 (GDF15) Regulates the Self-Renewal of Multiple Myeloma Cancer Stem Cells," Blood, 118(21):Abstract 2954.
Tanno, T. et al. (2010) "Growth differentiation factor 15 in erythroid health and disease," Curr Opin Hematol. 17(3): 184-190.
Taube, J. et al. (2014) "Association of PD-1, PD-1 ligands, and other features of the tumor immune microenvironment with response to anti-PD-1 therapy.", Clin Cancer Res. 20(19):5064-74.
Topalian, S. et al. (2014) "Survival, durable tumor remission, and long-term safety in patients with advanced melanoma receiving nivolumab," J. Clin. Oncol. 32(10):1020-1031.
Topalian, S. et al. (2015) "Immune checkpoint blockade: a common denominator approach to cancer therapy," Cancer Cell. 27(4):450-61.
Tsai, K. et al. (2015) "Clinical Chracteristics Predictive of Response to Pembrolizumab uin Advanced Melanoma," J Clin Oncol 33, 2015 (suppl; abstr 9031).

Tsui, K. et al. (2012) "Growth differentiation factor-15 upregulates interleukin-6 to promote tumorigenesis of prostate carcinoma PC-3 cells," J Mol Endocrinol. 49(2):153-63.
Tumeh, P. et al. (2014) "PD-1 blockade induces responses by inhibiting adaptive immune resistance," Nature. 515 (7528):568-71.
Van Der Burg, S, et al. (2014) "Immunoguiding, the final frontier in the immunotherapy of cancer." In Cancer Immunotherapy meets oncology (CM Britten, S Kreiter, M. Diken & HG Rammensee eds). Springer International Publishing Switzerland p. 37-51 ISBN: 978-3-319-05103-1.
Wallentin, L. et al. (2013) "GDF-15 for prognostication of cardiovascular and cancer morbidity and mortality in men." PLoS One. 8(12):e78797.
Wang, A et al. (2015) "The prognostic value of PD-L1 expression for non-small cell lung cancer patients: a meta-analysis," Eur J Surg Oncol. 41(4):450-6.
Yadav, M. et al. (2014) "Predicting immunogenic tumour mutations by combining mass spectrometry and exome sequencing," Nature. 515(7528):572-6.
Yoon, J. et al. (2013) "Activin receptor-like kinase5 inhibition suppresses mouse melanoma by ubiquitin degradation of Smad4, thereby derepressing eomesodermin in cytotoxic T lymphocytes," EMBO Mol Med.(11):1720-39.
Zhang, J. et al.(2015) "Prognostic value of pretreatment serum lactate dehydrogenase level in patients with solid tumors: a systematic review and meta-analysis," Scientific Reports 5:9800.
Zhao, L. et al. (2009) "Indication of Candidate Biomarkers of Therapeutic Response to Docetaxel by Proteomic Profiling," Cancer Research. 69(19):7696-7703.
Zhou, Z. et al. (2013) "Growth differentiation factor-15 suppresses maturation and function of dendritic cells and inhibits tumor-specific immune response," PLoS One. 8(11):e78618.
Roth, P. et al. (2010) "GDF-15 contributes to proliferation and immune escape of malignant gliomas," Clin Cancer Res. 16(15):3851-9.
Abd El-Aziz et al. "Cleavage of growth differentiation factor 15 (GDF15) by membrane type 1-matrix metalloproteinase abrogates GDF15-mediated suppression of tumor cell growth", Cancer Sci., Sep. 2007, vol. 98, No. 9, pp. 1330-1335.
Baek et al. "Upregulation and secretion of macrophage inhibitory cytokine-1 (MIC-1) in gastric cancers", Clinica Chimica Acta, 2009, vol. 401, pp. 128-133, doi: 10.1016/j.cca.2008.12.008.
Baek et al., "Nonsteroidal Anti-Inflammatory Drug-Activated Gene-1 Over Expression in Transgenic Mice Suppresses Intestinal Neoplasia", Gastroenterology, 2006, vol. 131, pp. 1553-1560.
Bauskin et al., "The TGF-ß Superfamily Cytokine MIC-1/GDF15: Secretory Mechanisms Facilitate Creation of Latent Stromal Stores", Journal of Interferon & Cytokine Research, 2010, vol. 30, No. 6, pp. 27-35.
Blanco-Calvo et al., "Circulating levels of GDF15, MMP7 and miR-200c as a poor prognostic signature in gastric cancer", Future Oncology, 2014, vol. 10, No. 7, pp. 1187-1202.
Bootcov et a., "MIC-1, a novel macrophage inhibitory cytokine. Is a divergent member of the TGF-ß superfamily", Proc. Nat'l. Acad. Sci., Oct. 1997, vol. 94, pp. 11514-11519.
Boyle et al., "Macrophage Inhibitory Cytokine-1 Is Overexpressed in Malignant Melanoma and Is Associated with Tumorigenicity", Aug. 28, 2008, vol. 129, pp. 383-391, doi: 10.1038/jid.2008.270.
Brown et al., "MIC-1 Serum Level and Genotype: Associations with Progress and Prognosis of Colorectal Carcinoma", Clinical Cancer Research, Jul. 2003, vol. 9, pp. 2642-2650.
Bruzzese et al., "Local and Systemic Protumorigenic Effects of Cancer-Associated Fibroblast-Derived GDF15", Cancer Research, Apr. 29, 2014, vol. 74, No. 13, pp. 3408-3418, doi: 10.1158/0008-5472.CAN-13-2259.
Corre et al., "Bioactivity and Prognostic Significance of Growth Differentiation Factor GDF15 Secreted by Bone Marrow Mesenchymal Stem Cells in Multiple Myeloma", Cancer Research, Feb. 2, 2012, vol. 72, No. 6, pp. 1395-1407, doi: 10.1158/0008-5472.CAN-11-0188.
Fisher et al., "MIC-1/GDF15 in Barrett's oesophagus and oesophageal adenocarcinoma", British Journal of Cancer, 2015, vol. 112, pp. 1384-1391, doi: 10.1038/bjc.2015.100.

(56) References Cited

OTHER PUBLICATIONS

Galon et al., "Type, Density, and Location of Immune Cells Within Human Colorectal Tumors Predict Clinical Outcome", Science Mag., Sep. 29, 2006, vol. 313, pp. 1960-1993.
Griner et al., "Growth differentiation factor 15 stimulates rapamycin-sensitive ovarian cancer cell growth and invasion", Biochemical Pharmacology, vol. 85, pp. 46-58.
Hadrup et al., "Effector CD4 and CD8 T Cells and Their Role in the Tumor Microenvironment", Cancer Microenvironment, 2013, vol. 6, pp. 123-133.
Huh et al., "Macrophage Inhibitory Cytokine-1 Regulates Melanoma Vascular Development", The American Journal of Pathology, Jun. 2010, vol. 176, No. 6, pp. 2948-2957.
Husaini et al., "Macrophage Inhibitory Cytokine-1 (MIC-1/GDF15) Slows Cancer Development but Increases Metastases in TRAMP Prostate Cancer Prone Mice", PLOS One, Aug. 2012, vol. 7, No. 8, pp. 1-9.
Ji et al., "Twist promotes invasion and cisplatin resistance in pancreatic cancer cells through growth differentiation factor 15", Molecular Medicine Reports, 2015, vol. 12, pp. 3841-3848.
Jones et al., "Supraphysiologic Administration of GDF11 Induces Cachexia in Part by Upregulating GDF15", Cell Reports, 2018, vol. 22, pp. 1522-1530.
Joshi et al., "Growth differentiation factor 15 (GDF15)-mediated HER2 phosphorylation reduces trastuzumab sensitivity of HER2-overexpressing breast cancer cells", Biochemical Pharmacology, 2011, vol. 82, pp. 1090-1099.
Kang et al., "Tolfenamic Acid Induces Apoptosis and Growth Inhibition in Head and Neck Cancer: Involvement of NAG-1 Expression", PLOS One, Apr. 2012, vol. 7, No. 4, pp. 1-10.
Kim et al., "Implication of NAG-1 in synergistic induction of apoptosis by combined treatment of sodium salicylate and PI3K/MEK1/2 inhibitors in A549 human lung adenocarcinoma cells", Biochemical Pharmacology, 2008, vol. 75, pp. 1751-1760.
Kim et al., "Macrophage inhibitory cytokine-1 activates AKT and ERK-1/2 via the transactivation of ErbB2 in human breast and gastric cancer cells", Carcinogenesis, 2008, vol. 29, No. 4, pp. 704-712.
Kim et al., "NSAID-activated gene 1 mediates pro-inflammatory signaling activation and paclitaxel chemoresistance in type I human epithelial ovarian cancer stem-like cells", Oncotarget, Sep. 30, 2016, vol. 7, No. 44, pp. 72148-72166.
Li et al., "GDF15 promotes EMT and metastasis in colorectal cancer", Oncotarget, Oct. 22, 2015, vol. 7, No. 1, pp. 860-872.
Li et al., "Growth differentiation factor 15 is a promising diagnostic and prognostic biomarker in colorectal cancer", J. Cell. Mol. Med., 2016, vol. 20, No. 8, pp. 1420-1426.
Liu et al., "Association of Serum Level Growth Differentiation Factor 15 with Liver Cirrhosis and Hepatocellular Carcinoma", PLOS One, May 21, 2015, vol. 10, No. 5, pp. 1-13.
Maasho et al., "Cutting Edge: NKG2D Is a Costimulatory Receptor for Human Naive CD8+ T Cells", The Journal of Immunology, 2005, vol. 174, No. 8, pp. 4480-4484.
Mehta et al., "A Prospective Study of Macrophage Inhibitory Cytokine-1 (MIC-1/GDF15) and Risk of Colorectal Cancer", JNCI, Apr. 9, 2014, vol. 106, No. 4, pp. 1-8.
Mehta et al., "Association Between Plasma Levels of Macrophage Inhibitory Cytokine-1 Before Diagnosis of Colorectal Cancer and Mortality", Gastroenterology, 2015, vol. 149, pp. 614-622.
Patel et al., "GDF15 Provides an Endocrine Signal of Nutritional Stress in Mice and Humans", Cell Metabolism, 2019, vol. 29+, pp. 707-718.
Peng et al., "Growth and differentiation factor 15 regulates PD-LI expression in glioblastoma", Cancer Management and Research, 2019, vol. 11, pp. 2653-2661.
Roth et al., "GDF-15 Contributes to Proliferation and Immune Escape of Malignant Glinomas", Clinical Cancer Research, Jun. 9, 2010, vol. 16, pp. 3851-3860.
Schiegnitz, et al., "GDF 15 as an anti-apoptotic, diagnostic and prognostic marker in oral squamous cell carcinoma", Oral Oncology, 2012, vol. 48, pp. 608-614.
Schiegnitz, et al., "Growth differentiation factor 15 as a radiation-induced marker in oral carcinoma increasing radiation resistance", Journal of Oral Pathology and Medicine, 2016, vol. 45, pp. 63-69.
Sela-Culang et al. (2013) "The structural basis of antibody-antigen recognition," Frontiers in Immunology, vol. 4, Article 302, 13 pp.
Selander et al., "Serum Macrophage Inhibitory Cytokine-1 Concentrations Correlate with the Presence of Prostate Cancer", Cancer Epidemiology, Biomarkers & Prevention, Mar. 2007, vol. 16, No. 3, 532-537.
Senapati et al., "Overexpression of macrophage inhibitory cytokine-1 induces metastasis of human prostate cancer cells through the FAK-RhoA signaling pathway", Oncogene, 2010, vol. 29, pp. 1293-1302.
Senovilla et al., "Prognostic and predictive value of the immune infiltrate in cancer", Trial Watch, Oncolmmunology, 2012, vol. 1, No. 8, pp. 1323-1343.
Shnaper et al., "Elevated levels of MIC-1/GDF15 in the cerebrospinal fluid of patients are associated with glioblastoma and worse outcome", Int. J. Cancer, 2009, vol. 125, pp. 2624-2630.
Staff et al., "Elevated Plasma Growth Differentiation Factor-15 Correlates with Lymph Node Metastases and Poor Survival in Endometrial Cancer", Clinical Cancer Research, Jul. 15, 2011, vol. 17, No. 14, pp. 4825-4833.
Staff et al., "Growth differentiation factor-15 as a prognostic biomarker in ovarian cancer", Gynecologic Oncology, 2010, vol. 118, pp. 237-243.
Tanno et al., "Growth differentiating factor 15 enhances the tumor-initiating and self-renewal potential of multiple myeloma cells", Blood, Jan. 30, 2014, vol. 123, No. 5, pp. 725-733.
Tsui et al., "Growth differentiation factor-15 upregulates interleukin-6 to promote tumorigenesis of prostate carcinoma PC-3 cells", Journal of Molecular Endocrinology, 2012, vol. 49, pp. 153-163.
Walsh et al., "NKG2D Receptor Signaling Enhances Cytolytic Activity by Virus-Specific CD8+ T Cells: Evidence for a Protective Role in Virus-Induced Encephalitis", Journal of Virology, Mar. 2008, vol. 82, No. 6, pp. 3031-3044.
Wang et al., "The H6D genetic variation of GDF15 is associated with genesis, progress, and prognosis in colorectal cancer", Pathology—Research and Practice, 2015, vol. 211, pp. 845-850.
Westhrin et al., "Growth differentiation factor 15 (GDF15) promotes osteoclast differentiation and inhibits osteoblast differentiation and high serum GDF15 levels are associated with multiple myeloma bone disease", haematologica, 2015, vol. 100, pp. 511-514.
Xu et al., "Growth differentiation factor 15 induces growth and metastasis of human liver cancer stem-like cells via AKT/GSK-3ß/ß-catenin signaling", Oncotarget, 2017, vol. 8, No. 10, pp. 16972-16987.
Yang et al., "Elevated level of serum growth differentiation factor 15 is associated with oral leukoplakia and oral squamous cell carcinoma", Journal of Oral Pathology and Medicine, 2014, vol. 43, pp. 28-34.
Yang et al., "GDF 15 is a potential predictive biomarker for TPF induction chemotherapy and promotes tumorigenesis and progression in oral squamous cell carcinoma", Annals of Oncology, 2014, vol. 25, pp. 1215-1222.
Yu et al., "Tumor-infiltrating T lymphocytes: friends of foes?", Laboratory Investigation, 2006, vol. 86, pp. 231-345.

\* cited by examiner p=0.0093 p=0.0311 ically act on any target cell within the body that is connected to the blood circulation, provided that the potential target cell expresses a receptor for the soluble GDF-15 ligand.

SEQUENCE LISTING

<160> NUMBER OF SEQ ID NOS: 52

<210> SEQ ID NO 1
<211> LENGTH: 97
<212> TYPE: PRT
<213> ORGANISM: Mus musculus

<400> SEQUENCE: 1

Gln Val Lys Leu Gln Gln Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Lys Arg Tyr Asn Pro Thr
        50                  55                  60

Leu Lys Ser Arg Leu Thr Ile Ser Lys Asp Pro Ser Arg Asn Gln Val
65                  70                  75                  80

Phe Leu Lys Ile Thr Ser Val Asp Thr Ala Asp Thr Ala Thr Tyr Tyr
                85                  90                  95

Cys

<210> SEQ ID NO 2
<211> LENGTH: 88
<212> TYPE: PRT
<213> ORGANISM: Mus musculus

<400> SEQUENCE: 2

Asp Ile Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
                20                  25                  30

Val Ala Trp Phe Leu Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys
                85

<210> SEQ ID NO 3
<211> LENGTH: 10
<212> TYPE: PRT
<213> ORGANISM: Mus musculus

<400> SEQUENCE: 3

Gly Phe Ser Leu Ser Thr Ser Gly Met Gly
1               5                   10

```
<210> SEQ ID NO 4
<211> LENGTH: 7
<212> TYPE: PRT
<213> ORGANISM: Mus musculus

<400> SEQUENCE: 4

Ile Tyr Trp Asp Asp Asp Lys
1               5

<210> SEQ ID NO 5
<211> LENGTH: 10
<212> TYPE: PRT
<213> ORGANISM: Mus musculus

<400> SEQUENCE: 5

Ala Arg Ser Ser Tyr Gly Ala Met Asp Tyr
1               5                   10

<210> SEQ ID NO 6
<211> LENGTH: 6
<212> TYPE: PRT
<213> ORGANISM: Mus musculus

<400> SEQUENCE: 6

Gln Asn Val Gly Thr Asn
1               5

<210> SEQ ID NO 7
<211> LENGTH: 9
<212> TYPE: PRT
<213> ORGANISM: Mus musculus

<400> SEQUENCE: 7

Gln Gln Tyr Asn Asn Phe Pro Tyr Thr
1               5

<210> SEQ ID NO 8
<211> LENGTH: 114
<212> TYPE: PRT
<213> ORGANISM: Artificial Sequence
<220> FEATURE:
<223> OTHER INFORMATION: recombinant mature human GDF-15 protein

<400> SEQUENCE: 8

Gly Ser Ala Arg Asn Gly Asp His Cys Pro Leu Gly Pro Gly Arg Cys
1               5                   10                  15

Cys Arg Leu His Thr Val Arg Ala Ser Leu Glu Asp Leu Gly Trp Ala
            20                  25                  30

Asp Trp Val Leu Ser Pro Arg Glu Val Gln Val Thr Met Cys Ile Gly
        35                  40                  45

Ala Cys Pro Ser Gln Phe Arg Ala Ala Asn Met His Ala Gln Ile Lys
    50                  55                  60

Thr Ser Leu His Arg Leu Lys Pro Asp Thr Val Pro Ala Pro Cys Cys
65                  70                  75                  80

Val Pro Ala Ser Tyr Asn Pro Met Val Leu Ile Gln Lys Thr Asp Thr
                85                  90                  95

Gly Val Ser Leu Gln Thr Tyr Asp Asp Leu Leu Ala Lys Asp Cys His
            100                 105                 110

Cys Ile
```

```
<210> SEQ ID NO 9
<211> LENGTH: 308
<212> TYPE: PRT
<213> ORGANISM: Homo sapiens

<400> SEQUENCE: 9

Met Pro Gly Gln Glu Leu Arg Thr Val Asn Gly Ser Gln Met Leu Leu
1               5                   10                  15

Val Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
            275                 280                 285

Asp Thr Gly Val Ser Leu Gln Thr Tyr Asp Asp Leu Leu Ala Lys Asp
    290                 295                 300

Cys His Cys Ile
305

<210> SEQ ID NO 10
<211> LENGTH: 322
<212> TYPE: PRT
<213> ORGANISM: Artificial Sequence
<220> FEATURE:
<223> OTHER INFORMATION: human GDF-15 precursor protein + N-terminal and
      C-terminal GSGS linker

<400> SEQUENCE: 10

Gly Ser Gly Ser Gly Ser Gly Met Pro Gly Gln Glu Leu Arg Thr Val
```

```
                1               5                   10                  15
            Asn Gly Ser Gln Met Leu Leu Val Leu Leu Val Leu Ser Trp Leu Pro
                        20                  25                  30
            His Gly Gly Ala Leu Ser Leu Ala Glu Ala Ser Arg Ala Ser Phe Pro
                        35                  40                  45
            Gly Pro Ser Glu Leu His Ser Glu Asp Ser Arg Phe Arg Glu Leu Arg
                50                  55                  60
            Lys Arg Tyr Glu Asp Leu Leu Thr Arg Leu Arg Ala Asn Gln Ser Trp
            65                  70                  75                  80
            Glu Asp Ser Asn Thr Asp Leu Val Pro Ala Pro Ala Val Arg Ile Leu
                            85                  90                  95
            Thr Pro Glu Val Arg Leu Gly Ser Gly Gly His Leu His Leu Arg Ile
                            100                 105                 110
            Ser Arg Ala Ala Leu Pro Glu Gly Leu Pro Glu Ala Ser Arg Leu His
                            115                 120                 125
            Arg Ala Leu Phe Arg Leu Ser Pro Thr Ala Ser Arg Ser Trp Asp Val
                        130                 135                 140
            Thr Arg Pro Leu Arg Arg Gln Leu Ser Leu Ala Arg Pro Gln Ala Pro
            145                 150                 155                 160
            Ala Leu His Leu Arg Leu Ser Pro Pro Ser Gln Ser Asp Gln Leu
                            165                 170                 175
            Leu Ala Glu Ser Ser Ser Ala Arg Pro Gln Leu Glu Leu His Leu Arg
                        180                 185                 190
            Pro Gln Ala Ala Arg Gly Arg Arg Ala Arg Ala Arg Asn Gly Asp
                        195                 200                 205
            His Cys Pro Leu Gly Pro Gly Arg Cys Cys Arg Leu His Thr Val Arg
                        210                 215                 220
            Ala Ser Leu Glu Asp Leu Gly Trp Ala Asp Trp Val Leu Ser Pro Arg
            225                 230                 235                 240
            Glu Val Gln Val Thr Met Cys Ile Gly Ala Cys Pro Ser Gln Phe Arg
                            245                 250                 255
            Ala Ala Asn Met His Ala Gln Ile Lys Thr Ser Leu His Arg Leu Lys
                        260                 265                 270
            Pro Asp Thr Val Pro Ala Pro Cys Cys Val Pro Ala Ser Tyr Asn Pro
                        275                 280                 285
            Met Val Leu Ile Gln Lys Thr Asp Thr Gly Val Ser Leu Gln Thr Tyr
                        290                 295                 300
            Asp Asp Leu Leu Ala Lys Asp Cys His Cys Ile Gly Ser Gly Ser Gly
            305                 310                 315                 320
            Ser Gly

<210> SEQ ID NO 11
<211> LENGTH: 10
<212> TYPE: PRT
<213> ORGANISM: Artificial Sequence
<220> FEATURE:
<223> OTHER INFORMATION: Flag peptide

<400> SEQUENCE: 11

Asp Tyr Lys Asp Asp Asp Asp Lys Gly Gly
1               5                   10

<210> SEQ ID NO 12
<211> LENGTH: 10
<212> TYPE: PRT
<213> ORGANISM: Artificial Sequence
```

```
<220> FEATURE:
<223> OTHER INFORMATION: HA peptide

<400> SEQUENCE: 12

Tyr Pro Tyr Asp Val Pro Asp Tyr Ala Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 13

Glu Leu His Leu Arg Pro Gln Ala Ala Arg Gly Arg Arg
1               5                   10

<210> SEQ ID NO 14
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 14

Leu His Leu Arg Pro Gln Ala Ala Arg Gly Arg Arg Arg
1               5                   10

<210> SEQ ID NO 15
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 15

His Leu Arg Pro Gln Ala Ala Arg Gly Arg Arg Arg Ala
1               5                   10

<210> SEQ ID NO 16
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 16

Leu Arg Pro Gln Ala Ala Arg Gly Arg Arg Arg Ala Arg
1               5                   10

<210> SEQ ID NO 17
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 17

Arg Pro Gln Ala Ala Arg Gly Arg Arg Arg Ala Arg Ala
1               5                   10

<210> SEQ ID NO 18
<211> LENGTH: 13
<212> TYPE: PRT
<213> ORGANISM: Artificial Sequence
<220> FEATURE:
```

<223> OTHER INFORMATION: peptide derived from human GDF-15

<400> SEQUENCE: 18

Pro Gln Ala Ala Arg Gly Arg Arg Arg Ala Arg Ala Arg
1               5                   10

<210> SEQ ID NO 19
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 19

Gln Ala Ala Arg Gly Arg Arg Arg Ala Arg Ala Arg Asn
1               5                   10

<210> SEQ ID NO 20
<211> LENGTH: 13
<212> TYPE: PRT
<213> ORGANISM: Artificial Sequence
<220> FEATURE:
<223> OTHER INFORMATION: peptide derived from human GDF-15

<400> SEQUENCE: 20

Met His Ala Gln Ile Lys Thr Ser Leu His Arg Leu Lys
1               5                   10

<210> SEQ ID NO 21
<211> LENGTH: 291
<212> TYPE: DNA
<213> ORGANISM: Mus musculus

<400> SEQUENCE: 21
caagtgaagc tgcagcagtc aggccctggg atattgcagt cctcccagac cctcagtctg      60
acttgttctt tctctgggtt ttcactgagt acttctggta tgggtgtgag ctggattcgt     120
cagccttcag gaaagggtct ggagtggctg gcacacattt actgggatga tgacaagcgc     180
tataacccaa ccctgaagag ccggctcaca atctccaagg atccctccag aaaccaggta     240
ttcctcaaga tcaccagtgt ggacactgca gatactgcca catactactg t              291

<210> SEQ ID NO 22
<211> LENGTH: 264
<212> TYPE: DNA
<213> ORGANISM: Mus musculus

<400> SEQUENCE: 22
gacattgtgc tcacccagtc tccaaaattc atgtccacat cagtaggaga cagggtcagc      60
gtcacctgca aggccagtca gaatgtgggt actaatgtgg cctggtttct acagaaacca     120
gggcaatctc ctaaagcact tatttactcg gcatcctacc ggtacagtgg agtccctgat     180
cgcttcacag gcagtggatc tgggacagat tcactctca ccatcagcaa cgtgcagtct      240
gaagacttgg cagagtattt ctgt                                           264

<210> SEQ ID NO 23
<211> LENGTH: 30
<212> TYPE: DNA
<213> ORGANISM: Mus musculus

<400> SEQUENCE: 23
gctcgaagtt cctacggggc aatggactac                                      30

<210> SEQ ID NO 24
<211> LENGTH: 27
<212> TYPE: DNA
<213> ORGANISM: Mus musculus

<400> SEQUENCE: 24
cagcaatata acaactttcc gtacacg                                          27

<210> SEQ ID NO 25
<211> LENGTH: 16
<212> TYPE: PRT
<213> ORGANISM: Homo sapiens

<400> SEQUENCE: 25

Glu Val Gln Val Thr Met Cys Ile Gly Ala Cys Pro Ser Gln Phe Arg
1               5                   10                  15

<210> SEQ ID NO 26
<211> LENGTH: 21
<212> TYPE: PRT
<213> ORGANISM: Homo sapiens

<400> SEQUENCE: 26

Thr Asp Thr Gly Val Ser Leu Gln Thr Tyr Asp Asp Leu Leu Ala Lys
1               5                   10                  15

Asp Cys His Cys Ile
            20

<210> SEQ ID NO 27
<211> LENGTH: 448
<212> TYPE: PRT
<213> ORGANISM: Artificial Sequence
<220> FEATURE:
<223> OTHER INFORMATION: amino acid sequence of the heavy chain of the
      H1L5 humanized B1-23 anti-GDF-15 antibody

<400> SEQUENCE: 27

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Lys Arg Tyr Asn Pro Thr
    50                  55                  60

Leu Lys Ser Arg Leu Thr Ile Thr Lys Asp Pro Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Ser Tyr Gly Ala Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 28
<211> LENGTH: 118
<212> TYPE: PRT
<213> ORGANISM: Artificial Sequence
<220> FEATURE:
<223> OTHER INFORMATION: amino acid sequence of the heavy chain variable
      domain of the H1L5 humanized B1-23 anti-GDF-15 antibody

<400> SEQUENCE: 28

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Lys Arg Tyr Asn Pro Thr
    50                  55                  60

Leu Lys Ser Arg Leu Thr Ile Thr Lys Asp Pro Ser Lys Asn Gln Val
65                  70                  75                  80

Val Leu Thr Met Thr Asn Met Asp Pro Val Asp Thr Ala Thr Tyr Tyr
                85                  90                  95

```
Cys Ala Arg Ser Ser Tyr Gly Ala Met Asp Tyr Trp Gly Gln Gly Thr
            100                 105                 110

Leu Val Thr Val Ser Ser
        115

<210> SEQ ID NO 29
<211> LENGTH: 330
<212> TYPE: PRT
<213> ORGANISM: Artificial Sequence
<220> FEATURE:
<223> OTHER INFORMATION: amino acid sequence of the heavy chain constant
      domain of the H1L5 humanized B1-23 anti-GDF-15 antibody

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

<210> SEQ ID NO 30
<211> LENGTH: 211
<212> TYPE: PRT
<213> ORGANISM: Artificial Sequence
<220> FEATURE:
<223> OTHER INFORMATION: amino acid sequence of the light chain of the
      H1L5 humanized B1-23 anti-GDF-15 antibody

<400> SEQUENCE: 30

Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Glu Phe Thr Leu Thr Ile Ser Ser Leu Gln Pro
65                  70                  75                  80

Glu Asp Phe Ala Ala Tyr Phe Cys Gln Gln Tyr Asn Asn Phe Pro Tyr
                85                  90                  95

Thr Phe Gly Gly Gly Thr Lys Leu Glu Ile Lys Arg Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 31
<211> LENGTH: 108
<212> TYPE: PRT
<213> ORGANISM: Artificial Sequence
<220> FEATURE:
<223> OTHER INFORMATION: amino acid sequence of the light chain variable
      domain of the H1L5 humanized B1-23 anti-GDF-15 antibody

<400> SEQUENCE: 31

Asp Ile Val Leu Thr Gln Ser Pro Ser Phe Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Glu Phe Thr Leu Thr Ile Ser Ser Leu Gln Pro

```
                 65                  70                  75                  80
Glu Asp Phe Ala Ala Tyr Phe Cys Gln Gln Tyr Asn Asn Phe Pro Tyr
                 85                  90                  95

Thr Phe Gly Gly Gly Thr Lys Leu Glu Ile Lys Arg
                100                 105

<210> SEQ ID NO 32
<211> LENGTH: 103
<212> TYPE: PRT
<213> ORGANISM: Artificial Sequence
<220> FEATURE:
<223> OTHER INFORMATION: amino acid sequence of the light chain constant
      domain of the H1L5 humanized B1-23 anti-GDF-15 antibody

<400> SEQUENCE: 32

Ala Pro Ser Val Phe Ile Phe Pro Pro Ser Asp Glu Gln Leu Lys Ser
1               5                   10                  15

Gly Thr Ala Ser Val Val Cys Leu Leu Asn Asn Phe Tyr Pro Arg Glu
                20                  25                  30

Ala Lys Val Gln Trp Lys Val Asp Asn Ala Leu Gln Ser Gly Asn Ser
            35                  40                  45

Gln Glu Ser Val Thr Glu Gln Asp Ser Lys Asp Ser Thr Tyr Ser Leu
        50                  55                  60

Ser Ser Thr Leu Thr Leu Ser Lys Ala Asp Tyr Glu Lys His Lys Val
65                  70                  75                  80

Tyr Ala Cys Glu Val Thr His Gln Gly Leu Ser Ser Pro Val Thr Lys
                85                  90                  95

Ser Phe Asn Arg Gly Glu Cys
                100

<210> SEQ ID NO 33
<211> LENGTH: 448
<212> TYPE: PRT
<213> ORGANISM: Artificial Sequence
<220> FEATURE:
<223> OTHER INFORMATION: amino acid sequence of the heavy chain of the
      chimeric B1-23 anti-GDF-15 antibody

<400> SEQUENCE: 33

Gln Val Lys Leu Gln Gln Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Lys Arg Tyr Asn Pro Thr
        50                  55                  60

Leu Lys Ser Arg Leu Thr Ile Ser Lys Asp Pro Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Ser Ser Tyr Gly Ala Met Asp Tyr Trp Gly Gln Gly Thr
                100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
```

```
                145                 150                 155                 160
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 34
<211> LENGTH: 118
<212> TYPE: PRT
<213> ORGANISM: Artificial Sequence
<220> FEATURE:
<223> OTHER INFORMATION: amino acid sequence of the heavy chain variable
      domain of the chimeric B1-23 anti-GDF-15 antibody

<400> SEQUENCE: 34

Gln Val Lys Leu Gln Gln Ser Gly Pro Gly Ile Leu Gln Ser Ser Gln
1               5                   10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
                35                  40                  45

Trp Leu Ala His Ile Tyr Trp Asp Asp Asp Lys Arg Tyr Asn Pro Thr
                50                  55                  60
```

```
Leu Lys Ser Arg Leu Thr Ile Ser Lys Asp Pro Ser Arg Asn Gln Val
 65                  70                  75                  80

Phe Leu Lys Ile Thr Ser Val Asp Thr Ala Asp Thr Ala Thr Tyr Tyr
                 85                  90                  95

Cys Ala Arg Ser Ser Tyr Gly Ala Met Asp Tyr Trp Gly Gln Gly Thr
            100                 105                 110

Ser Val Thr Val Ser Ser
        115

<210> SEQ ID NO 35
<211> LENGTH: 330
<212> TYPE: PRT
<213> ORGANISM: Artificial Sequence
<220> FEATURE:
<223> OTHER INFORMATION: amino acid sequence of the heavy chain constant
      domain of the chimeric B1-23 anti-GDF-15 antibody

<400> SEQUENCE: 35

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 36
<211> LENGTH: 214
<212> TYPE: PRT
<213> ORGANISM: Artificial Sequence
<220> FEATURE:
<223> OTHER INFORMATION: amino acid sequence of the light chain of the
      chimeric B1-23 anti-GDF-15 antibody

<400> SEQUENCE: 36

Asp Ile Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Leu Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Asn Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 111
<212> TYPE: PRT
<213> ORGANISM: Artificial Sequence
<220> FEATURE:
<223> OTHER INFORMATION: amino acid sequence of the light chain variable
      domain of the chimeric B1-23 anti-GDF-15 antibody

<400> SEQUENCE: 37

Asp Ile Val Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Leu Gln Lys Pro Gly Gln Ser Pro Lys Ala Leu Ile
        35                  40                  45

```
Tyr Ser Ala Ser Tyr Arg Tyr Ser Gly Val Pro Asp Arg Phe Thr Gly
            50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Asn Phe Pro Tyr
                85                  90                  95

Thr Phe Gly Gly Gly Thr Lys Leu Glu Ile Lys Arg Thr Val Ala
                100                 105                 110

<210> SEQ ID NO 38
<211> LENGTH: 103
<212> TYPE: PRT
<213> ORGANISM: Artificial Sequence
<220> FEATURE:
<223> OTHER INFORMATION: amino acid sequence of the light chain constant
      domain of the chimeric B1-23 anti-GDF-15 antibody

<400> SEQUENCE: 38

Ala Pro Ser Val Phe Ile Phe Pro Pro Ser Asp Glu Gln Leu Lys Ser
 1               5                  10                  15

Gly Thr Ala Ser Val Val Cys Leu Leu Asn Asn Phe Tyr Pro Arg Glu
                20                  25                  30

Ala Lys Val Gln Trp Lys Val Asp Asn Ala Leu Gln Ser Gly Asn Ser
            35                  40                  45

Gln Glu Ser Val Thr Glu Gln Asp Ser Lys Asp Ser Thr Tyr Ser Leu
        50                  55                  60

Ser Ser Thr Leu Thr Leu Ser Lys Ala Asp Tyr Glu Lys His Lys Val
 65                  70                  75                  80

Tyr Ala Cys Glu Val Thr His Gln Gly Leu Ser Ser Pro Val Thr Lys
                85                  90                  95

Ser Phe Asn Arg Gly Glu Cys
                100

<210> SEQ ID NO 39
<211> LENGTH: 120
<212> TYPE: PRT
<213> ORGANISM: Artificial Sequence
<220> FEATURE:
<223> OTHER INFORMATION: amino acid sequence of the heavy chain variable
      domain of the 01G06 antibody

<400> SEQUENCE: 39

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Gln Ser Leu Glu Trp Met
            35                  40                  45

Gly Gln Ile Asn Pro Asn Asn Gly Leu Ile Phe Phe Asn Gln Lys Phe
        50                  55                  60

Gln Gly Arg Val Thr Leu Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
                100                 105                 110

Gly Thr Leu Val Thr Val Ser Ser
            115                 120
```

<210> SEQ ID NO 40
<211> LENGTH: 107
<212> TYPE: PRT
<213> ORGANISM: Artificial Sequence
<220> FEATURE:
<223> OTHER INFORMATION: amino acid sequence of the light chain variable
      domain of the 01G06 antibody

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Asp Pro Tyr
                85                  90                  95

Thr Phe Gly Gln Gly Thr Lys Leu Glu Ile Lys
            100                 105

<210> SEQ ID NO 41
<211> LENGTH: 118
<212> TYPE: PRT
<213> ORGANISM: Artificial Sequence
<220> FEATURE:
<223> OTHER INFORMATION: amino acid sequence of the heavy chain variable
      domain of the 03G05 antibody

<400> SEQUENCE: 41

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Asn Gln Arg Pro Gly Gln Gly Leu Glu Trp Ile
        35                  40                  45

Gly Asp Ile Asn Pro Ser Asn Gly Arg Ser Lys Tyr Asn Glu Lys Phe
    50                  55                  60

Lys Asn Lys Ala Thr Met Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Val Leu Asp Gly Ala Met Asp Tyr Trp Gly Gln Gly Thr
            100                 105                 110

Ser Val Thr Val Ser Ser
        115

<210> SEQ ID NO 42
<211> LENGTH: 111
<212> TYPE: PRT
<213> ORGANISM: Artificial Sequence
<220> FEATURE:
<223> OTHER INFORMATION: amino acid sequence of the light chain variable
      domain of the 03G05 antibody

<400> SEQUENCE: 42

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Ser Lys Leu Glu Ile Lys
            100                 105                 110
```

<210> SEQ ID NO 43
<211> LENGTH: 119
<212> TYPE: PRT
<213> ORGANISM: Artificial Sequence
<220> FEATURE:
<223> OTHER INFORMATION: amino acid sequence of the heavy chain variable
      domain of the 04F08 antibody

<400> SEQUENCE: 43

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Thr Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Asn Asn Gln Val
65                  70                  75                  80

Phe Leu Lys Ile Thr Ser Val Asp Thr Ala Asp Thr Ala Thr Tyr Tyr
                85                  90                  95

Cys Ala Gln Thr Gly Tyr Ser Asn Leu Phe Ala Tyr Trp Gly Gln Gly
            100                 105                 110

Thr Leu Val Thr Val Ser Ala
        115
```

<210> SEQ ID NO 44
<211> LENGTH: 107
<212> TYPE: PRT
<213> ORGANISM: Artificial Sequence
<220> FEATURE:
<223> OTHER INFORMATION: amino acid sequence of the light chain variable
      domain of the 04F08 antibody

<400> SEQUENCE: 44

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Leu Gly Gln Ser Pro Lys Thr Leu Ile
        35                  40                  45

Tyr Ser Ala Ser Tyr Arg Tyr Ser Gly Val Pro Asp Arg Phe Thr Gly
    50                  55                  60
```

```
Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys
            100                 105

<210> SEQ ID NO 45
<211> LENGTH: 119
<212> TYPE: PRT
<213> ORGANISM: Artificial Sequence
<220> FEATURE:
<223> OTHER INFORMATION: amino acid sequence of the heavy chain variable
      domain of the 06C11 antibody

<400> SEQUENCE: 45

Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Asn Thr Tyr
                 20                  25                  30

Gly Met Gly Val Ser Trp Ile Arg Gln Pro Ser Gly Lys Gly Leu Glu
             35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Ala Ser Asn Asn Arg Val
 65                  70                  75                  80

Phe Leu Lys Ile Thr Ser Val Asp Thr Ala Asp Thr Ala Thr Tyr Tyr
                 85                  90                  95

Cys Ala Gln Arg Gly Tyr Asp Asp Tyr Trp Gly Tyr Trp Gly Gln Gly
                100                 105                 110

Thr Leu Val Thr Ile Ser Ala
            115

<210> SEQ ID NO 46
<211> LENGTH: 107
<212> TYPE: PRT
<213> ORGANISM: Artificial Sequence
<220> FEATURE:
<223> OTHER INFORMATION: amino acid sequence of the light chain variable
      domain of the 06C11 antibody

<400> SEQUENCE: 46

Asp Ile Val Met Thr Gln Ser Gln Lys Phe Met Ser Thr Ser Val Gly
  1               5                  10                  15

Asp Arg Val Ser Val Thr Cys Lys Ala Ser Gln Asn Val Gly Thr Asn
                 20                  25                  30

Val Ala Trp Phe Gln Gln Lys Pro Gly Gln Ser Pro Lys Ala Leu Ile
             35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Ile Leu Thr Ile Ser Asn Val Gln Ser
 65                  70                  75                  80

Glu Asp Leu Ala Glu Tyr Phe Cys Gln Gln Tyr Asn Asn Tyr Pro Leu
                 85                  90                  95

Thr Phe Gly Ala Gly Thr Lys Leu Glu Leu Lys
            100                 105

<210> SEQ ID NO 47
<211> LENGTH: 120
```

<212> TYPE: PRT
<213> ORGANISM: Artificial Sequence
<220> FEATURE:
<223> OTHER INFORMATION: amino acid sequence of the heavy chain variable
      domain of the 08G01 antibody

<400> SEQUENCE: 47

Glu Val Leu Leu Gln Gln Ser Gly Pro Glu Val Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Glu Ile Asn Pro Asn Asn Gly Gly Thr Phe Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser
        115                 120

<210> SEQ ID NO 48
<211> LENGTH: 107
<212> TYPE: PRT
<213> ORGANISM: Artificial Sequence
<220> FEATURE:
<223> OTHER INFORMATION: amino acid sequence of the light chain variable
      domain of the 08G01 antibody

<400> SEQUENCE: 48

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys
            100                 105

<210> SEQ ID NO 49
<211> LENGTH: 119
<212> TYPE: PRT
<213> ORGANISM: Artificial Sequence
<220> FEATURE:
<223> OTHER INFORMATION: amino acid sequence of the heavy chain variable
      domain of the 14F11 antibody

<400> SEQUENCE: 49

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr

```
            20                  25                  30
Gly Met Gly Val Gly Trp Ile Arg Gln Pro Ser Gly Lys Gly Leu Glu
        35                  40                  45

Trp Leu Ala Asp Ile Trp Trp Asp Asp Lys Tyr Tyr Asn Pro Ser
    50                  55                  60

Leu Lys Ser Arg Leu Thr Ile Ser Lys Asp Thr Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser
        115

<210> SEQ ID NO 50
<211> LENGTH: 107
<212> TYPE: PRT
<213> ORGANISM: Artificial Sequence
<220> FEATURE:
<223> OTHER INFORMATION: amino acid sequence of the light chain variable
      domain of the 14F11 antibody

<400> SEQUENCE: 50

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Thr Phe Gly Gly Gly Thr Lys Leu Glu Met Lys
            100                 105

<210> SEQ ID NO 51
<211> LENGTH: 121
<212> TYPE: PRT
<213> ORGANISM: Artificial Sequence
<220> FEATURE:
<223> OTHER INFORMATION: amino acid sequence of the heavy chain variable
      domain of the 17B11 antibody

<400> SEQUENCE: 51

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Asn Asp Trp Asp Asp Lys Arg Tyr Lys Ser Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
```

```
                    85                  90                  95
Cys Ala Arg Arg Val Gly Gly Leu Glu Gly Tyr Phe Asp Tyr Trp Gly
                100                 105                 110

Gln Gly Thr Thr Leu Thr Val Ser Ser
            115                 120

<210> SEQ ID NO 52
<211> LENGTH: 111
<212> TYPE: PRT
<213> ORGANISM: Artificial Sequence
<220> FEATURE:
<223> OTHER INFORMATION: amino acid sequence of the light chain variable
      domain of the 17B11 antibody

<400> SEQUENCE: 52

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Arg Phe Ser Tyr Met His Trp Phe Gln Gln Lys Pro Gly Gln Ala Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Gly Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

COMBINATION THERAPY USING INHIBITORS OF HUMAN GROWTH AND DIFFERENTIATION FACTOR 15 (GDF-15) AND IMMUNE CHECKPOINT BLOCKERS

CROSS-REFERENCE TO RELATED APPLICATIONS

This application is a 35 U.S.C. § 371 filing of International Patent Application No. PCT/EP2016/073520, filed Sep. 30, 2016, which claims priority to Great Britain Patent Application No. 1517531.8, filed Oct. 2, 2015, and Great Britain Patent Application No. 1607801.6, filed Apr. 29, 2016. The entire disclosures of each of the aforementioned applications are incorporated herein by reference in their entirety.

FIELD OF THE INVENTION

The present invention relates to uses of inhibitors of human Growth and Differentiation Factor 15 (GDF-15), and to combined uses of such inhibitors with immune checkpoint blockers, in the treatment of solid cancers.

BACKGROUND

To date, many cancers are still areas of unmet medical needs, and accordingly, means to more effectively treat cancer are needed.

Many types of cancer are known to express growth factors, including factors such as VEGF, PDGF, TGF-β and GDF-15.

GDF-15, growth and differentiation factor-15, is a divergent member of the TGF-β superfamily. It is a protein which is intracellularly expressed as a precursor, subsequently processed and eventually becomes secreted from the cell into the environment. Both the active, fully processed (mature) form and the precursor of GDF-15 can be found outside cells. The precursor covalently binds via its COOH-terminal amino acid sequence to the extracellular matrix (Bauskin A R et al., Cancer Research 2005) and thus resides on the exterior of a cell. The active, fully processed (mature) form of GDF-15 is soluble and is found in blood sera. Thus, the processed form of GDF-15 may potentially act on any target cell within the body that is connected to the blood circulation, provided that the potential target cell expresses a receptor for the soluble GDF-15 ligand.

During pregnancy, GDF-15 is found under physiological conditions in the placenta. However, many malignant cancers (especially aggressive brain cancers, melanoma, lung cancer, gastrointestinal tumors, colon cancer, pancreatic cancer, prostate cancer and breast cancer (Mimeault M and Batra S K, J. Cell Physiol 2010)) exhibit increased GDF-15 levels in the tumor as well as in blood serum. Likewise, correlations have been described between high GDF-15 expression and chemoresistance (Huang C Y et al., Clin. Cancer Res. 2009) and between high GDF-15 expression and poor prognosis, respectively (Brown D A et al., Clin. Cancer Res. 2009).

GDF-15 is expressed in gliomas of different WHO grades as assessed by immunohistochemistry (Roth et al., Clin. Cancer Res. 2010). Further, Roth et al. stably expressed short hairpin RNA-expressing DNA constructs targeting endogenous GDF-15 or control constructs in SMA560 glioma cells. When using these pre-established stable cell lines, they observed that tumor formation in mice bearing GDF-15 knockdown SMA560 cells was delayed compared to mice bearing control constructs.

Patent applications WO 2005/099746 and WO 2009/021293 relate to an anti-human-GDF-15 antibody (Mab26) capable of antagonizing effects of human GDF-15 (hGDF-15) on tumor-induced weight loss in vivo in mice. Similarly, Johnen H et al. (Nature Medicine, 2007) reported effects of an anti-human-GDF-15 monoclonal antibody on cancer-induced anorexia and weight loss but did not observe any effects of the anti-human-GDF-15 antibody on the size of the tumor formed by the cancer.

WO 2014/049087 and PCT/EP2015/056654 relate to monoclonal antibodies to hGDF-15 and medical uses thereof.

A recently developed approach to cancer therapy is the use of immune checkpoint blockers such as inhibitors of human PD-1 and inhibitors of human PD-L1. A rationale behind the use of these immune checkpoint blockers is that by blocking immune checkpoints which prevent the immune system from targeting cancer antigens and the respective cancer cells, an immune response to the cancer may be more effective. While immune checkpoint blockers as well as particular combinations of immune checkpoint blockers have been shown improve patient survival in melanoma patients (Cully M, "Combinations with checkpoint inhibitors at wavefront of cancer immunotherapy.", Nat Rev Drug Discov. 2015 June; 14(6):374-5.), not all melanoma patients exhibited a complete response, and results for many other cancers are yet to be disclosed, still there are reasons (like the mutational burden) which suggest that results in other indications will be less favorable.

Thus, to date, there is still a need in the art for means to treat cancer more effectively. More particularly, there is still a lack of means that can be used for a more effective cancer immunotherapy.

DESCRIPTION OF THE INVENTION

The present invention meets the above needs and solves the above problems in the art by providing the embodiments described below:

In particular, in an effort to identify means to effectively treat cancer, the present inventors have surprisingly found that the likelihood of a response to a treatment with immune checkpoint blockers significantly decreases with increasing hGDF-15 levels in the patient sera. Thus, according to the invention, an inhibitor of hGDF-15 can be used to inhibit the negative effects of hGDF-15 on the patients' responses to the treatment with immune checkpoint blockers, and to improve the patients' responses to the treatment with immune checkpoint blockers.

Unexpectedly, the inventors have also found that there is an inverse correlation of hGDF-15 with the percentage of $CD8^+$ T lymphocytes in cancer metastases. This is noteworthy, because the presence of $CD8^+$ T lymphocytes is specifically required for tumor regression after immune checkpoint inhibition with an anti-PD-1 antibody. Thus, according to the invention, therapeutic inhibition of hGDF-15 can be used to increase the percentage of $CD8^+$ T lymphocytes in solid cancers including tumor metastases. This increase of $CD8^+$ T lymphocytes in the solid cancers can favorably be used for therapy, in particular immunotherapy, of the solid cancers. Thus, in a non-limiting aspect of the invention, a particularly favorable therapeutic combination is the combination of an hGDF-15 inhibitor with an immune checkpoint blocker. An advantageous effect of this combination is that inhibition of hGDF-15 will increase the percentage of CD8+ T lymphocytes in the solid cancers and thereby lead to a synergistic therapeutic effect with immune checkpoint inhibition.

In an effort to further elucidate how hGDF-15 inhibitors can increase the percentage of CD8+ T lymphocytes in the solid cancers, the inventors have found that hGDF-15 decreases adhesion of T cells to endothelial cells. Therefore, according to the invention, a treatment with hGDF-15 inhibitors can be used to increase adhesion of T cells including CD8+ T cells to endothelial cells. Such treatment according to the invention will increase entry of CD8+ T cells from the blood stream into solid cancers. The increased percentage of CD8+ T cells in solid cancers, which will result from such treatment with hGDF-15 inhibitors, is advantageous for, and can be used in, cancer therapy, e.g. cancer immunotherapy. Since the entry of CD8+ T cells into solid cancers and the presence of these CD8+ T cells in the solid cancers is particularly advantageous for therapeutic approaches using immune checkpoint blockers, a particularly advantageous use of hGDF-15 inhibitors according to the invention is their use in combination with immune checkpoint blockers.

Thus, the present invention provides improved means for cancer therapy by providing the preferred embodiments described below:

1. An hGDF-15 inhibitor for use in a method for increasing the percentage of CD8+ T-cells in a solid cancer in a human patient, wherein the hGDF-15 inhibitor is to be administered to the human patient.
2. The hGDF-15 inhibitor for use according to item 1, wherein the patient is a patient who has a hGDF-15 serum level of at least 1.2 ng/ml prior to the start of administration of the hGDF-15 inhibitor, wherein the patient is preferably a patient who has a hGDF-15 serum level of at least 1.5 ng/ml prior to the start of administration of the hGDF-15 inhibitor, and wherein the patient is more preferably a patient who has a hGDF-15 serum level of at least 1.8 ng/ml prior to the start of administration of the hGDF-15 inhibitor.
3. The hGDF-15 inhibitor for use according to any one of items 1 to 2, wherein the cancer is selected from the group consisting of melanoma, colorectal cancer, prostate cancer, head and neck cancer, urothelial cancer, stomach cancer, pancreatic cancer, liver cancer, testis cancer, ovarian cancer, endometrial cancer, cervical cancer, brain cancer, breast cancer, gastric cancer, renal cell carcinoma, Ewing's sarcoma, non-small cell lung cancer and small cell lung cancer, wherein the cancer is preferably selected from the group consisting of melanoma, colorectal cancer, prostate cancer, head and neck cancer, urothelial cancer, stomach cancer, pancreatic cancer, liver cancer, testis cancer, ovarian cancer, endometrial cancer and cervical cancer, and wherein the cancer is more preferably selected from the group consisting of melanoma, colorectal cancer, prostate cancer, head and neck cancer, urothelial cancer and stomach cancer.
4. The hGDF-15 inhibitor for use according to any one of the preceding items, wherein the cancer is selected from the group consisting of melanoma, oral squamous cell carcinoma, colorectal cancer and prostate cancer.
5. The hGDF-15 inhibitor for use according to any one of the preceding items, wherein the cancer is melanoma.
6. The hGDF-15 inhibitor for use according to any of the preceding items, wherein the inhibitor is a monoclonal antibody capable of binding to hGDF-15, or an antigen-binding portion thereof.
7. The hGDF-15 inhibitor for use according to item 6, wherein the binding is binding to a conformational or discontinuous epitope on hGDF-15, and wherein the conformational or discontinuous epitope is comprised by the amino acid sequences of SEQ ID No: 25 and SEQ ID No: 26.
8. The hGDF-15 inhibitor for use according to item 6 or 7, wherein the antibody or antigen-binding portion thereof comprises a heavy chain variable domain which comprises a CDR1 region comprising the amino acid sequence of SEQ ID NO: 3, a CDR2 region comprising the amino acid sequence of SEQ ID NO: 4 and a CDR3 region comprising the amino acid sequence of SEQ ID NO: 5, and wherein the antibody or antigen-binding portion thereof comprises a light chain variable domain which comprises a CDR1 region comprising the amino acid sequence of SEQ ID NO: 6, a CDR2 region comprising the amino acid sequence ser-ala-ser and a CDR3 region comprising the amino acid sequence of SEQ ID NO: 7.
9. The hGDF-15 inhibitor for use according to any of items 1 to 5, wherein the inhibitor is a short interfering RNA or an siRNA hairpin construct.
10. The hGDF-15 inhibitor for use according to any one of the preceding items, wherein the method is a method for the treatment of cancer.
11. The hGDF-15 inhibitor for use according to item 10, wherein the method for the treatment of cancer is a method for the treatment of cancer by cancer immunotherapy.
12. The hGDF-15 inhibitor for use according to any of the preceding items, wherein the method is a method for the treatment of cancer metastases.
13. The hGDF-15 inhibitor for use according to any of the preceding items, wherein the hGDF-15 inhibitor increases the percentage of CD8+ T-cells in the cancer by increasing the adhesion of CD8+ T-cells to endothelial cells and thereby increasing entry of the CD8+ T-cells from the blood stream into the cancer.
14. The hGDF-15 inhibitor for use according to any of the preceding items, wherein the use is a use in combination with an immune checkpoint blocker.
15. The hGDF-15 inhibitor for use according to any of the preceding items, wherein the immune checkpoint blocker is selected from one or more of the following group consisting of:
   i) an inhibitor of human PD-1, the inhibitor preferably being a monoclonal antibody capable of binding to human PD-1, or an antigen-binding portion thereof; and
   ii) an inhibitor of human PD-L1, the inhibitor preferably being a monoclonal antibody capable of binding to human PD-L1, or an antigen-binding portion thereof.
16. The hGDF-15 inhibitor for use according to item 15, wherein the immune checkpoint blocker comprises a monoclonal antibody capable of binding to human PD-1, or an antigen-binding portion thereof.
17. The hGDF-15 inhibitor for use according to item 15 or 16, wherein the immune checkpoint blocker comprises a monoclonal antibody capable of binding to human PD-L1, or an antigen-binding portion thereof.
18. A composition comprising an hGDF-15 inhibitor and an immune checkpoint blocker.
19. The composition according to item 18, wherein the hGDF-15 inhibitor is as defined in any one of items 6 to 9.

20. The composition according to item 18 or 19, wherein the immune checkpoint blocker is as defined in any one of items 15 to 17.
21. The composition according to any one of items 18 to 20, for use in medicine.
22. A kit comprising an hGDF-15 inhibitor and at least one immune checkpoint blocker.
23. The kit according to item 22, wherein the hGDF-15 inhibitor is as defined in any one of items 6 to 9.
24. The kit according to item 22 or 23, wherein the immune checkpoint blocker is as defined in any one of items 15 to 17.
25. The kit according to any of the preceding items, wherein the hGDF-15 inhibitor and one or more or all of the immune checkpoint blockers are contained in separate containers or in a single container.
26. The kit or the composition for use in medicine according to any one of items 21 to 25, for use in a method for treating a solid cancer.
27. The kit or the composition for use in medicine according to item 26, wherein the method is a method for cancer immunotherapy.
28. The kit or the composition for use in medicine according to item 27, wherein the cancer is as defined in item 3, 4 or 5.
29. An hGDF-15 inhibitor for use in a method of treating a solid cancer by an immune checkpoint blocker in a human patient, wherein the hGDF-15 inhibitor is to be administered to the human patient.
30. The hGDF-15 inhibitor for use according to item 29, wherein the method is a method for cancer immunotherapy.
31. The hGDF-15 inhibitor for use according to item 29 or 30, wherein the patient is as defined in item 2.
32. The hGDF-15 inhibitor for use according to any one of items 29 to 31, wherein the cancer is as defined in items 3, 4 or 5.
33. The hGDF-15 inhibitor for use according to any one of items 29 to 32, wherein the hGDF-15 inhibitor is as defined in any one of items 6 to 9.
34. The hGDF-15 inhibitor for use according to any one of items 29 to 33, wherein the immune checkpoint blocker is as defined in any one of items 15 to 17.
35. The hGDF-15 inhibitor for use according to any one of items 29 to 34, wherein the hGDF-15 inhibitor increases the percentage of CD8$^+$ T-cells in the cancer.
36. The hGDF-15 inhibitor for use according to item 35, wherein the hGDF-15 inhibitor increases the percentage of CD8$^+$ T-cells in the cancer by increasing the adhesion of CD8$^+$ T-cells to endothelial cells or the rolling of CD8$^+$ T cells on endothelial cells and thereby increasing entry of the CD8$^+$ T-cells from the blood stream into the cancer.
37. A combination of an hGDF-15 inhibitor and an immune checkpoint blocker for use in a method of treating a solid cancer in a human patient, wherein the hGDF-15 inhibitor and the immune checkpoint blocker are to be administered to the human patient.
38. The combination of the hGDF-15 inhibitor and the immune checkpoint blocker for use according to item 36, wherein the method is a method for cancer immunotherapy.
39. The combination of the hGDF-15 inhibitor and the immune checkpoint blocker for use according to any one of the preceding items, wherein the patient is as defined in item 2.
40. The combination of the hGDF-15 inhibitor and the immune checkpoint blocker for use according to any one of the preceding items, wherein the cancer is as defined in items 3, 4 or 5.
41. The combination of the hGDF-15 inhibitor and the immune checkpoint blocker for use according to any one of the preceding items, wherein the hGDF-15 inhibitor is as defined in any one of items 6 to 9.
42. The combination of the hGDF-15 inhibitor and the immune checkpoint blocker for use according to any one of the preceding items, wherein the immune checkpoint blocker is as defined in any one of items 15 to 17.
43. The combination of the hGDF-15 inhibitor and the immune checkpoint blocker for use according to any one of the preceding items, wherein the hGDF-15 inhibitor increases the percentage of CD8$^+$ T-cells in the cancer.
44. The combination of the hGDF-15 inhibitor and the immune checkpoint blocker for use according to item 43, wherein the hGDF-15 inhibitor increases the percentage of CD8$^+$ T-cells in the solid cancer by increasing the adhesion of CD8$^+$ T-cells to endothelial cells, thereby increasing entry of the CD8$^+$ T-cells from the blood stream into the solid cancer,
and wherein preferably, said increase in adhesion of CD8$^+$ T-cells to endothelial cells increases the rolling of CD8$^+$ T cells on endothelial cells such that said entry of the CD8$^+$ T-cells from the blood stream into the solid cancer is increased.
45. An in vitro method for determining whether a substance of interest is an hGDF-15 inhibitor, the method comprising:
a) activating endothelial cells;
b) incubating a first sample comprising T-cells in the presence of a solution comprising hGDF-15 and in the presence of the substance of interest;
c) measuring the adhesion of endothelial cells activated in step a) to said T-cells from said first sample to obtain a first adhesion measurement result; and
d) determining, based on the first adhesion measurement result of step c), whether the substance of interest is an hGDF-15 inhibitor.
46. The method of item 45, wherein the endothelial cells are Human Umbilical Vein Endothelial Cells.
47. The method according to any one of the preceding items, wherein the endothelial cells are human endothelial cells.
48. The method according to any one of the preceding items, wherein the endothelial cells are activated by TNF-α and IFN-γ and wherein in the activating step, TNF-α and IFN-γ are preferably present at a final concentration of 5-20 ng/ml TNF-α and 5-20 ng/ml IFN-γ in the medium, more preferably at a final concentration of 10 ng/ml TNF-α and 10 ng/ml IFN-γ in the medium.
49. The method according to any one of the preceding items, wherein the substance of interest is a substance capable of binding to hGDF-15, preferably an antibody capable of binding to hGDF-15 or an antigen-binding fragment thereof.
50. The method according to any one of the preceding items, wherein in step c), said endothelial cells and said T-cells are used in a numeric ratio of 1:2 to 2:1, preferably in a numeric ratio of 1:1.
51. The method according to any one of the preceding items, wherein during step c), the endothelial cells are present on a coated cell culture surface, preferably on a fibronectin-coated cell culture surface.

52. The method according to any one of the preceding items, wherein during step b), hGDF-15 is present at a concentration of 50 to 200 ng/ml, preferably at a concentration of 100 ng/ml.
53. The method according to any one of the preceding items, wherein in step c), adhesion is measured by counting the number of rolling T-cells.
54. The method according to any one of the preceding items, wherein in step c), adhesion is measured by counting the number of adhering T-cells.
55. The method according to any one of the preceding items, wherein in step c), adhesion is measured by measuring the rolling speed of the T-cells.
56. The method according to any one of the preceding items, wherein in step d), the substance of interest is determined to be an hGDF-15 inhibitor if it increases said adhesion.
57. The method according to any one of the preceding items, wherein in step d), the substance of interest is determined not to be an hGDF-15 inhibitor if it does not increase said adhesion.
58. The method according to any one of the preceding items, wherein in step b), a second sample is incubated in the presence of said solution comprising hGDF-15 and in the absence of said substance of interest, the second sample comprising T-cells,
    wherein step c) further comprises measuring the adhesion of endothelial cells activated in step a) to said T-cells from said second sample to obtain a second adhesion measurement result, and
    wherein in step d), the substance of interest is determined to be an hGDF-15 inhibitor if said first adhesion measurement result is increased compared to said second adhesion measurement result.
59. The method according to any one of the preceding items, wherein in step b), a third sample is incubated in the absence of said solution comprising hGDF-15 and in the absence of said substance of interest, the third sample comprising T-cells,
    wherein step c) further comprises measuring the adhesion of endothelial cells activated in step a) to said T-cells from third second sample to obtain a third adhesion measurement result, and
    wherein in step d), the third adhesion measurement result is used as a reference adhesion measurement result indicating complete hGDF-15 inhibition.
60. The method according to any one of the preceding items, wherein the T-cells are $CD8^+$ T-cells.
61. The method according to any one of items 45-59, wherein the T-cells are pan T-cells.
62. The method according to any one of the preceding items, wherein the T-cells are human T-cells.
63. The hGDF-15 inhibitor for use according to any one of items 1-17, wherein the use is a use in combination with polyinosinic:polycytidylic acid, or the combination of the hGDF-15 inhibitor and the immune checkpoint blocker for use according to any one of items 37-44, wherein the combination is a combination with polyinosinic:polycytidylic acid.
64. The hGDF-15 inhibitor for use according to any one of items 1-17 and 63, wherein the use is a use in combination with an anti-humanCD40 antibody, preferably a monoclonal anti-humanCD40 antibody, or the combination for use according to any one of items 37-44 and 63, wherein the combination is a combination with an anti-humanCD40 antibody, preferably a monoclonal anti-humanCD40 antibody.
65. A combination of an hGDF-15 inhibitor and any one of the following:
    a) polyinosinic:polycytidylic acid;
    b) an anti-humanCD40 antibody, preferably a monoclonal anti-humanCD40 antibody; or
    c) polyinosinic:polycytidylic acid and an anti-humanCD40 antibody, preferably a monoclonal anti-humanCD40 antibody,
    for use in a method of treating a solid cancer in a human patient, wherein the combination optionally comprises an immune checkpoint blocker.

BRIEF DESCRIPTION OF THE DRAWINGS

FIG. 5A: Probability of response to treatment (responder 1) as predicted by the Generalized Linear Model model using LDH as continuous predictor. Circles show the data, the curve shows the model. The vertical line indicates the LDF concentration where the probability of treatment response is 0.5. The patient cohort was identical. However, reliable determination of LDH levels failed in four patients due to hemolysis. FIG. 5B: Graphical representation of responders and non-responders and their respective hGDF-15 and LDH levels. When cut-off values are selected to cover all responders, testing based on GDF-15 allows for identification of 6 (out of 9) non-responders whereas analyses based on LDH levels can only discriminate 4 (out of 9) non-responders. For LDH testing, 4 hemolytic samples had to be excluded which causes loss of data.

FIG. 9A shows the number of rolling T cells per field of view per second. Data were obtained from channel #3 ("GDF-15") and channel #2 ("control"). FIG. 9B shows the rolling speed of the T cells (measured in pixels per 0.2 seconds). Data were obtained from channel #3 ("GDF- 15") and channel #2 ("control"). FIG. 9C shows the number of adhering cells per field of view. Data were obtained from channel #3 ("GDF-15") and channel #2 ("control"). FIG. 9D shows the number of adhering cells per field of view. Data were obtained from channel #3 ("GDF-15") and channel #2 ("control").

FIG. 10A shows the number of rolling T cells per field of view per second. Data were obtained from channel #1 (control T cells on unstimulated HUVEC as "neg. control"), channel #2 (control T cells on stimulated HUVEC as "pos. control"), channel #3 ("GDF-15") channel #4 ("UACC 257": T cells cultured in the supernatant of UACC 257 melanoma cells containing secreted GDF-15) and channel #5 ("UACC257+
anti-hGDF-15": T cells cultured in the supernatant of UACC 257 melanoma cells depleted from secreted GDF-15 with the anti-hGDF-15 antibody B1-23 as an hGDF-15 inhibitor).
FIG. 10B: The flow/adhesion assay was conducted as described in Example 3. T-cells were pre-incubated with 100 ng/ml GDF-15 for 1 hour or with 100 ng/ml GDF-15, which was pre-incubated with 10 µg/ml antibody for 1 hour, as indicated. The following Anti-GDF-15 antibodies were used: H1L5 (Humanized B1-23), 01G06 and 03G05 (Humanized Anti-GDF-15 Antibodies Engineered According to Sequences from WO 2014/100689). The results are shown in the Figure, which shows the number of rolling cells per field of view per 20 seconds.

hGDF-15 mRNA levels in samples from cancer patients were plotted against the number of somatic mutations which were identified in the cancers. The somatic mutations were determined by use of exome sequencing. The data were analyzed by using the UZH webtool from the University Hospital Zurich (Cheng P F et al.: Data mining The Cancer Genome Atlas in the era of precision cancer medicine. Swiss Med Wkly. 2015 Sep. 16; 145:w14183). FIG. 14A shows a plot for cancer patient data obtained from the Cancer Genome Atlas (TGCA) considering only patients with high-grade malignant melanoma (the Cancer Genome Atlas is described in the reference of Cheng P F et al.: Data mining The Cancer Genome Atlas in the era of precision cancer medicine. Swiss Med Wkly. 2015 Sep. 16; 145:w14183). GDF-15 expression was evaluated by normalization using the RSEM ("RNA Seq by expectation maximization") software package (Li B and Dewey C N: RSEM: accurate transcript quantification from RNA-Seq data with or without a reference genome. BMC Bioinformatics. 2011 Aug. 4; 12:323. doi: 10.1186/1471-2105-12-323). FIG. 14B shows a plot for cancer patient data from 40 additional metastatic malignant melanoma patients from the University Hospital Zurich, which were separately analyzed.

DETAILED DESCRIPTION OF THE INVENTION

Definitions and General Techniques

Figure 1:
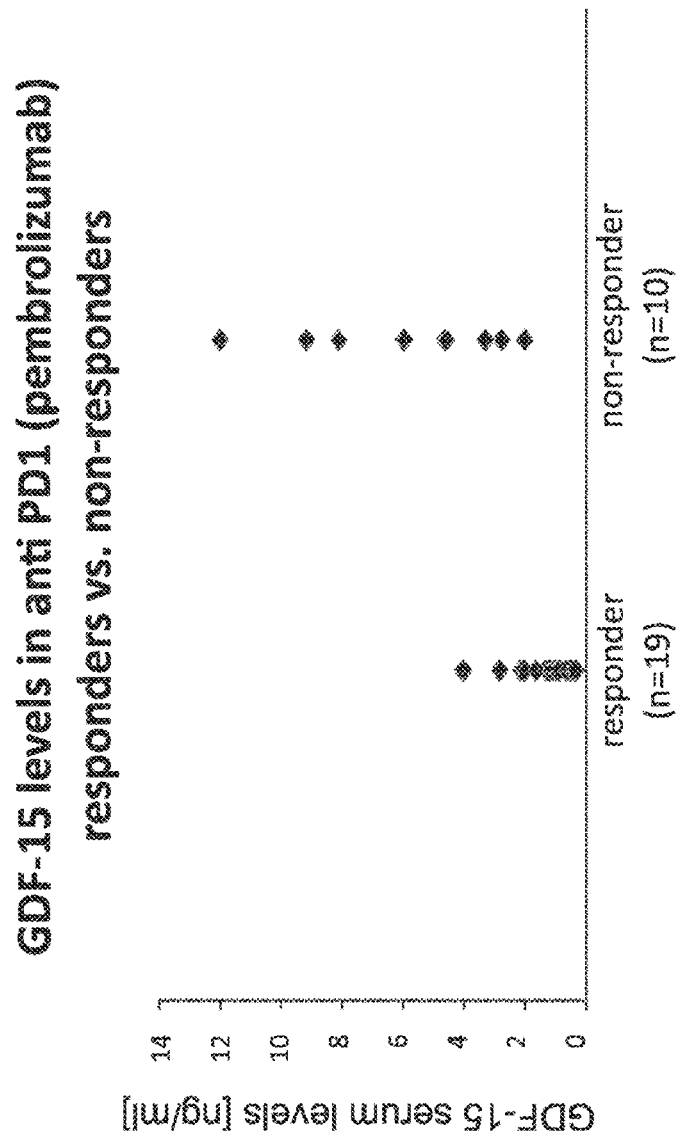
FIG. 1: This Figure shows the GDF-15 serum levels for responders and non-responders to the treatment regimen.

Unless otherwise defined below, the terms used in the present invention shall be understood in accordance with their common meaning known to the person skilled in the art.

The term "antibody" as used herein refers to any functional antibody that is capable of specific binding to the antigen of interest, as generally outlined in chapter 7 of Paul, W. E. (Ed.).: Fundamental Immunology 2nd Ed. Raven Press, Ltd., New York 1989, which is incorporated herein by reference. Without particular limitation, the term "antibody" encompasses antibodies from any appropriate source species, including chicken and mammalian such as mouse, goat, non-human primate and human. Preferably, the antibody is a humanized antibody. The antibody is preferably a monoclonal antibody which can be prepared by methods well-known in the art. The term "antibody" encompasses an IgG-1, -2, -3, or -4, IgE, IgA, IgM, or IgD isotype antibody. The term "antibody" encompasses monomeric antibodies (such as IgD, IgE, IgG) or oligomeric antibodies (such as IgA or IgM). The term "antibody" also encompasses—without particular limitations—isolated antibodies and modified antibodies such as genetically engineered antibodies, e.g. chimeric antibodies.

The nomenclature of the domains of antibodies follows the terms as known in the art. Each monomer of an antibody comprises two heavy chains and two light chains, as generally known in the art. Of these, each heavy and light chain comprises a variable domain (termed $V_H$ for the heavy chain and $V_L$ for the light chain) which is important for antigen binding. These heavy and light chain variable domains comprise (in an N-terminal to C-terminal order) the regions FR1, CDR1, FR2, CDR2, FR3, CDR3, and FR4 (FR, framework region; CDR, complementarity determining region which is also known as hypervariable region). The identification and assignment of the above-mentioned antibody regions within the antibody sequence is generally in accordance with Kabat et al. (Sequences of proteins of immunological interest, U.S. Dept. of Health and Human Services, Public Health Service, National Institutes of Health, Bethesda, Md. 1983), or Chothia et al. (Conformations of immunoglobulin hypervariable regions. Nature. 1989 Dec. 21-28; 342(6252):877-83), or may be performed by using the IMGT/V-QUEST software described in Giudicelli et al. (IMGTN-QUEST, an integrated software program for immunoglobulin and T cell receptor V-J and V-D-J rearrangement analysis. Nucleic Acids Res. 2004 Jul. 1; 32(Web Server issue):W435-40), which is incorporated herein by reference. Preferably, the antibody regions indicated above are identified and assigned by using the IMGTN-QUEST software.

A "monoclonal antibody" is an antibody from an essentially homogenous population of antibodies, wherein the antibodies are substantially identical in sequence (i.e. identical except for minor fraction of antibodies containing naturally occurring sequence modifications such as amino acid modifications at their N- and C-termini). Unlike polyclonal antibodies which contain a mixture of different antibodies directed to numerous epitopes, monoclonal antibodies are directed to the same epitope and are therefore highly specific. The term "monoclonal antibody" includes (but is not limited to) antibodies which are obtained from a monoclonal cell population derived from a single cell clone, as for instance the antibodies generated by the hybridoma method described in Kohler and Milstein (Nature, 1975 Aug. 7; 256(5517):495-7) or Harlow and Lane ("Antibodies: A Laboratory Manual" Cold Spring Harbor Laboratory Press, Cold Spring Harbor, N.Y. 1988). A monoclonal antibody may also be obtained from other suitable methods, including phage display techniques such as those described in Clackson et al. (Nature. 1991 Aug. 15; 352(6336):624-8) or Marks et al. (J Mol Biol. 1991 Dec. 5; 222(3):581-97). A monoclonal antibody may be an antibody that has been optimized for antigen-binding properties such as decreased Kd values, optimized association and dissociation kinetics by methods known in the art. For instance, Kd values may be optimized by display methods including phage display, resulting in affinity-matured monoclonal antibodies. The term "monoclonal antibody" is not limited to antibody sequences from particular species of origin or from one single species of origin. Thus, the meaning of the term "monoclonal antibody" encompasses chimeric monoclonal antibodies such as humanized monoclonal antibodies.

"Humanized antibodies" are antibodies which contain human sequences and a minor portion of non-human sequences which confer binding specificity to an antigen of interest (e.g. human GDF-15). Typically, humanized antibodies are generated by replacing hypervariable region sequences from a human acceptor antibody by hypervariable region sequences from a non-human donor antibody (e.g. a mouse, rabbit, rat donor antibody) that binds to an antigen of interest (e.g. human GDF-15). In some cases, framework region sequences of the acceptor antibody may also be replaced by the corresponding sequences of the donor antibody. In addition to the sequences derived from the donor and acceptor antibodies, a "humanized antibody" may either contain other (additional or substitute) residues or sequences or not. Such other residues or sequences may serve to further improve antibody properties such as binding properties (e.g. to decrease Kd values) and/or immunogenic properties (e.g. to decrease antigenicity in humans). Non-limiting examples for methods to generate humanized antibodies are known in the art, e.g. from Riechmann et al. (Nature. 1988 Mar. 24; 332(6162):323-7) or Jones et al. (Nature. 1986 May 29-Jun. 4; 321(6069):522-5).

The term "human antibody" relates to an antibody containing human variable and constant domain sequences. This definition encompasses antibodies having human sequences bearing single amino acid substitutions or modifications which may serve to further improve antibody properties such as binding properties (e.g. to decrease Kd values) and/or immunogenic properties (e.g. to decrease antigenicity in humans). The term "human antibody" excludes humanized antibodies where a portion of non-human sequences confers binding specificity to an antigen of interest.

An "antigen-binding portion" of an antibody as used herein refers to a portion of an antibody that retains the capability of the antibody to specifically bind to the antigen (e.g. hGDF-15, PD-1 or PD-L1). This capability can, for instance, be determined by determining the capability of the antigen-binding portion to compete with the antibody for specific binding to the antigen by methods known in the art.

The antigen-binding portion may contain one or more fragments of the antibody. Without particular limitation, the antigen-binding portion can be produced by any suitable method known in the art, including recombinant DNA methods and preparation by chemical or enzymatic fragmentation of antibodies. Antigen-binding portions may be Fab fragments, F(ab') fragments, F(ab')$_2$ fragments, single chain antibodies (scFv), single-domain antibodies, diabodies or any other portion(s) of the antibody that retain the capability of the antibody to specifically bind to the antigen.

An "antibody" (e.g. a monoclonal antibody) or an "antigen-binding portion" may have been derivatized or be linked to a different molecule. For example, molecules that may be linked to the antibody are other proteins (e.g. other antibodies), a molecular label (e.g. a fluorescent, luminescent, colored or radioactive molecule), a pharmaceutical and/or a toxic agent. The antibody or antigen-binding portion may be linked directly (e.g. in form of a fusion between two proteins), or via a linker molecule (e.g. any suitable type of chemical linker known in the art).

As used herein, the terms "binding" or "bind" refer to specific binding to the antigen of interest (e.g. human GDF-15). Preferably, the Kd value is less than 100 nM, more preferably less than 50 nM, still more preferably less than 10 nM, still more preferably less than 5 nM and most preferably less than 2 nM.

As used herein, an antibody or antigen-binding portion thereof which is "capable to compete" with a second antibody capable of binding to human GDF-15 means that said (first) antibody or antigen-binding portion thereof which is "capable to compete" is capable to reduce the binding of a 10 nM reference solution of the second antibody to human or recombinant human GDF-15 by 50%. Generally, "capable to compete" means that the concentration of the (first) antibody or antigen-binding portion thereof that is needed in order to reduce the binding of the 10 nM reference solution of the second antibody to human or recombinant human GDF-15 by 50% is less than 1000 nM, preferably less than 100 nM and more preferably less than 10 nM. The binding is measured by surface plasmon resonance measurements or by Enzyme-linked Immunosorbent assay (ELISA) measurements, preferably by surface plasmon resonance measurements.

The term "epitope" as used herein refers to a small portion of an antigen that forms the binding site for an antibody.

In the context of the present invention, binding or competitive binding of antibodies or their antigen-binding portions to the antigen of interest (e.g. human GDF-15) is preferably measured by using surface plasmon resonance measurements as a reference standard assay, as described below.

The terms "$K_D$" or "$K_D$ value" relate to the equilibrium dissociation constant as known in the art. In the context of the present invention, these terms relate to the equilibrium dissociation constant of an antibody with respect to a particular antigen of interest (e.g. human GDF-15) The equilibrium dissociation constant is a measure of the propensity of a complex (e.g. an antigen-antibody complex) to reversibly dissociate into its components (e.g. the antigen and the antibody). For the antibodies according to the invention, $K_D$ values (such as those for the antigen human GDF-15) are preferably determined by using surface plasmon resonance measurements as described below.

An "isolated antibody" as used herein is an antibody that has been identified and separated from the majority of components (by weight) of its source environment, e.g. from the components of a hybridoma cell culture or a different cell culture that was used for its production (e.g. producer cells such as CHO cells that recombinantly express the antibody). The separation is performed such that it sufficiently removes components that may otherwise interfere with the suitability of the antibody for the desired applications (e.g. with a therapeutic use of the anti-human GDF-15 antibody according to the invention). Methods for preparing isolated antibodies are known in the art and include Protein A chromatography, anion exchange chromatography, cation exchange chromatography, virus retentive filtration and ultrafiltration. Preferably, the isolated antibody preparation is at least 70% pure (w/w), more preferably at least 80% pure (w/w), still more preferably at least 90% pure (w/w), still more preferably at least 95% pure (w/w), and most preferably at least 99% pure (w/w), as measured by using the Lowry protein assay.

A "diabody" as used herein is a small bivalent antigen-binding antibody portion which comprises a heavy chain variable domain linked to a light chain variable domain on the same polypeptide chain linked by a peptide linker that is too short to allow pairing between the two domains on the same chain. This results in pairing with the complementary domains of another chain and in the assembly of a dimeric molecule with two antigen binding sites. Diabodies may be bivalent and monospecific (such as diabodies with two antigen binding sites for human GDF-15), or may be bivalent and bispecific (e.g. diabodies with two antigen binding sites, one being a binding site for human GDF-15, and the other one being a binding site for a different antigen). A detailed description of diabodies can be found in Holliger P et al. (""Diabodies": small bivalent and bispecific antibody fragments." Proc Natl Acad Sci USA. 1993 Jul. 15; 90(14): 6444-8).

A "single-domain antibody" (which is also referred to as "Nanobody™") as used herein is an antibody fragment consisting of a single monomeric variable antibody domain. Structures of and methods for producing single-domain antibodies are known from the art, e.g. from Holt L J et al. ("Domain antibodies: proteins for therapy." Trends Biotechnol. 2003 November; 21(11):484-90), Saerens D et al. ("Single-domain antibodies as building blocks for novel therapeutics." Curr Opin Pharmacol. 2008 October; 8(5): 600-8. Epub 2008 Aug. 22), and Arbabi Ghahroudi M et al. ("Selection and identification of single domain antibody fragments from camel heavy-chain antibodies." FEBS Lett. 1997 Sep. 15; 414(3):521-6).

The terms "cancer" and "cancer cell" is used herein in accordance with their common meaning in the art (see for instance Weinberg R. et al.: The Biology of Cancer. Garland Science: New York 2006. 850p).

The cancers to the treated according to the present invention are solid cancers. A "solid cancer" is a cancer which forms one or more solid tumors. Such solid cancers forming solid tumors are generally known in the art. The term "solid cancer" encompasses both a primary tumor formed by the cancer and possible secondary tumors, which are also known as metastases. Preferred solid cancers to be treated according to the invention are selected from the group consisting of melanoma, colorectal cancer, prostate cancer, head and neck cancer, urothelial cancer, stomach cancer, pancreatic cancer, liver cancer, testis cancer, ovarian cancer, endometrial cancer, cervical cancer, brain cancer, breast cancer, gastric cancer, renal cell carcinoma, Ewing's sarcoma, non-small cell lung cancer and small cell lung cancer, preferably selected from the group consisting of melanoma, colorectal cancer, prostate cancer, head and neck cancer, urothelial cancer, stomach cancer, pancreatic cancer, liver cancer, testis cancer, ovarian cancer, endometrial cancer and cervical cancer, more preferably selected from the group consisting of melanoma, colorectal cancer, prostate cancer, head and neck cancer, urothelial cancer and stomach cancer, and most preferably selected from the group consisting of melanoma, colorectal cancer and prostate cancer.

As referred to herein, the term "brain cancer" refers to all brain cancers known in the art. It includes but is not limited to glioma (WHO grade I to IV), astrocytoma, meningioma and medulloblastoma.

As referred to herein, the term "head and neck cancer" refers to all head and neck cancers known in the art. It includes but is not limited to oesophagus carcinoma, oral squamous cell carcinoma and hypopharyngeal cancer. A particularly preferred head and neck cancer to be treated according to the invention is oral squamous cell carcinoma.

The term "cancer growth" as used herein relates to any measureable growth of the cancer. For cancers forming solid tumors, "cancer growth" relates to a measurable increase in tumor volume over time. If the cancer has formed only a single tumor, "cancer growth" relates only to the increase in volume of the single tumor. If the cancer has formed multiple tumors such as metastases, "cancer growth" relates to the increase in volume of all measurable tumors. For solid tumors, the tumor volume can be measured by any method known in the art, including magnetic resonance imaging and computed tomography (CT scan).

Terms such as "treatment of cancer" or "treating cancer" according to the present invention refer to a therapeutic treatment. An assessment of whether or not a therapeutic treatment works can, for instance, be made by assessing whether the treatment inhibits cancer growth in the treated patient or patients. Preferably, the inhibition is statistically significant as assessed by appropriate statistical tests which are known in the art. Inhibition of cancer growth may be assessed by comparing cancer growth in a group of patients treated in accordance with the present invention to a control group of untreated patients, or by comparing a group of patients that receive a standard cancer treatment of the art plus a treatment according to the invention with a control group of patients that only receive a standard cancer treatment of the art. Such studies for assessing the inhibition of cancer growth are designed in accordance with accepted standards for clinical studies, e.g. double-blinded, randomized studies with sufficient statistical power. The term "treating cancer" includes an inhibition of cancer growth where the cancer growth is inhibited partially (i.e. where the cancer growth in the patient is delayed compared to the control group of patients), an inhibition where the cancer growth is inhibited completely (i.e. where the cancer growth in the patient is stopped), and an inhibition where cancer growth is reversed (i.e. the cancer shrinks). Preferably, an assessment of whether or not a therapeutic treatment works can be made based on a classification of responders and non-responders by using the response evaluation criteria in solid tumours, version 1.1 (RECIST v1.1) (Eisenhauer et al.: New response evaluation criteria in solid tumours: revised RECIST guideline (version 1.1). In: Eur. J. Cancer. 45, No. 2, January 2009, pp. 228-47). Alternatively, or additionally, an assessment of whether or not a therapeutic treatment works can be made based on known clinical indicators of cancer progression.

The treatment of cancer according to the invention can be a first-line therapy, a second-line therapy or a third-line therapy or a therapy that is beyond third-line therapy. The meaning of these terms is known in the art and in accordance with the terminology that is commonly used by the US National Cancer Institute.

A treatment of cancer according to the present invention does not exclude that additional or secondary therapeutic benefits also occur in patients. For example, an additional or secondary benefit may be an influence on cancer-induced weight loss. However it is understood that the primary treatment for which protection is sought is for treating the cancer itself, any secondary or additional effects only reflect optional, additional advantages of the treatment of cancer growth.

The term "cancer immunotherapy" is known in the art and generally relates to a treatment of cancer in which the immune system of the patient is used to treat the cancer. Cancer cells harbor genomic mutations which give rise to cancer cell antigens that are specific to the cancer cells and different from the antigens of non-cancerous cells. Thus, in a preferred aspect of cancer immunotherapy in accordance with the present invention, a cancer immunotherapy is a cancer immunotherapy wherein such cancer cell antigens are recognized by the immune system, and wherein cancer cells expressing these antigens are killed by the immune system. In a non-limiting aspect of the invention, such cancer cells expressing these cancer cell antigens can be killed by $CD8^+$ T-cells of the immune system. A cancer immunotherapy can be assessed by immunomonitoring methods known in the art, e.g. by measuring intracellular IFN-γ expression (e.g. in $CD8^+$ T-cells and/or NK cells) in blood samples, measuring CD107a cell surface expression (e.g. on $CD8^+$ T-cells and/or NK cells) in blood samples, measuring intracellular TNF-α expression (e.g. on leukocytes) in blood samples, intracellular Interleukin-2 expression (e.g. in $CD8^+$ T-cells and/or in $CD4^+$ T-cells) in blood samples, CD154 cell surface expression (e.g. in $CD8^+$ T-cells and/or in $CD4^+$ T-cells) in blood samples, tetramer or dextramer staining for tumor antigen-specific T cells in blood samples, CTL activity against autologous tumor cells or presence of T cells against neoantigens derived from tumor-specific mutations. Preferred methods to assess cancer immunotherapy are the methods according to Gouttefangeas C et al.: "Flow Cytometry in Cancer Immunotherapy: Applications, Quality Assurance and Future." (2015) In: Cancer Immunology: Translational Medicine from Bench to Bedside (N. Rezaei editor). Springer. Chapter 25: pages 471-486; and the methods according to Van der Burg S H, et al.: "Immunoguiding, the final frontier in the immunotherapy of cancer." (2014) In Cancer Immunotherapy meets oncology (C M Britten, S Kreiter, M. Diken & HG Rammensee eds). Springer International Publishing Switzerland p37-51 ISBN: 978-3-319-05103-1.

As used herein, a "cancer immunotherapy" optionally encompasses a treatment where in addition to the immune system which is used to treat the cancer, additional mechanisms of cancer treatment are used. For instance, it was previously shown that a hGDF-15 inhibitor can be used for cancer treatment in an mouse model system where the immune system was severely compromised (WO 2014/049087). Thus, according to the present invention, a cancer immunotherapy by hGDF-15 inhibitors in human patients can also encompass additional treatment effects of hGDF-15 inhibitors which are independent from the immune system. Another example of a cancer immunotherapy where additional mechanisms of cancer treatment can be used is a combination therapy with known chemotherapeutic agent(s). Such combination therapy with known chemotherapeutic agent(s) may, for instance, not only include the treatment of cancer in which the immune system is used to treat the cancer but also include a treatment of cancer in which the cancer cells are killed by said chemotherapeutic agent(s) directly.

As used herein, the term "increasing the percentage of $CD8^+$ T-cells in a solid cancer" relates to any measurable increase in the percentage of $CD8^+$ T-cells (i.e. the percentage of $CD8^+$ T-cells calculated with respect to all cells) in the tumor or tumors formed by the solid cancer. Preferably, the increase is statistically significant as assessed by appropriate statistical tests which are known in the art. An increase in the percentage of $CD8^+$ T-cells in the tumor or tumors formed by the solid cancer can be determined by known methods for analyses of $CD8^+$ T-cells in solid tumors. Such methods include analyses of tumor biopsies for $CD8^+$ T-cells, e.g. analyses of such tumor biopsies by immunohistochemistry using antibodies against CD8 and using a staining for the total number of cells. The increase may be assessed by comparing the percentages of $CD8^+$ T-cells in tumors of a group of patients treated in accordance with the present invention to a control group of untreated patients, or by comparing a group of patients that receive a standard cancer treatment of the art plus a treatment according to the invention with a control group of patients that only receive a standard cancer treatment of the art.

As used herein, "$CD8^+$ T-cells" are preferably cells which endogenously occur in the human patient.

hGDF-15 serum levels can be measured by any methods known in the art. For instance, a preferred method of measuring hGDF-15 serum levels is a measurement of hGDF-15 serum levels by Enzyme-Linked Immunosorbent Assay (ELISA) by using antibodies to GDF-15. Such ELISA methods are exemplified in Example 1. Alternatively, hGDF-15 serum levels may be determined by known electrochemiluminesence immunoassays using antibodies to GDF-15. For instance, the Roche Elecsys® technology can be used for such electrochemiluminesence immunoassays.

The patient to be treated according to the invention is preferably a patient with elevated hGDF-15 serum levels. The term "elevated hGDF-15 serum levels" as used herein means that the human patient has higher hGDF-15 levels in blood serum prior to administration of the hGDF-15 inhibitor according to the invention, when compared to median hGDF-15 levels in blood sera of healthy human control individuals as a reference.

The median hGDF-15 serum level of healthy human control individuals is <0.8 ng/ml. The expected range is between 0.2 ng/ml and 1.2 ng/ml in healthy human controls (Reference: Tanno T et al.: "Growth differentiation factor 15 in erythroid health and disease." Curr Opin Hematol. 2010 May; 17(3): 184-190).

Thus, in a preferred embodiment of the invention, a patient to be treated according to the invention is a patient who has a hGDF-15 serum level of at least 1.2 ng/ml prior to the start of administration of the hGDF-15 inhibitor, preferably a patient who has a hGDF-15 serum level of at least 1.5 ng/ml prior to the start of administration of the hGDF-15 inhibitor, and more preferably a patient who has a hGDF-15 serum level of at least 1.8 ng/ml prior to the start of administration of the hGDF-15 inhibitor.

In a further preferred embodiment of the invention, a patient to be treated according to the invention is a patient who has a hGDF-15 serum level of at least 1.2 ng/ml and not more than 12 ng/ml prior to the start of administration of the hGDF-15 inhibitor, preferably a patient who has a hGDF-15 serum level of at least 1.5 ng/ml and not more than 12 ng/ml prior to the start of administration of the hGDF-15 inhibitor, and more preferably a patient who has a hGDF-15 serum level of at least 1.8 ng/ml and not more than 12 ng/ml prior to the start of administration of the hGDF-15 inhibitor.

In a further embodiment of the invention in accordance with all of the above embodiments, a patient to be treated according to the invention is a patient who has a hGDF-15 serum level of at least 1.2 ng/ml and not more than 10 ng/ml prior to the start of administration of the hGDF-15 inhibitor, preferably a patient who has a hGDF-15 serum level of at least 1.5 ng/ml and not more than 10 ng/ml prior to the start of administration of the hGDF-15 inhibitor, and more preferably a patient who has a hGDF-15 serum level of at least 1.8 ng/ml and not more than 10 ng/ml prior to the start of administration of the hGDF-15 inhibitor.

In a further embodiment of the invention in accordance with all of the above embodiments, a patient to be treated according to the invention is a patient who has a hGDF-15 serum level of at least 1.2 ng/ml and not more than 8 ng/ml prior to the start of administration of the hGDF-15 inhibitor, preferably a patient who has a hGDF-15 serum level of at least 1.5 ng/ml and not more than 8 ng/ml prior to the start of administration of the hGDF-15 inhibitor, and more preferably a patient who has a hGDF-15 serum level of at least 1.8 ng/ml and not more than 8 ng/ml prior to the start of administration of the hGDF-15 inhibitor.

In another embodiment, a patient to be treated according to the invention is a patient who has a hGDF-15 serum level of at least 2 ng/ml, at least 2.2 ng/ml, at least 2.4 ng/ml, at least 2.6 ng/ml, at least 2.8 ng/ml, at least 3.0 ng/ml, at least 3.2 ng/ml, at least 3.4 ng/ml, at least 3.6 ng/ml, at least 3.8 ng/ml, at least 4.0 ng/ml, or at least 4.2 ng/ml prior to the start of administration of the hGDF-15 inhibitor. In this embodiment, the patient is preferably a patient who has a hGDF-15 serum level of not more than 12 ng/ml prior to the start of administration of the hGDF-15 inhibitor. More preferably, in this embodiment, the patient is a patient who has a hGDF-15 serum level of not more than 10 ng/ml prior to the start of administration of the hGDF-15 inhibitor. Most preferably, in this embodiment, the patient is a patient who has a hGDF-15 serum level of not more than 8 ng/ml prior to the start of administration of the hGDF-15 inhibitor.

The term "prior to the start of administration" as used herein means the period of time immediately before administration of the hGDF-15 inhibitor according to the invention. Preferably, the term "prior to the start of administration" means a period of 30 days immediately before administration; most preferably a period of one week immediately before administration.

The terms "significant", "significantly", etc. as used herein refer to a statistically significant difference between values as assessed by appropriate methods known in the art.

The hGDF-15 inhibitors and the immune checkpoint blockers used according to the invention can be administered by using methods known in the art. Such methods will be selected by the skilled person based on well-known considerations, including the chemical nature of the respective inhibitor (e.g. depending on whether the inhibitor is a short interfering RNA or an antibody). Administration of known immune checkpoint blockers may be based on known administration schemes of these immune checkpoint blockers. For instance, administration of the immune checkpoint blockers may be based on the administration schemes used in the KEYNOTE-006 trial (C. Robert et al. N Engl J Med 2015; 372:2521-2532).

In accordance with the present invention, each occurrence of the term "comprising" may optionally be substituted with the term "consisting of".

hGDF-15 Inhibitors to be Used in Accordance with the Invention

An "hGDF-15 inhibitor" according to the invention can be any molecule which is capable of specifically inhibiting the function of human GDF-15 (hGDF-15).

A non-limiting example of such an hGDF-15 inhibitor is a molecule which specifically downregulates the expression of hGDF-15 and thereby inhibits hGDF-15 function. For instance, a short interfering RNA or an siRNA hairpin construct can be used to specifically downregulate the expression of hGDF-15 and to inhibit hGDF-15 function. Rules for the design and selection of short interfering RNA and siRNA hairpin construct sequences are known in the art and have for example been reviewed in Jackson and Linsley, Recognizing and avoiding siRNA off-target effects for target identification and therapeutic application, Nat Rev Drug Discov. 2010 January; 9(1):57-67. Short interfering RNAs and siRNA hairpin constructs can be delivered to the human patients by any suitable methods, including viral delivery methods (as, for instance, reviewed in Knoepfel S A et al., "Selection of RNAi-based inhibitors for anti-HIV gene therapy." World J Virol. 2012 Jun. 12; 1(3):79-90) and other delivery methods such as methods using conjugate groups which facilitate delivery into the cells (as, for instance, reviewed in Kanasty R et al., "Delivery materials for siRNA therapeutics.", Nat Mater. 2013 November; 12(11):967-77.)

Whether or not a substance of interest is a "hGDF-15 inhibitor" can be determined by using the methods disclosed herein, as detailed in the preferred embodiments. A preferred method in accordance with the preferred embodiments is the method used in Example 3.

It was previously shown that human GDF-15 protein can be advantageously targeted by a monoclonal antibody (WO2014/049087), and that such antibody has advantageous properties including a high binding affinity to human GDF-15, as demonstrated by an equilibrium dissociation constant of about 790 pM for recombinant human GDF-15 (see Reference Example 1). Thus, in a preferred embodiment in accordance with the invention, the hGDF-15 inhibitor to be used is an antibody capable of binding to hGDF-15, or an antigen-binding portion thereof. Preferably, the antibody is a monoclonal antibody capable of binding to hGDF-15, or an antigen-binding portion thereof.

Thus, in a more preferred embodiment, the hGDF-15 inhibitor in accordance with the invention is a monoclonal antibody capable of binding to human GDF-15, or an antigen-binding portion thereof, wherein the heavy chain variable domain comprises a CDR3 region comprising the amino acid sequence of SEQ ID NO: 5 or an amino acid sequence at least 90% identical thereto, and wherein the light chain variable domain comprises a CDR3 region comprising the amino acid sequence of SEQ ID NO: 7 or an amino acid sequence at least 85% identical thereto. In this embodiment, preferably, the antibody or antigen-binding portion thereof comprises a heavy chain variable domain which comprises a CDR1 region comprising the amino acid sequence of SEQ ID NO: 3 and a CDR2 region comprising the amino acid sequence of SEQ ID NO: 4, and the antibody or antigen-binding portion thereof comprises a light chain variable domain which comprises a CDR1 region comprising the amino acid sequence of SEQ ID NO: 6, and a CDR2 region comprising the amino acid sequence ser-ala-ser.

Thus, in a still more preferred embodiment, the hGDF-15 inhibitor in accordance with the invention is a monoclonal antibody capable of binding to human GDF-15, or an antigen-binding portion thereof, wherein the antibody or antigen-binding portion thereof comprises a heavy chain variable domain which comprises a CDR1 region comprising the amino acid sequence of SEQ ID NO: 3, a CDR2 region comprising the amino acid sequence of SEQ ID NO: 4 and a CDR3 region comprising the amino acid sequence of SEQ ID NO: 5, and wherein the antibody or antigen-binding portion thereof comprises a light chain variable domain which comprises a CDR1 region comprising the amino acid sequence of SEQ ID NO: 6, a CDR2 region comprising the amino acid sequence ser-ala-ser and a CDR3 region comprising the amino acid sequence of SEQ ID NO: 7.

In another embodiment in accordance with the above embodiments of the monoclonal antibody capable of binding to human GDF-15, or an antigen-binding portion thereof, the heavy chain variable domain comprises a region comprising an FR1, a CDR1, an FR2, a CDR2 and an FR3 region and comprising the amino acid sequence of SEQ ID NO: 1 or a sequence 85%, 90%, 91%, 92%, 93%, 94%, 95%, 96%, 97%, 98% or 99% identical thereto, and the light chain variable domain comprises a region comprising an FR1, a CDR1, an FR2, a CDR2 and an FR3 region and comprising the amino acid sequence of SEQ ID NO: 2 or a sequence 85%, 90%, 91%, 92%, 93%, 94%, 95%, 96%, 97%, 98% or 99% identical thereto.

In a preferred embodiment in accordance with the above embodiments of the monoclonal antibody capable of binding to human GDF-15, or an antigen-binding portion thereof, the antibody is a humanized antibody or an antigen-binding portion thereof. The constant domain of the heavy chain of this monoclonal antibody or antigen-binding portion thereof may comprise the amino acid sequence of SEQ ID No: 29, or an amino acid sequence at least 85%, preferably at least 90%, more preferably at least 95% identical thereto, and the constant domain of the light chain of this monoclonal antibody or antigen-binding portion thereof may comprise the amino acid sequence of SEQ ID No: 32, or an amino acid sequence at least 85%, preferably at least 90%, more preferably at least 95% identical thereto. More preferably, the constant domain of the heavy chain of this monoclonal antibody or antigen-binding portion thereof comprises the amino acid sequence of SEQ ID No: 29, or an amino acid sequence at least 98%, preferably at least 99% identical thereto, and the constant domain of the light chain of this monoclonal antibody or antigen-binding portion thereof comprises the amino acid sequence of SEQ ID No: 32, or an amino acid sequence at least 98%, preferably at least 99% identical thereto. Still more preferably, the constant domain of the heavy chain of this monoclonal antibody or antigen-binding portion thereof comprises the amino acid sequence of SEQ ID No: 29, and the constant domain of the light chain of this monoclonal antibody or antigen-binding portion thereof comprises the amino acid sequence of SEQ ID No: 32. The heavy chain variable domain of this monoclonal antibody or antigen-binding portion thereof may comprise the amino acid sequence of SEQ ID No: 28, or an amino acid sequence at least 90%, preferably at least 95%, more preferably at least 98%, still more preferably at least 99% identical thereto, and the light chain variable domain of this monoclonal antibody or antigen-binding portion thereof may comprise the amino acid sequence of SEQ ID No: 31, or an amino acid sequence at least 90%, preferably at least 95%, more preferably at least 98%, still more preferably at least 99% identical thereto. Most preferably, the heavy chain variable domain of this monoclonal antibody or antigen-binding portion thereof comprises the amino acid sequence of SEQ ID No: 28, and the light chain variable domain of this monoclonal antibody or antigen-binding portion thereof comprises the amino acid sequence of SEQ ID No: 31.

In another embodiment in accordance with the above embodiments of the monoclonal antibody capable of binding to human GDF-15, or an antigen-binding portion thereof, the heavy chain variable domain comprises a CDR1 region comprising the amino acid sequence of SEQ ID NO: 3 and a CDR2 region comprising the amino acid sequence of SEQ ID NO: 4, and the light chain variable domain comprises a CDR1 region comprising the amino acid sequence of SEQ ID NO: 6 and a CDR2 region comprising the amino acid sequence of SEQ ID NO: 7. In a preferred aspect of this embodiment, the antibody may have CDR3 sequences as defined in any of the embodiments of the invention described above.

In another embodiment in accordance with the monoclonal antibody capable of binding to human GDF-15, or an antigen-binding portion thereof, the antigen-binding portion is a single-domain antibody (also referred to as "Nanobody™"). In one aspect of this embodiment, the single-domain antibody comprises the CDR1, CDR2, and CDR3 amino acid sequences of SEQ ID NO: 3, SEQ ID NO: 4, and SEQ ID NO: 5, respectively. In another aspect of this embodiment, the single-domain antibody comprises the CDR1, CDR2, and CDR3 amino acid sequences of SEQ ID NO: 6, ser-ala-ser, and SEQ ID NO: 7, respectively. In a preferred aspect of this embodiment, the single-domain antibody is a humanized antibody.

Preferably, the antibodies capable of binding to human GDF-15 or the antigen-binding portions thereof have an equilibrium dissociation constant for human GDF-15 that is equal to or less than 100 nM, less than 20 nM, preferably less than 10 nM, more preferably less than 5 nM and most preferably between 0.1 nM and 2 nM.

In another embodiment in accordance with the above embodiments of the monoclonal antibody capable of binding to human GDF-15, or an antigen-binding portion thereof, the antibody capable of binding to human GDF-15 or the antigen-binding portion thereof binds to the same human GDF-15 epitope as the antibody to human GDF-15 obtainable from the cell line B1-23 deposited with the Deutsche Sammlung für Mikroorganismen and Zellkulturen GmbH (DMSZ) under the accession No. DSM ACC3142. As described herein, antibody binding to human GDF-15 in accordance with the present invention is preferably assessed by surface plasmon resonance measurements as a reference standard method, in accordance with the procedures described in Reference Example 1. Binding to the same epitope on human GDF-15 can be assessed similarly by surface plasmon resonance competitive binding experiments of the antibody to human GDF-15 obtainable from the cell line B1-23 and the antibody that is expected to bind to the same human GDF-15 epitope as the antibody to human GDF-15 obtainable from the cell line B1-23.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 39 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 40 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 41 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 42 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 43 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 44 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 45 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 46 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 47 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 48 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 49 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 50 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody capable of binding to human GDF-15, or an antigen-binding portion thereof, wherein the heavy chain variable domain comprises the amino acid sequence of SEQ ID NO: 51 or a sequence that is at least 85%, at least 90%, at least 91%, at least 92%, at least 93%, at least 94%, at least 95%, at least 96%, at least 97%, at least 98% or at least 99% identical thereto, and the light chain variable domain comprises the amino acid sequence of SEQ ID NO: 52 or a sequence that is at least 85%, at least 90%, at least 91%, at least 92%, at least 93%, at least 94%, at least 95%, at least 96%, at least 97%, at least 98% or at least 99% identical thereto.

In another preferred embodiment, the antibody capable of binding to human GDF-15 or the antigen-binding portion thereof is a monoclonal antibody or antigen-binding portion thereof, which is capable to compete with any one of the antibodies capable of binding to human GDF-15 referred to herein for binding to human GDF-15, preferably for binding to recombinant human GDF-15.

In a very preferred embodiment, the antibody capable of binding to human GDF-15 or the antigen-binding portion thereof is a humanized monoclonal antibody or an antigen-binding portion thereof. For any given non-human antibody sequence in accordance with the invention (i.e. a donor antibody sequence), humanized monoclonal anti-human-GDF-15 antibodies of the invention or antigen-binding portions thereof can be generated in accordance with techniques known in the art, as described above.

In a very preferred embodiment, the antibody capable of binding to human GDF-15 or the antigen-binding portion thereof is a monoclonal antibody capable of binding to human GDF-15, or an antigen-binding portion thereof, wherein the binding is binding to a conformational or discontinuous epitope on human GDF-15 comprised by the amino acid sequences of SEQ ID No: 25 and SEQ ID No: 26. In a preferred aspect of this embodiment, the antibody or antigen-binding portion thereof is an antibody or antigen-binding portion thereof as defined by the sequences of any one of the above embodiments.

The antibody capable of binding to human GDF-15 or the antigen-binding portion thereof can be linked to a drug. In non-limiting aspects of this embodiment, the drug can be a known anticancer agent and/or an immune-stimulatory molecule. Known anticancer agents include alkylating agents such as cisplatin, carboplatin, oxaliplatin, mechlorethamine, cyclophosphamide, chlorambucil, and ifosfamide; anti-metabolites such as azathioprine and mercaptopurine; alkaloids such as vinca alkaloids (e.g. vincristine, vinblastine, vinorelbine, and vindesine), taxanes (e.g. paclitaxel, docetaxel) etoposide and teniposide; topoisomerase inhibitors such as camptothecins (e.g. irinotecan and topotecan); cytotoxic antibiotics such as actinomycin, anthracyclines, doxorubicin, daunorubicin, valrubicin, idarubicin, epirubicin, bleomycin, plicamycin and mitomycin; and radioisotopes.

In a further embodiment in accordance with the above embodiments, the antibody capable of binding to human GDF-15 or the antigen-binding portion thereof is modified by an amino acid tag. Non-limiting examples of such tags include Polyhistidin (His-) tags, FLAG-tag, Hemagglutinin (HA) tag, glycoprotein D (gD) tag, and c-myc tag. Tags may be used for various purposes. For instance, they may be used to assist purification of the antibody capable of binding to human GDF-15 or the antigen-binding portion thereof. Preferably, such tags are present at the C-terminus or N-terminus of the antibody capable of binding to human GDF-15 or the antigen-binding portion thereof.

Immune Checkpoint Blockers to be Used in Accordance with the Invention

Cancer cells harbor genomic mutations which give rise to cancer cell antigens that are specific to the cancer cells and different from the antigens of non-cancerous cells. Therefore, an intact immune system which is not inhibited should recognize these cancer cell antigens, such that an immune response against these antigens is elicited. However, most cancers have developed immune tolerance mechanisms against these antigens. One class of mechanisms by which cancer cells achieve such immune tolerance is the utilization of immune checkpoints. An "immune checkpoint" as used herein generally means an immunological mechanism by which an immune response can be inhibited. More particularly, an immune checkpoint is a mechanism which is characterized in that a molecule of the immune system (or a group of molecules of the immune system) inhibits the immune response by inhibiting the activation of cells of the immune system. Such molecule (or group of molecules) of the immune system which inhibits (inhibit) the immune response by inhibiting the activation of cells of the immune system is (are) also known as checkpoint molecule(s).

As used herein, an "immune checkpoint blocker" is a molecule which is capable of blocking an immune checkpoint. While it is understood that an hGDF-15 inhibitor as used according to the invention has effects on the immune system including effects on CD8+ T cells, the term "immune checkpoint blocker" as used herein does not refer to an hGDF-15 inhibitor but means a molecule which is different from an hGDF-15 inhibitor.

The most common immune checkpoint blockers which are known to date are inhibitors of immune checkpoint molecules such as inhibitors of human PD-1 and inhibitors of human PD-L1. Further immune checkpoint blockers are anti-LAG-3, anti-B7H3, anti-TIM3, anti-VISTA, anti-TIGIT, anti-KIR, anti-CD27, anti-CD137 as well as inhibitors of IDO. Therefore, as used in accordance with the present invention, a preferred form of an immune checkpoint blocker is an inhibitor of an immune checkpoint molecule. Alternatively, an immune checkpoint blocker can be an activator of a co-stimulating signal which overrides the immune checkpoint.

Methods to measure the potency of immune checkpoint blockers include in vitro binding assays, primary T cell-based cytokine release assays, and in vivo model systems. Additionally, Promega has now developed a commercially available bioluminescent reporter system for PD-1/PD-L1, which is, for instance referred to in Mei Cong, Ph.D. et al.: Advertorial: Novel Bioassay to Assess PD-1/PD-L1 Therapeutic Antibodies in Development for Immunotherapy Bioluminescent Reporter-Based PD-1/PD-L1 Blockade Bioassay. (http://www.genengnews.com/gen-articles/advertorial-novel-bioassay-to-assess-pd-1-pd-11-therapeutic-antibodies-in-development-for-immun/5511/).

Preferred immune checkpoint blockers are inhibitors of human PD-1 and inhibitors of human PD-L1. In one preferred embodiment in accordance with all of the embodiments of the invention, the immune checkpoint blocker is not an inhibitor of human CTLA4.

As used herein, an "inhibitor of human PD-1" can be any molecule which is capable of specifically inhibiting the function of human PD-1. Non-limiting examples of such molecules are antibodies capable of binding to human PD-1 and DARPins (Designed Ankyrin Repeat Proteins) capable of binding to human PD-1. Preferably, the inhibitor of PD-1 to be used in accordance with the invention is an antibody capable of binding to human PD-1, more preferably a monoclonal antibody capable of binding to human PD-1. Most preferably, the monoclonal antibody capable of binding to human PD-1 is selected from the group consisting of nivolumab, pembrolizumab, pidilizumab and AMP-224.

As used herein, an "inhibitor of human PD-L1" can be any molecule which is capable of specifically inhibiting the function of human PD-L1. Non-limiting examples of such molecules are antibodies capable of binding to human PD-L1 and DARPins (Designed Ankyrin Repeat Proteins) capable of binding to human PD-L1. Preferably, the inhibitor of human PD-L1 to be used in accordance with the invention is an antibody capable of binding to human PD-L1, more preferably a monoclonal antibody capable of binding to human PD-L1. Most preferably, the monoclonal antibody capable of binding to human PD-L1 is selected from the group consisting of BMS-936559, MPDL3280A, MED14736, and MSB0010718C.

Methods and Techniques

Generally, unless otherwise defined herein, the methods used in the present invention (e.g. cloning methods or methods relating to antibodies) are performed in accordance with procedures known in the art, e.g. the procedures described in Sambrook et al. ("Molecular Cloning: A Laboratory Manual.", $2^{nd}$ Ed., Cold Spring Harbor Laboratory Press, Cold Spring Harbor, N.Y. 1989), Ausubel et al. ("Current Protocols in Molecular Biology." Greene Publishing Associates and Wiley Interscience; New York 1992), and Harlow and Lane ("Antibodies: A Laboratory Manual" Cold Spring Harbor Laboratory Press, Cold Spring Harbor, N.Y. 1988), all of which are incorporated herein by reference.

Binding of antibodies to their respective target proteins can be assessed by methods known in the art. The binding of monoclonal antibodies to their respective targets is preferably assessed by surface plasmon resonance measurements. These measurements are preferably carried out by using a Biorad ProteOn XPR36 system and Biorad GLC sensor chips, as exemplified for anti-human GDF-15 mAb-B1-23 in Reference Example 1.

Sequence Alignments of sequences according to the invention are performed by using the BLAST algorithm (see Altschul et al. (1990) "Basic local alignment search tool." Journal of Molecular Biology 215. p. 403-410; Altschul et al.: (1997) Gapped BLAST and PSI-BLAST: a new generation of protein database search programs. Nucleic Acids Res. 25:3389-3402). Preferably, the following parameters are used: Max target sequences 10; Word size 3; BLOSUM 62 matrix; gap costs: existence 11, extension 1; conditional compositional score matrix adjustment. Thus, when used in connection with sequences, terms such as "identity" or "identical" refer to the identity value obtained by using the BLAST algorithm.

Monoclonal antibodies according to the invention can be produced by any method known in the art, including but not limited to the methods referred to in Siegel D L ("Recombinant monoclonal antibody technology." Transfus Clin Biol. 2002 January; 9(1):15-22). In one embodiment, an antibody according to the invention is produced by the hybridoma cell line B1-23 deposited with the Deutsche Sammlung für Mikroorganismen und Zellkulturen GmbH (DSMZ) at Inhoffenstraße 7B, 38124 Braunschweig, Germany, under the accession No. DSM ACC3142 under the Budapest treaty. The deposit was filed on Sep. 29, 2011.

Cell proliferation can be measured by suitable methods known in the art, including (but not limited to) visual microscopy, metabolic assays such as those which measure mitochondrial redox potential (e.g. MTT (344,5-Dimethylthiazol-2-yl)-2,5-diphenyltetrazolium bromide) assay; Resazurin staining which is also known as Alamar Blue® assay), staining of known endogenous proliferation biomarkers (e.g. Ki-67), and methods measuring cellular DNA synthesis (e.g. BrdU and [$^3$H]-Thymidine incorporation assays).

Levels of human GDF-15 (hGDF-15) can be measured by any method known in the art, including measurements of hGDF-15 protein levels by methods including (but not limited to) mass spectrometry for proteins or peptides derived from human GDF-15, Western Blotting using antibodies specific to human GDF-15, flow cytometry using antibodies specific to human GDF-15, strip tests using antibodies specific to human GDF-15, or immunocytochemistry using antibodies specific to human GDF-15. A preferred method of measuring hGDF-15 serum levels is a measurement of hGDF-15 serum levels by Enzyme-Linked Immunosorbent Assay (ELISA) by using antibodies to GDF-15. Such ELISA methods are exemplified in Example 1. Alternatively, hGDF-15 serum levels may be determined by known electrochemiluminesence immunoassays using antibodies to GDF-15. For instance, the Roche Elecsys® technology can be used for such electrochemiluminesence immunoassays.

Preparation of Compositions of the Invention

Compositions in accordance with the present invention are prepared in accordance with known standards for the preparation of pharmaceutical compositions.

For instance, the compositions are prepared in a way that they can be stored and administered appropriately, e.g. by using pharmaceutically acceptable components such as carriers, excipients or stabilizers.

Such pharmaceutically acceptable components are not toxic in the amounts used when administering the pharmaceutical composition to a patient. The pharmaceutical acceptable components added to the pharmaceutical compositions may depend on the chemical nature of the inhibitors present in the composition (e.g. depend on whether the inhibitors are antibodies, si RNA hairpin constructs or short interfering RNAs), the particular intended use of the pharmaceutical compositions and the route of administration.

In general, the pharmaceutically acceptable components used in connection with the present invention are used in accordance with knowledge available in the art, e.g. from Remington's Pharmaceutical Sciences, Ed. AR Gennaro, 20th edition, 2000, Williams & Wilkins, Pa., USA.

Therapeutic Methods and Products for Use in these Methods

The present invention relates to the hGDF-15 inhibitors for the uses as defined above.

Additionally, and in accordance with these hGDF-15 inhibitors and their uses, the present invention also relates to corresponding therapeutic methods.

Accordingly, in one embodiment, the invention relates to a method for increasing the percentage of CD8$^+$ T-cells in a solid cancer in a human patient, the method comprising the step of administering an hGDF-15 inhibitor to the human patient.

In another embodiment, the invention relates to a method of treating a solid cancer by an immune checkpoint blocker in a human patient, the method comprising a step of administering an hGDF-15 inhibitor to the human patient and a step of administering the immune checkpoint blocker to the human patient.

Preferred embodiments of these methods are as defined above for the hGDF-15 inhibitors for use according to the invention.

In another embodiment of the above methods, hGDF-15 inhibitors for use, kits, compositions, or compositions for use, the hGDF-15 inhibitor is the sole ingredient which is pharmaceutically active against cancer.

In an alternative embodiment of the above methods, hGDF-15 inhibitors for use, kits, compositions, or compositions for use, the hGDF-15 inhibitor and the immune checkpoint blocker are the sole ingredients which are pharmaceutically active against cancer.

In an alternative embodiment of the above methods, hGDF-15 inhibitors for use, kits, combinations, compositions, or compositions for use, the hGDF-15 inhibitor is used in combination with one or more further ingredients pharmaceutically active against cancer. In one aspect of this embodiment, the one or more further ingredients pharmaceutically active against cancer is a known anticancer agent and/or an immune-stimulatory molecule. Known anticancer agents include but are not limited to alkylating agents such as cisplatin, carboplatin, oxaliplatin, mechlorethamine, cyclophosphamide, chlorambucil, and ifosfamide; anti-metabolites such as azathioprine and mercaptopurine; alkaloids such as vinca alkaloids (e.g. vincristine, vinblastine, vinorelbine, and vindesine), taxanes (e.g. paclitaxel, docetaxel) etoposide and teniposide; topoisomerase inhibitors such as camptothecins (e.g. irinotecan and topotecan); cytotoxic antibiotics such as actinomycin, anthracyclines, doxorubicin, daunorubicin, valrubicin, idarubicin, epirubicin, bleomycin, plicamycin and mitomycin; and radioisotopes. The following ingredients pharmaceutically active against cancer are particularly preferred to be used in combination with the hGDF-15 inhibitor: Immune-stimulatory molecules include anti-LAG-3, anti-B7H3, anti-TIM3, anti-VISTA, anti-TIGIT, anti-KIR, anti-CD27, anti-CD137, anti-Ox40, anti-4-1BB, anti-GITR, anti-CD28, anti-CD40 or IDO-Inhibitors. Furthermore, other antibody treatments like anti-Her2, anti-EGFR, anti-Claudin, or their glyco-optimized successors are also particularly preferred as they will benefit from a combination with the hGDF-15 inhibitor, e.g. due to enhanced immune cell infiltration in the solid cancer caused by the hGDF-15 inhibitor. Likewise, vaccination approaches (e.g. with peptides or dendritic cells) or adoptive cell therapies, tumor-reactive T cells or dendritic cells are also particularly preferred as they will benefit from a combination with the hGDF-15 inhibitor. Furthermore, the following treatments are also particularly preferred as they will synergize with the hGDF-15 inhibitor:

Treatments with antibodies or antibody-like molecules having one or more specificities for tumor and immune cells (e.g. Bites, DARTS, DARPINS, Catumaxomab);

treatments by vaccine-based immunotherapy against tumor associated peptides, for instance with multi-peptide vaccines such as IMA901, ISA203 or with RNA-based vaccines (e.g. CV9104), and/or treatments with immune cell-activating substances (e.g. FAA derivatives to activate macrophages, or ligands for toll-like receptors such as SLP-AMPLIVANT conjugates).

Combinations for Uses According to the Invention

The present invention encompasses combinations of an hGDF-15 inhibitor and an immune checkpoint blocker for use in a method of treating a solid cancer in a human patient, wherein the hGDF-15 inhibitor and the immune checkpoint blocker are to be administered to the human patient. These combinations and their preferred embodiments are as defined above.

The combination of the hGDF-15 inhibitor and the immune checkpoint blocker may either be administered together or separately.

For instance, in one preferred embodiment, administration of the hGDF-15 inhibitor is to be started prior to the start of administration of the immune checkpoint blocker. This setting advantageously allows to increase the percentage of T-cells, and in particular the percentage of $CD8^+$ T cells in the solid cancer, such that a subsequent treatment with the immune checkpoint blocker can be more effective due to the increased starting percentage of $CD8^+$ T cells in the solid cancer.

Kits

The present invention also provides a kit comprising an hGDF-15 inhibitor and at least one immune checkpoint blocker, as defined above.

The hGDF-15 inhibitor and one or more or all of the immune checkpoint blockers can be contained in separate containers or in a single container.

A container as used can be any type of container that is suitable to store the hGDF-15 inhibitor and/or the at least one immune checkpoint blocker. Non-limiting examples of such containers are vials and pre-filled syringes.

In addition to the hGDF-15 inhibitor and the at least one immune checkpoint blocker, the kit may contain further therapeutic agents. For instance, the kit may contain one or more further ingredients pharmaceutically active against cancer. The one or more further ingredients pharmaceutically active against cancer can be as defined above. Such further ingredients pharmaceutically active against cancer may be used in the methods of the invention together with the hGDF-15 inhibitor and the at least one immune checkpoint blocker.

Preferably, a kit according to the invention further comprises instructions for use.

Sequences

The amino acid sequences referred to in the present application are as follows (in an N-terminal to C-terminal order; represented in the one-letter amino acid code):

```
SEQ ID No: 1 (Region of the Heavy Chain Variable Domain comprising an FR1, a CDR1,
an FR2, a CDR2 and an FR3 region from the Polypeptide Sequence of monoclonal anti-human
GDF-15 mAb-B1-23):
QVKLQQSGPGILQSSQTLSLTCSFSGFSLSTSGMGVSWIRQPSGKGLEWLAHIYWDDDKRYNPTLKSRLTISK
DPSRNQVFLKITSVDTADTATYYC SEQ ID No: 2 (Region of the Light Chain Variable Domain comprising an FR1, a CDR1, an FR2,
a CDR2 and an FR3 region from the Polypeptide Sequence of monoclonal anti-human GDF-15 mAb-B1-23):
DIVLTQSPKFMSTSVGDRVSVTCKASQNVGTNVAWFLQKPGQSPKALIYSASYRYSGVPDRFTGSGSGTDFT
LTISNVQSEDLAEYFC SEQ ID No: 3 (Heavy Chain CDR1 Region Peptide Sequence of monoclonal anti-human
GDF-15 mAb-B1-23):
GFSLSTSGMG SEQ ID No: 4 (Heavy Chain CDR2 Region Peptide Sequence of monoclonal anti-human
GDF-15 mAb-B1-23):
IYWDDDK SEQ ID No: 5 (Heavy Chain CDR3 Region Peptide Sequence of monoclonal anti-human
GDF-15 mAb-B1-23):
ARSSYGAMDY SEQ ID No: 6 (Light Chain CDR1 Region Peptide Sequence of monoclonal anti-human
GDF-15 mAb-B1-23):
QNVGTN Light Chain CDR2 Region Peptide Sequence of monoclonal anti-human GDF-15 mAb-B1-23:
SAS SEQ ID No: 7 (Light Chain CDR3 Region Peptide Sequence of monoclonal anti-human GDF-15 mAb-B1-23):
QQYNNFPYT SEQ ID No: 8 (recombinant mature human GDF-15 protein):
GSARNGDHCPLGPGRCCRLHTVRASLEDLGWADWVLSPREVQVTMCIGACPSQFRAANMHAQIKTSLHRLK

PDTVPAPCCVPASYNPMVLIQKTDTGVSLQTYDDLLAKDCHCI

SEQ ID No: 9 (human GDF-15 precursor protein):
MPGQELRTVNGSQMLLVLLVLSWLPHGGALSLAEASRASFPGPSELHSEDSRFRELRKRYEDLLTRLRANQS

WEDNTDLVPAPAVRILTPEVRLGSGGHLHLRISRAALPEGLPEASRLHRALFRLSPTASRSWDVTRPLRRQL

SLARPQAPALHLRLSPPPSQSDQLLAESSSARPQLELHLRPQAARGRRRARARNGDHCPLGPGRCCRLHTV

RASLEDLGWADWVLSPREVQVTMCIGACPSQFRAANMHAQIKTSLHRLKPDTVPAPCCVPASYNPMVLIQKT

DTGVSLQTYDDLLAKDCHCI

SEQ ID No: 10 (human GDF-15 precursor protein + N-terminal and C-terminal GSGS linker):
GSGSGSGMPGQELRTVNGSQMLLVLLVLSWLPHGGALSLAEASRASFPGPSELHSEDSRFRELRKRYEDLL

TRLRANQSWEDNTDLVPAPAVRILTPEVRLGSGGHLHLRISRAALPEGLPEASRLHRALFRLSPTASRSWDV
```

TRPLRRQLSLARPQAPALHLRLSPPPSQSDQLLAESSSARPQLELHLRPQAARGRRRARARNGDHCPLGPG

RCCRLHTVRASLEDLGWADWVLSPREVQVTMCIGACPSQFRAANMHAQIKTSLHRLKPDTVPAPCCVPASY

NPMVLIQKTDTGVSLQTYDDLLAKDCHCIGSGSGSG

SEQ ID No: 11 (Flag peptide):
DYKDDDDKGG

SEQ ID No: 12 (HA peptide):
YPYDVPDYAG

SEQ ID No: 13 (peptide derived from human GDF-15):
ELHLRPQAARGRR

SEQ ID No: 14 (peptide derived from human GDF-15):
LHLRPQAARGRRR

SEQ ID No: 15 (peptide derived from human GDF-15):
HLRPQAARGRRRA

SEQ ID No: 16 (peptide derived from human GDF-15):
LRPQAARGRRRAR

SEQ ID No: 17 (peptide derived from human GDF-15):
RPQAARGRRRARA

SEQ ID No: 18 (peptide derived from human GDF-15):
PQAARGRRRARAR

SEQ ID No: 19 (peptide derived from human GDF-15):
QAARGRRRARARN

SEQ ID No: 20 (peptide derived from human GDF-15):
MHAQIKTSLHRLK

SEQ ID No: 25 (GDF-15 peptide comprising part of the GDF-15 Epitope that binds to B1-23):
EVQVTMCIGACPSQFR SEQ ID No: 26 (GDF-15 peptide comprising part of the GDF-15 Epitope that binds to B1-23):
TDTGVSLQTYDDLLAKDCHCI The nucleic acid sequences referred to in the present application are as follows (in a 5' to 3' order; represented in accordance with the standard nucleic acid code):

SEQ ID No: 21 (DNA nucleotide sequence encoding the amino acid sequence defined in SEQ ID No: 1):
CAAGTGAAGCTGCAGCAGTCAGGCCCTGGGATATTGCAGTCCTCCCAGAC

CCTCAGTCTGACTTGTTCTTTCTCTGGGTTTTCACTGAGTACTTCTGGTA

TGGGTGTGAGCTGGATTCGTCAGCCTTCAGGAAAGGGTCTGGAGTGGCTG

GCACACATTTACTGGGATGATGACAAGCGCTATAACCCAACCCTGAAGAG

CCGGCTCACAATCTCCAAGGATCCCTCCAGAAACCAGGTATTCCTCAAGA

TCACCAGTGTGGACACTGCAGATACTGCCACATACTACTGT

SEQ ID No: 22 (DNA nucleotide sequence encoding the amino acid sequence defined in SEQ ID No: 2):
GACATTGTGCTCACCCAGTCTCCAAAATTCATGTCCACATCAGTAGGAGA

CAGGGTCAGCGTCACCTGCAAGGCCAGTCAGAATGTGGGTACTAATGTGG

CCTGGTTTCTACAGAAACCAGGGCAATCTCCTAAAGCACTTATTTACTCG

GCATCCTACCGGTACAGTGGAGTCCCTGATCGCTTCACAGGCAGTGGATC

TGGGACAGATTTCACTCTCACCATCAGCAACGTGCAGTCTGAAGACTTGG

CAGAGTATTTCTGT

SEQ ID No: 23 (DNA nucleotide sequence encoding the amino acid sequence defined in SEQ ID No: 5):
GCTCGAAGTTCCTACGGGGCAATGGACTAC SEQ ID No: 24 (DNA nucleotide sequence encoding the amino acid sequence defined in SEQ ID No: 7):
CAGCAATATAACAACTTTCCGTACACG Further amino acid sequences are as follows (in an N-terminal to C-terminal order; represented in the one-letter amino acid code):

SEQ ID No: 27 (amino acid sequence of the heavy chain of the H1L5 humanized B1-23 anti-GDF-15 antibody):
QITLKESGPTLVKPTQTLTLTCTFSGFSLSTSGMGVSWIRQPPGKGLEWLAHIYWDDDKRYNPTLKSRLTITKD

PSKNQVVLTMTNMDPVDTATYYCARSSYGAMDYWGQGTLVTVSSASTKGPSVFPLAPSSKSTSGGTAALGC

LVKDYFPEPVTVSWNSGALTSGVHTFPAVLQSSGLYSLSSWTVPSSSLGTQTYICNVNHKPSNTKVDKKVEP

KSCDKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGNVFSCSVMHEAL

HNHYTQKSLSLSPGK

SEQ ID No: 28 (amino acid sequence of the heavy chain variable domain of the
H1L5 humanized B1-23 anti-GDF-15 antibody):
QITLKESGPTLVKPTQTLTLTCTFSGFSLSTSGMGVSWIRQPPGKGLEWLAHIYWDDDKRYNPTLKSRLTITKD

PSKNQVVLTMTNMDPVDTATYYCARSSYGAMDYWGQGTLVTVSS

SEQ ID No: 29 (amino acid sequence of the heavy chain constant domain of the
H1L5 humanized B1-23 anti-GDF-15 antibody):
ASTKGPSVFPLAPSSKSTSGGTAALGCLVKDYFPEPVTVSWNSGALTSGVHTFPAVLQSSGLYSLSSWIVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDGSFF

LYSKLIVDKSRWQQGNVFSCSVMHEALHNHYTQKSLSLSPGK

SEQ ID No: 30 (amino acid sequence of the light chain of the H1L5 humanized B1-23
anti-GDF-15 antibody):
DIVLTQSPSFLSASVGDRVTITCKASQNVGTNVAWFQQKPGKSPKALIYSASYRYSGVPDRFTGSGSGTEFTL

TISSLQPEDFAAYFCQQYNNFPYTFGGGTKLEIKRAPSVFIFPPSDEQLKSGTASVVCLLNNFYPREAKVQWK

VDNALQSGNSQESVTEQDSKDSTYSLSSTLTLSKADYEKHKVYACEVTHQGLSSPVTKSFNRGEC

SEQ ID No: 31 (amino acid sequence of the light chain variable domain of the H1L5
humanized B1-23 anti-GDF-15 antibody):
DIVLTQSPSFLSASVGDRVTITCKASQNVGTNVAWFQQKPGKSPKALIYSASYRYSGVPDRFTGSGSGTEFTL

TISSLQPEDFAAYFCQQYNNFPYTFGGGTKLEIKR

SEQ ID No: 32 (amino acid sequence of the light chain constant domain of the H1L5
humanized B1-23 anti-GDF-15 antibody):
APSVFIFPPSDEQLKSGTASVVCLLNNFYPREAKVQWKVDNALQSGNSQESVTEQDSKDSTYSLSSTLTLSKA

DYEKHKVYACEVTHQGLSSPVTKSFNRGEC

SEQ ID No: 33 (amino acid sequence of the heavy chain of the chimeric B1-23 anti-GDF-
15 antibody):
QVKLQQSGPGILQSSQTLSLTCSFSGFSLSTSGMGVSWIRQPSGKGLEWLAHIYWDDDKRYNPTLKSRLTISK

DPSRNQVFLKITSVDTADTATYYCARSSYGAMDYWGQGTSVIVSSASTKGPSVFPLAPSSKSTSGGTAALGC

LVKDYFPEPVTVSWNSGALTSGVHTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQVYTLPPSREEMTKN

QVSLTCLVKGFYPSDIAVEWESNGQPENNYKTTPPVLDSDGSFFLYSKLTVDKSRWQQGNVFSCSVMHEAL

HNHYTQKSLSLSPGK

SEQ ID No: 34 (amino acid sequence of the heavy chain variable domain of the
chimeric B1-23 anti-GDF-15 antibody):
QVKLQQSGPGILQSSQTLSLTCSFSGFSLSTSGMGVSWIRQPSGKGLEWLAHIYWDDDKRYNPTLKSRLTISK

DPSRNQVFLKITSVDTADTATYYCARSSYGAMDYWGQGTSVIVSS

SEQ ID No: 35 (amino acid sequence of the heavy chain constant domain of the chimeric
B1-23 anti-GDF-15 antibody):
ASTKGPSVFPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDGSFF

LYSKLIVDKSRWQQGNVFSCSVMHEALHNHYTQKSLSLSPGK

SEQ ID No: 36 (amino acid sequence of the light chain of the chimeric B1-23 anti-GDF-15
antibody):
DIVLTQSPKFMSTSVGDRVSVTCKASQNVGTNVAWFLQKPGQSPKALIYSASYRYSGVPDRFTGSGSGTDFT

LTISNVQSEDLAEYFCQQYNNFPYTFGGGTKLEIKRIVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFNRGEC

SEQ ID No: 37 (amino acid sequence of the light chain variable domain of the chimeric B1-23
anti-GDF-15 antibody):
DIVLTQSPKFMSTSVGDRVSVTCKASQNVGTNVAWFLQKPGQSPKALIYSASYRYSGVPDRFTGSGSGTDFT

LTISNVQSEDLAEYFCQQYNNFPYTFGGGTKLEIKRIVA

SEQ ID No: 38 (amino acid sequence of the light chain constant domain of the chimeric B1-23
anti-GDF-15 antibody):
APSVFIFPPSDEQLKSGTASVVCLLNNFYPREAKVQWKVDNALQSGNSQESVTEQDSKDSTYSLSSTLTLSKA

DYEKHKVYACEVTHQGLSSPVTKSFNRGEC

SEQ ID No: 39 (amino acid sequence of the heavy chain variable domain of the 01G06 antibody):
QVQLVQSGAEVKKPGASVKVSCKASGYTFTDYNMDWVRQAPGQSLEWMGQINPNNGLIFFNQKFQGRVTL

TTDTSTSTAYMELRSLRSDDTAVYYCAREAITTVGAMDYWGQGTLVTVSS

SEQ ID No: 40 (amino acid sequence of the light chain variable domain of the 01G06 antibody):
DIQMTQSPSSLSASVGDRVTITCRTSENLHNYLAWYQQKPGKSPKLLIYDAKTLADGVPSRFSGSGSGTDY

TLTISSLQPEDFATYYCQHFWSDPYTFGQGTKLEIK

SEQ ID No: 41 (amino acid sequence of the heavy chain variable domain of the 03G05 antibody):
QVQLQQPGAELVKPGASVKLSCKASGYTFTSYWIHWVNQRPGQGLEWIGDINPSNGRSKYNEKFKNKATMT

ADKSSNTAYMQLSSLTSEDSAVYYCAREVLDGAMDYWGQGTSVIVSS

SEQ ID No: 42 (amino acid sequence of the light chain variable domain of the 03G05 antibody):
DIVLTQSPASLAVSLGQRATISCRASESVDNYGISFMNWFQQKPGQPPKLLIYAASNQGSGVPARFSGSGS

GTDFSLNIHPMEEDDTAMYFCQQSKEVPWTFGGGSKLEIK

SEQ ID No: 43 (amino acid sequence of the heavy chain variable domain of the 04F08 antibody):
QVTLKESGPGILQPSQTLSLTCSFSGFSLSTYGMGVTWIRQPSGKGLEWLAHIYWDDDKRYNPSLKSRLTI

SKDTSNNQVFLKITSVDTADTATYYCAQTGYSNLFAYWGQGTLVTVSA

SEQ ID No: 44 (amino acid sequence of the light chain variable domain of the 04F08 antibody):
DIVMTQSQKFMSTSVGDRVSVTCKASQNVGTNVAWYQQKLGQSPKTLIYSASYRYSGVPDRFTGSGSGTDF

TLTISNVQSEDLAEYFCQQYNSYPYTFGGGTKLEIK

SEQ ID No: 45 (amino acid sequence of the heavy chain variable domain of the 06C11 antibody):
QVTLKESGPGILQPSQTLSLTCSFSGFSLNTYGMGVSWIRQPSGKGLEWLAHIYWDDDKRYNPSLKSRLTI

SKDASNNRVFLKITSVDTADTATYYCAQRGYDDYWGYWGQGTLVTISA

SEQ ID No: 46 (amino acid sequence of the light chain variable domain of the 06C11 antibody):
DIVMTQSQKFMSTSVGDRVSVTCKASQNVGTNVAWFQQKPGQSPKALIYSASYRYSGVPDRFTGSGSGTDF

ILTISNVQSEDLAEYFCQQYNNYPLTFGAGTKLELK

SEQ ID No: 47 (amino acid sequence of the heavy chain variable domain of the 08G01 antibody):
EVLLQQSGPEVVKPGASVKIPCKASGYTFTDYNMDWVKQSHGKSLEWIGEINPNNGGTFYNQKFKGKATLT

VDKSSSTAYMELRSLTSEDTAVYYCAREAITTVGAMDYWGQGTSVTVSS

SEQ ID No: 48 (amino acid sequence of the light chain variable domain of the 08G01 antibody):
DIQMTQSPASLSASVGETVTITCRASGNIHNYLAWYQQKQGKSPQLLVYNAKTLADGVPSRFSGSGSGTQY

SLKINSLQPEDFGSYYCQHFWSSPYTFGGGTKLEIK

SEQ ID No: 49 (amino acid sequence of the heavy chain variable domain of the 14F11 antibody):
QVTLKESGPGILQPSQTLSLTCSFSGFSLSTYGMGVGWIRQPSGKGLEWLADIWWDDDKYYNPSLKSRLTI

SKDTSSNEVFLKIAIVDTADTATYYCARRGHYSAMDYWGQGTSVTVSS

SEQ ID No: 50 (amino acid sequence of the light chain variable domain of the 14F11 antibody):
DIVMTQSQKFMSTSVGDRVSVTCKASQNVGTNVAWYQQKPGQSPKALIYSPSYRYSGVPDRFTGSGSGTDF

TLTISNVQSEDLAEYFCQQYNSYPHTFGGGTKLEMK

-continued

SEQ ID No: 51 (amino acid sequence of the heavy chain variable domain of the 17B11 antibody):
QVTLKESGPGILQPSQTLSLTCSFSGFSLSTSGMGVSWIRQPSGKGLEWLAHNDWDDDKRYKSSLKSRLTI

SKDTSRNQVFLKITSVDTADTATYYCARRVGGLEGYFDYWGQGTTLTVSS

SEQ ID No: 52 (amino acid sequence of the light chain variable domain of the 17B11 antibody):
DIVLTQSPASLAVSLGQRATISCRASQSVSTSRFSYMHWFQQKPGQAPKLLIKYASNLESGVPARFSGSGS

GTDFTLNIHPVEGEDTATYYCQHSWEIPYTFGGGTKLEIK

EXAMPLES

Reference Examples 1 to 3 exemplify an hGDF-15 inhibitor, which can be used in the compositions, kits, methods and uses according to the invention. This hGDF-15 inhibitor is a monoclonal antibody which is known from WO 2014/049087, which is incorporated herein by reference in its entirety:

Reference Example 1: Generation and Characterization of the GDF-15 Antibody B1-23

The antibody B1-23 was generated in a GDF-15 knock out mouse. Recombinant human GDF-15 (SEQ ID No: 8) was used as the immunogen.

The hybridoma cell line B1-23 producing mAb-B1-23 was deposited by the Julius-Maximilians-Universitat Würzburg, Sanderring 2, 97070 Würzburg, Germany, with the Deutsche Sammlung für Mikroorganismen and Zellkulturen GmbH (DMSZ) at Inhoffenstraße 7B, 38124 Braunschweig, Germany, under the accession No. DSM ACC3142, in accordance with the Budapest Treaty. The deposit was filed on Sep. 29, 2011.

By means of a commercially available test strip system, B1-23 was identified as an IgG2a (kappa chain) isotype. Using surface plasmon resonance measurements, the dissociation constant (Kd) was determined as follows:

Binding of the monoclonal anti-human-GDF-15 antibody anti-human GDF-15 mAb-B1-23 according to the invention was measured by employing surface plasmon resonance measurements using a Biorad ProteOn XPR36 system and Biorad GLC sensor chips:

For preparing the biosensors recombinant mature human GDF-15 protein was immobilized on flow cells 1 and 2. On one flow cell recombinant GDF-15 derived from Baculvirus-transfected insect cells (HighFive insect cells) and on the other recombinant protein derived from expression in E. coli was used. The GLC sensor chip was activated using Sulfo-NHS (N-Hydroxysulfosuccinimide) and EDC (1-Ethyl-3-[3-dimethylaminopropyl]carbodiimide hydrochloride) (Biorad ProteOn Amine Coupling Kit) according to the manufacturer's recommendation, the sensor surface was subsequently loaded with the proteins up to a density of about 600 RU (1 Ru=1 pg mm$^{-2}$). The non-reacted coupling groups were then quenched by perfusion with 1M ethanolamine pH 8.5 and the biosensor was equilibrated by perfusing the chip with running buffer (10M HEPES, 150 mM NaCl, 3.4 mM EDTA, 0.005% Tween-20, pH 7.4, referred to as HBS150). As controls two flow cells were used, one empty with no protein coupled and one coupled with an non-physiological protein partner (human Interleukin-5), which was immobilized using the same coupling chemistry and the same coupling density. For interaction measurements anti-human GDF-15 mAb-B1-23 was dissolved in HBS150 and used in six different concentrations as analyte (concentration: 0.4, 0.8, 3, 12, 49 and 98 nM). The analyte was perfused over the biosensor using the one-shot kinetics setup to avoid intermittent regeneration, all measurements were performed at 25° C. and using a flow rate of 100 µl min$^{-1}$. For processing the bulk face effect and unspecific binding to the sensor matrix was removed by subtracting the SPR data of the empty flow cell (flow cell 3) from all other SPR data. The resulting sensogram was analyzed using the software ProteOn Manager version 3.0. For analysis of the binding kinetics a 1:1 Langmuir-type interaction was assumed. For the association rate constant a value of 5.4±0.06×10$^5$ M$^{-1}$ s$^{-1}$ (k$_{on}$) and for the dissociation rate constant a value of 4.3±0.03×10$^{-4}$ s$^{-1}$ (k$_{off}$) could be determined (values are for the interaction of anti-human GDF-15 mAb-B1-23 with GDF-15 derived from insect cell expression). The equilibrium dissociation constant was calculated using the equation K$_D$=k$_{off}$/k$_{on}$ to yield a value of about 790 pM. Affinity values for the interaction of GDF-15 derived from E. coli expression and the anti-human GDF-15 mAb-B1-23 differ by less than a factor of 2, rate constants for GDF-15 derived from insect cells and E. coli deviate by about 45% and are thus within the accuracy of SPR measurements and likely do not reflect a real difference in affinity. Under the conditions used the anti-human GDF-15 mAb-B1-23 shows no binding to human interleukin-5 and thus confirms the specificity of the interaction data and the anti-human GDF-15 mAb-B1-23.

The amino acid sequence of recombinant human GDF-15 (as expressed in Baculovirus-transfected insect cells) is:

```
                                          (SEQ ID No: 8)
GSARNGDHCP LGPGRCCRLH TVRASLEDLG WADWVLSPRE

VQVTMCIGAC PSQFRAANMH AQIKTSLHRL KPDTVPAPCC

VPASYNPMVL IQKTDTGVSL QTYDDLLAKD CHCI
```

Thus, using surface plasmon resonance measurements, the dissociation constant (Kd) of 790 pM was determined. As a comparison: the therapeutically used antibody Rituximab has a significantly lower affinity (Kd=8 nM).

It was previously shown that mAb B1-23 inhibits cancer cell proliferation in vitro, and that mAb B1-23 inhibits growth of tumors in vivo (WO2014/049087).

Reference Example 2: mAb B1-23 Recognizes a Conformational or a Discontinuous Epitope of Human GDF-15

Epitope Mapping: Monoclonal mouse antibody GDF-15 against 13mer linear peptides derived from GDF-15
Antigen: GDF-15:

```
                                          (SEQ ID No: 10)
GSGSGSGMPGQELRTVNGSQMLLVLLVLSWLPHGGALSLAEASRASFPGP

SELHSEDSRFRELRKRYEDLLTRLRANQSWEDSNTDLVPAPAVRILTPEV

RLGSGGHLHLRISRAALPEGLPEASRLHRALFRLSPTASRSWDVTRPLRR
```

-continued

```
QLSLARPQAPALHLRLSPPPSQSDQLLAESSSARPQLELHLRPQAARGRR

RARARNGDHCPLGPGRCCRLHTVRASLEDLGWADWVLSPREVQVTMCIGA

CPSQFRAANMHAQIKTSLHRLKPDTVPAPCCVPASYNPMVLIQKTDTGVS

LQTYDDLLAKDCHCIGSGSGSG (322 amino acids with linker)
```

The protein sequence was translated into 13mer peptides with a shift of one amino acid. The C- and N-termini were elongated by a neutral GSGS linker to avoid truncated peptides (bold letters).

Control Peptides:

```
Flag:
                                     (SEQ ID No: 13)
DYKDDDDKGG, 78 spots;

HA:
                                     (SEQ ID No: 14)
YPYDVPDYAG, 78 spots (each array copy)
```

Peptide Chip Identifier:
000264_01 (10/90, Ala2Asp linker)
Staining Conditions:
Standard buffer: PBS, pH 7.4+0.05% Tween 20
Blocking buffer: Rockland blocking buffer MB-070
Incubation buffer: Standard buffer with 10% Rockland blocking buffer MB-070
Primary sample: Monoclonal mouse antibody GDF-15 (1 µg/µl): Staining in incubation buffer for 16 h at 4° C. at a dilution of 1:100 and slight shaking at 500 rpm
Secondary antibody: Goat anti-mouse IgG (H+L) IRDye680, staining in incubation buffer with a dilution of 1:5000 for 30 min at room temperature (RT)
Control antibodies: Monoclonal anti-HA (12CA5)-LL-Atto 680 (1:1000), monoclonal anti-FLAG(M2)-Fluo-Probes752 (1:1000); staining in incubation buffer for 1 h at RT
Scanner:
Odyssey Imaging System, LI-COR Biosciences
Settings: offset: 1 mm; resolution: 21 µm; intensity green/red: 7/7
Results:
After 30 min pre-swelling in standard buffer and 30 min in blocking buffer, the peptide array with 10, 12 and 15mer B7H3-derived linear peptides was incubated with secondary goat anti-mouse IgG (H+L) IRDye680 antibody only at a dilution of 1:5000 for 1 h at room temperature to analyze background interactions of the secondary antibody. The PEPperCHIP® was washed 2×1 min with standard buffer, rinsed with dist. water and dried in a stream of air. Read-out was done with Odyssey Imaging System at a resolution of 21 µm and green/red intensities of 7/7: We observed a weak interaction of arginine-rich peptides (ELHLRPQAARGRR (SEQ ID No:15), LHLRPQAARGRRR (SEQ ID No:16), HLRPQAARGRRRA (SEQ ID No:17), LRPQAARGRRAR (SEQ ID No:18), RPQAARGRRRARA (SEQ ID No:19), PQAARGRRRARAR (SEQ ID No:20) and QAARGRRRARARN (SEQ ID No:21)) that are known as frequent binders, and with the basic peptide MHAQIKTSLHRLK (SEQ ID No:22) due to ionic interactions with the charged antibody dye.
After pre-swelling for 10 min in standard buffer, the peptide microarray was incubated overnight at 4° C. with monoclonal mouse antibody GDF-15 at a dilution of 1:100. Repeated washing in standard buffer (2×1 min) was followed by incubation for 30 min with the secondary antibody at a dilution of 1:5000 at room temperature. After 2×10 sec. washing in standard buffer and short rinsing with dist. water, the PEPperCHIP® was dried in a stream of air. Read-out was done with Odyssey Imaging System at a resolution of 21 µm and green/red intensities of 7/7 before and after staining of control peptides by anti-HA and anti-FLAG(M2) antibodies.

It was shown that none of the linear 13mer peptides derived from GDF-15 interacted with monoclonal mouse antibody GDF-15 even at overregulated intensities. Staining of Flag and HA control peptides that frame the array, however, gave rise to good and homogeneous spot intensities.

Summary:
The Epitope Mapping of monoclonal mouse GDF-15 antibody against GDF-15 did not reveal any linear epitope with the 13mer peptides derived from the antigen. According to this finding it is very likely that monoclonal mouse antibody GDF-15 recognizes a conformational or a discontinuous epitope with low affinity of partial epitopes. Due to the obvious absence of any GDF-15 signal above the background staining of the secondary antibody only, quantification of spot intensities with PepSlide® Analyzer and subsequent peptide annotation were omitted.

Reference Example 3: Structural Identification of Peptide Ligand Epitopes by Mass Spectrometric Epitope Excision and Epitope Extraction The epitope of recombinant human GDF-15 which binds to the antibody B1-23 was identified by means of the epitope excision method and epitope extraction method (Suckau et al. Proc Natl Acad Sci USA. 1990 December; 87(24): 9848-9852; R. Stefanescu et al., Eur. J. Mass Spectrom. 13, 69-75 (2007)).

For preparation of the antibody column, the antibody B1-23 was added to NHS-activated 6-aminohexanoic acid coupled sepharose. The sepharose-coupled antibody B1-23 was then loaded into a 0.8 ml microcolumn and washed with blocking and washing buffers.

Epitope Extraction Experiment:
Recombinant human GDF-15 was digested with trypsin for 2 h at 37° C. (in solution), resulting in different peptides, according to the trypsin cleavage sites in the protein. After complete digestion, the peptides were loaded on the affinity column containing the immobilized antibody B1-23. Unbound as well as potentially bound peptides of GDF-15 were used for mass spectrometry analysis. An identification of peptides by means of mass spectrometry was not possible. This was a further indicator that the binding region of GDF-15 in the immune complex B1-23 comprises a discontinuous or conformational epitope. In case of a continuous linear epitope, the digested peptides should bind its interaction partner, unless there was a trypsin cleavage site in the epitope peptide. A discontinuous or conformational epitope could be confirmed by the epitope excision method described in the following part.

Epitope Excision Experiment:
The immobilized antibody B1-23 on the affinity column was then incubated with recombinant GDF-15 for 2 h. The formed immune complex on the affinity column was then incubated with trypsin for 2 h at 37° C. The cleavage resulted in different peptides derived from the recombinant GDF-15. The immobilized antibody itself is proteolytically stable. The resulting peptides of the digested GDF-15 protein, which were shielded by the antibody and thus protected from proteolytic cleavage, were eluted under acidic conditions (TFA, pH2), collected and identified by mass spectrometry.

The epitope excision method using MS/MS identification resulted in the following peptides:

| Peptide | Position in sequence | Mass | Ion/Charge |
|---|---|---|---|
| EVQVTMCIGACPSQFR (SEQ ID No: 25) | 40-55 | 1769.91 | 590.50(3+) |
| TDTGVSLQTYDDLLAKDCHCI (SEQ ID No: 26) | 94-114 | 2310.96 | 771:33(3+) |

The part of human GDF-15, which binds the antibody B1-23, comprises a discontinuous or conformational epitope. Mass spectrometry identified 2 peptides in the GDF-15 protein, which are responsible for the formation of the immune complex. These peptides are restricted to the positions 40-55 (EVQVTMCIGACPSQFR) and 94-114 (TDTGVSLQTYDDLLAKDCHCI) in the GDF-15 amino acid sequence. Thus, these two peptides comprise an epitope of the GDF-15 protein that binds to the antibody B1-23.

The present invention is illustrated by the following non-limiting Examples:

Example 1

In human melanoma patients who had received a prior treatment with Ipilimumab (a monoclonal anti-CTLA4 antibody) and failed to show a complete response, and who received a treatment with Pembrolizumab (a monoclonal anti-PD-1 antibody), hGDF-15 Serum Levels correlate with poor treatment response at a time point of four months after the start of the treatment with pembrolizumab.

The present inventors set out to investigate whether cancer patients receiving immune checkpoint blockers could benefit from an inhibition of hGDF-15. In order to test this possibility, sera from melanoma patients, which had received a prior treatment with Ipilimumab (a monoclonal anti-CTLA4 antibody) and received a treatment with Pembrolizumab (a monoclonal anti-PD-1 antibody) in a clinical study, were analyzed for hGDF-15 serum levels. In order to investigate whether hGDF-15 influences the patients' response to immune checkpoint blockers, the obtained hGDF-15 serum levels were then correlated with the patients' responses. Sera were taken from the patients prior to the treatment with Pembrolizumab.

The study and the subsequent analyses were conducted as follows:

Inclusion Criteria of the Clinical Study:

Eligible patients were aged 18 years or older and had histologically or cytologically confirmed unresectable stage III or stage IV melanoma not amenable to local therapy; confirmed disease progression within 24 weeks of the last ipilimumab dose (minimum two doses, 3 mg/kg once every 3 weeks); previous BRAF or MEK inhibitor therapy or both (if BRAFV600 mutant-positive); resolution or improvement of ipilimumab-related adverse events to grade 0-1 and prednisone dose 10 mg/day or less for at least 2 weeks before the first dose of study drug; Eastern Cooperative Oncology Group (ECOG) performance status 0 or 1; measurable disease per Response Evaluation Criteria in Solid Tumors, version 1.1 (RECIST v1.1); and values within the prespecified range for absolute neutrophil count ($\geq 1500$ cells per mL), platelets ($\geq 100\,000$ cells per mL), haemoglobin ($\geq 90$ g/L), serum creatinine ($<-1.5$ upper limit of normal [ULN]), serum total bilirubin ($\leq 1.5$ ULN or direct bilirubin $\leq$ULN for patients with total bilirubin concentrations $>1.5$ ULN), aspartate and alanine aminotransferases ($\leq 2.5$ ULN or $\leq 5$ ULN for patients with liver metastases), international normalised ratio or prothrombin time ($\leq 1.5$ ULN if not using anticoagulants), and activated partial thromboplastin time ($\leq 1.5$ ULN if not using anticoagulants). Patients had a washout period of at least 4 weeks between the last dose of the most recent therapy and the first dose of pembrolizumab. Patients with known active brain metastases or carcinomatous meningitis, active autoimmune disease, active infection requiring systemic therapy, known history of HIV infection, active hepatitis B virus or hepatitis C virus infection, a history of grade 4 ipilimumab-related adverse events or grade 3 ipilimumab-related adverse events lasting longer than 12 weeks, or previous treatment with any other anti-PD-1 or anti-PD-L1 therapy were excluded from the study.

Treatment of Patients:

Human melanoma patients which met the inclusion criteria defined above had (with two exceptions) already been treated with ipilimumab (a monoclonal anti-CTLA4 antibody) and failed to show a complete response. Pembrolizumab (a monoclonal anti-PD-1 antibody).was given either at 2 mg/kg of body weight or at 10 mg/kg of body weight. As no dose-dependent differences were observed between the two treatment groups, treated patients were jointly evaluated.

Criteria for Response:

Responders and Non-responders to the treatment as well as ongoing responses were classified by using the response evaluation criteria in solid tumours, version 1.1 (RECIST v1.1) (Eisenhauer et al.: New response evaluation criteria in solid tumours: revised RECIST guideline (version 1.1). In: Eur. J. Cancer. 45, No. 2, January 2009, pp 228-47).

Analysis of hGDF-15 Serum Levels by Enzyme-Linked Immunosorbent Assay (ELISA):

Human GDF-15 serum levels were measured by Enzyme-Linked Immunosorbent Assay (ELISA).

Buffers and Reagents:

Buffered blocking solution: 1% BSA (fraction V pH 7.0, PM) in PBS

Wash solution: PBS-Tween (0.05%)

Standard: human GDF-15 (stock concentration 120 µg/ml, from R&D Systems)

Capture antibody: Human GDF-15 MAb (Clone 147627) from R&D Systems, Mouse IgG2B (catalog #MAB957, from R&D Systems, stock concentration 360 µg/ml)

Detection antibody: Human GDF-15 Biotinylated Affinity Purified PAb, Goat IgG (catalog #BAF940, from R&D Systems, stock concentration 9 µl/ml)

Streptavidin-HRP (Catalog #DY998, from R&D Systems)

Substrate solution: 10 ml 0.1 M NaOAc pH6.0+100 µl TMB+2 µl $H_2O_2$

Stop solution: 1 M $H_2SO_4$

Analysis Procedure:

1. Plate Preparation:
a. The capture antibody was diluted to the working concentration of 2 µg/ml in PBS. A 96-well microplate (Nunc Maxisorp®) was immediately coated with 50 µl per well of the diluted capture antibody excluding the outer rows (A and H). Rows A and H were filled with buffer to prevent evaporation of the samples during the experiment. The plate was gently tapped to ensure that the bottom of each well was thoroughly covered. The plate was placed in a humid chamber and incubated overnight at room temperature (RT).
b. Each well was aspirated and washed three times with PBS-Tween (0.05%).
c. 150 µl of blocking solution was added to each well, followed by incubation at RT for 1 hour.
d. Each well was aspirated and washed three times with PBS-Tween (0.05%).
2. Assay Procedure:
a. Standards were prepared. GDF-15 was diluted in buffered blocking solution to a final concentration of 1 ng/ml (4.17 µl GDF+496 µl buffered blocking solution). 1:2 serial dilutions were made.
b. Duplicate samples 1:20 (6 µl+114 µl buffered blocking solution) were prepared.
c. 50 µl of diluted samples or standards were added per well, followed by incubation for 1 hour at RT.

|   | 1   | 2   | 3   | 4  | 5  | 6    | 7  | 8  | 9   | 10  | 11 | 12  |
|---|-----|-----|-----|----|----|------|----|----|-----|-----|----|-----|
| A | 0   | 0   | 0   | 0  | 0  | 0    | 0  | 0  | 0   | 0   | 0  | 0   |
| B | s1  | s2  | ... |    |    |      |    |    |     |     |    | s12 |
| C | s1  | s2  | ... |    |    |      |    |    |     |     |    | s12 |
| D | s13 | s14 | ... |    |    |      |    |    |     |     |    | s24 |
| E | s13 | s14 | ... |    |    |      |    |    |     |     |    | s24 |
| F | St  | and | ard |    |    |      |    |    | dil | uti | on | s   |
| G |     |     |     |    | se | rial |    |    |     |     |    |     |
| H | 0   | 0   | 0   | 0  | 0  | 0    | 0  | 0  | 0   | 0   | 0  | 0   | a. Each well was aspirated and washed three times with PBS-Tween (0.05%).
b. The detection antibody was diluted to a final concentration of 50 ng/ml (56 µl+10 ml blocking buffer). 50 µl of the diluted detection antibody was added to each well, followed by incubation for 1 hour at RT.
c. Each well was aspirated and washed three times with PBS-Tween (0.05%).
d. Streptavidin-HRP was diluted 1:200 (50 µl+10 ml blocking buffer). 50 µL of the working dilution of Streptavidin-HRP was added to each well, followed by incubation for 20 min at RT.
e. Each well was aspirated and washed three times with PBS-Tween (0.05%).
f. The substrate solution was prepared. 50 µL of substrate solution was added to each well, followed by incubation for 20 min at RT.
g. 50 µL of stop solution was added to each well.
h. The optical density of each well was determined immediately, using a microplate reader set to 450 nm.
3. Calculation of GDF-15 Serum Titer:
a. Each sample/GDF-15 standard dilution was applied in duplicate. To determine GDF-15 titer, the average of the duplicates was calculated and the background (sample without GDF-15) subtracted.
b. To create a standard curve, values from the linear range were plotted on an X-Y-diagram (X axis: GDF-15 concentration, Y axis: OD450), and a linear curve fit was applied. GDF-15 serum titer of the test samples was calculated by interpolating from the OD450 values of the standard dilutions with known concentration.
c. To calculate the final GDF-15 concentration of the samples, the distinct dilution factor was considered. Samples yielding OD values below or above the standard range were re-analyzed at appropriate dilutions.

Figure 2:
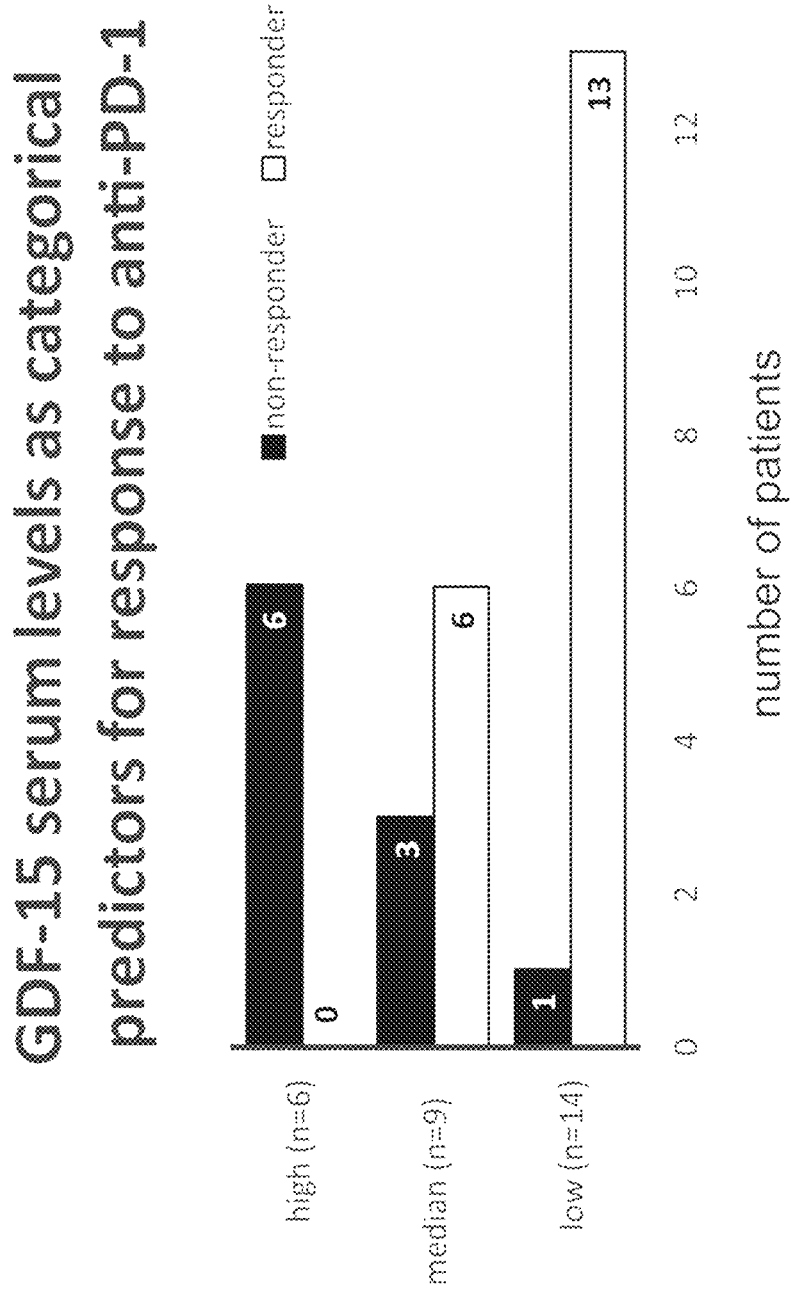
FIG. 2: This Figure shows the numbers of responders and non-responders in the patient groups having hGDF-15 serum levels of <1.8 ng/ml, 1.8-4.2 ng/ml, and >4.2 ng/ml, respectively.

Comparison of hGDF-15 Serum Levels with Patient Data:
Next, the measured hGDF-15 serum levels were compared with patient response data obtained from the study.
FIG. 1 shows the GDF-15 serum levels for responders and non-responders to the treatment regimen. As can be seen from the Figure, most of the non-responders have higher GDF-15 serum levels than all of the responders.
This result is also reflected in FIG. 2, which shows the numbers of responders and non-responders in the patients having hGDF-15 serum levels of <1.8 ng/ml, 1.8-4.2 ng/ml, and >4.2 ng/ml, respectively.
These findings suggested that high GDF-15 levels are related to a poor treatment response. Therefore, these findings were tested for their statistical significance:

Statistical Correlation of hGDF-15 Serum Levels with Patient Data:
Data:
The data analysis was based on a data file containing data from samples from 35 patients containing the columns (variables) Sample designation, GDF-15 (ng/ml), responder/non-responder, days (to death or censoring), and Ongoing (an index variable for ongoing life). The responder/non-responder classification of these data was made at a time point of four months after the start of the treatment with pembrolizumab. As some serum samples had only been obtained shortly before the analysis, response could only by assessed in 29 patients. One partial responder (>30% reduction in tumor size) was rated as responder. For LDH determination, 4 samples had to be excluded due to hemolysis.

Outcome Variables (Endpoints):
a. Overall survival (time to death). This endpoint is composed of the event indicator for death (1=dead/0=alive), which was derived from the data file, and the time to death or censoring (last time the patient was known to be alive), corresponding to the variable "days".
b. Response to treatment, e.g. whether a patient was a responder or not (coded as 1=responder, 0=nonresponder). Partial responders were considered as responders.

| Sample designation | GDF-15 (ng/ml) | LDH[U/I] | responder/ non-responder | Days since anti PD-1 | Prior Ipilimumab treatment | Ongoing Response |
|---|---|---|---|---|---|---|
| HG12.950  | 2.010  | 398  | NR | 72  | x | |
| HG13.1002 | 0.479  | 340  | R  | 538 |   | x |
| HG13.1012 | 12.010 | 3734 | NR | 71  | x | |
| HG13.1067 | 9.173  | 591  | NR | 83  | x | |
| HG13.1069 | 4.635  | 2419 | NR | 53  | x | |
| HG13.1099 | 1.285  | 370  | R  | 693 | x | x |
| HG13.1202 | 1.641  | 480  | R  | 575 | x | |
| HG13.1341 | 4.595  | 1930 | NR | 15  | x | |
| HG13.1377 | 0.539  | 388  | R  | 269 | x | |

-continued

| Sample designation | GDF-15 (ng/ml) | LDH[U/l] | responder/ non-responder | Days since anti PD-1 | Prior Ipilimumab treatment | Ongoing Response |
|---|---|---|---|---|---|---|
| HG13.1419 | 0.914 | 317 | R | 617 | | x |
| HG13.1432 | 1.195 | 269 | R | 611 | x | x |
| HG13.1458 | 0.433 | 453 | R | 605 | x | x |
| HG13.1557 | 4.045 | 564 | R | 293 | x | |
| HG13.1587 | 0.345 | 371 | R | 186 | x | |
| HG13.1663 | 1.320 | hemolytic | R | 176 | x | |
| HG13.516 | 0.641 | 342 | R | 264 | x | |
| HG13.578 | 2.841 | 1143 | R | 266 | x | |
| HG13.596 | 1.085 | hemolytic | R | 772 | x | x |
| HG13.757 | 3.310 | hemolytic | NR | 117 | x | |
| HG13.811 | 4.029 | 763 | R | 596 | x | x |
| HG14.1080 | 5.979 | 1359 | NR | 43 | x | |
| HG14.1108 | 0.979 | 555 | R | 206 | x | x |
| HG14.1147 | 2.084 | 227 | R | 154 | x | x |
| HG14.1159 | 2.150 | 333 | R | 227 | x | x |
| HG14.161 | 0.889 | 343 | | 108 | x | x |
| HG14.557 | 2.014 | 368 | R | 317 | x | x |
| HG14.707 | 2.783 | 442 | NR | 71 | x | |
| HG14.853 | 0.846 | 343 | NR | 71 | x | |
| HG14.885 | 0.874 | hemolytic | PR | 63 | x | |
| HG15.299 | 0.412 | 354 | | 86 | x | x |
| HG15.47 | 1.465 | 475 | | 80 | x | x |
| HG15.49 | 3.912 | 631 | | 93 | x | |
| HG15.546 | 0.358 | hemolytic | | 23 | x | x |
| HG15.560 | 2.389 | 768 | | 21 | x | x |
| HG15.59 | 8.122 | 588 | NR | 23 | x | |

Data Analysis:

Overall survival was analysed by Cox proportional hazard survival models. One model was fitted with GDF-15 (ng/ml) as continuous predictor and another model with a grouping variable based on GDF-15 as categorical predictor (groups were: <1.8 ng/ml, 1.8-4.2 ng/ml, >4.2 ng/ml of GDF-15). Altogether, survival data were available from 35 patients.

Response to treatment (binary variable) was analysed by Generalised Linear Models (GLMs) with binomial error distribution and logit link function (logistic regression). For the response to treatment as assessed by RECIST1.1 criteria after 4 months a model was fitted with GDF-15 (ng/ml) as continuous predictor. Because no patients responded in the group with GDF-15 >4.2 ng/ml, the odds ratio estimate for this group vs. the group with GDF-15<1.8 ng/ml would be very big, with a very wide confidence interval. Instead of fitting another model with the grouping variable based on GDF-15 as categorical predictor, a chi-squared (X2) test was used to compare the groups (testing the equality of the proportion of responders). Because the number of responders/non-responders was sometimes quite small (<5), a sensitivity analysis using Fisher's exact test was done in addition. Patients who had only received anti PD-1 within the last 4 months could not yet be classified as responders or non-responders. Hence, only 29 patients could be evaluated for response to therapy.

Data analysis was performed using the statistical software package R (R Core Team, 2014, version 3.1.0).

Figure 3:
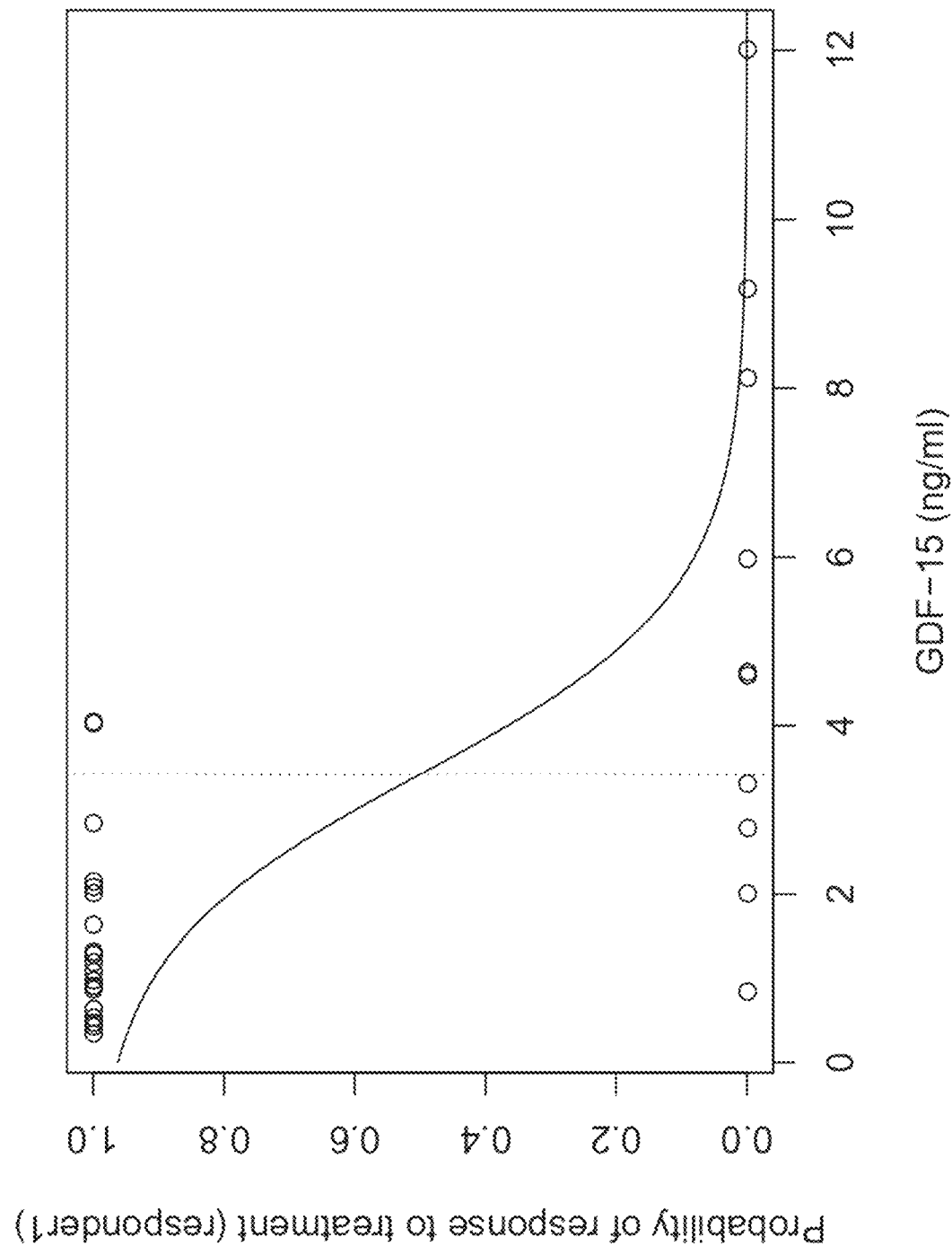
FIG. 3: Probability of response to treatment (responder 1) as predicted by the Generalized Linear Model using GDF-15 as continuous predictor. Circles show the data, the curve shows the model. The vertical line indicates the GDF-15 concentration where the probability of treatment response is 0.5.

Results:

Tables 1-2 show the results from the models with GDF-15 as continuous predictor. The hazard for death significantly increased for higher concentrations of GDF-15 (HR>1, Table 1) whereas the probability of response to treatment significantly decreased, as indicated by the odds ratio (OR) (OR<1, Table 2). FIG. 3 shows the corresponding data on responders/non-responders as well as the probability of response to treatment predicted by the model.

Figure 4:
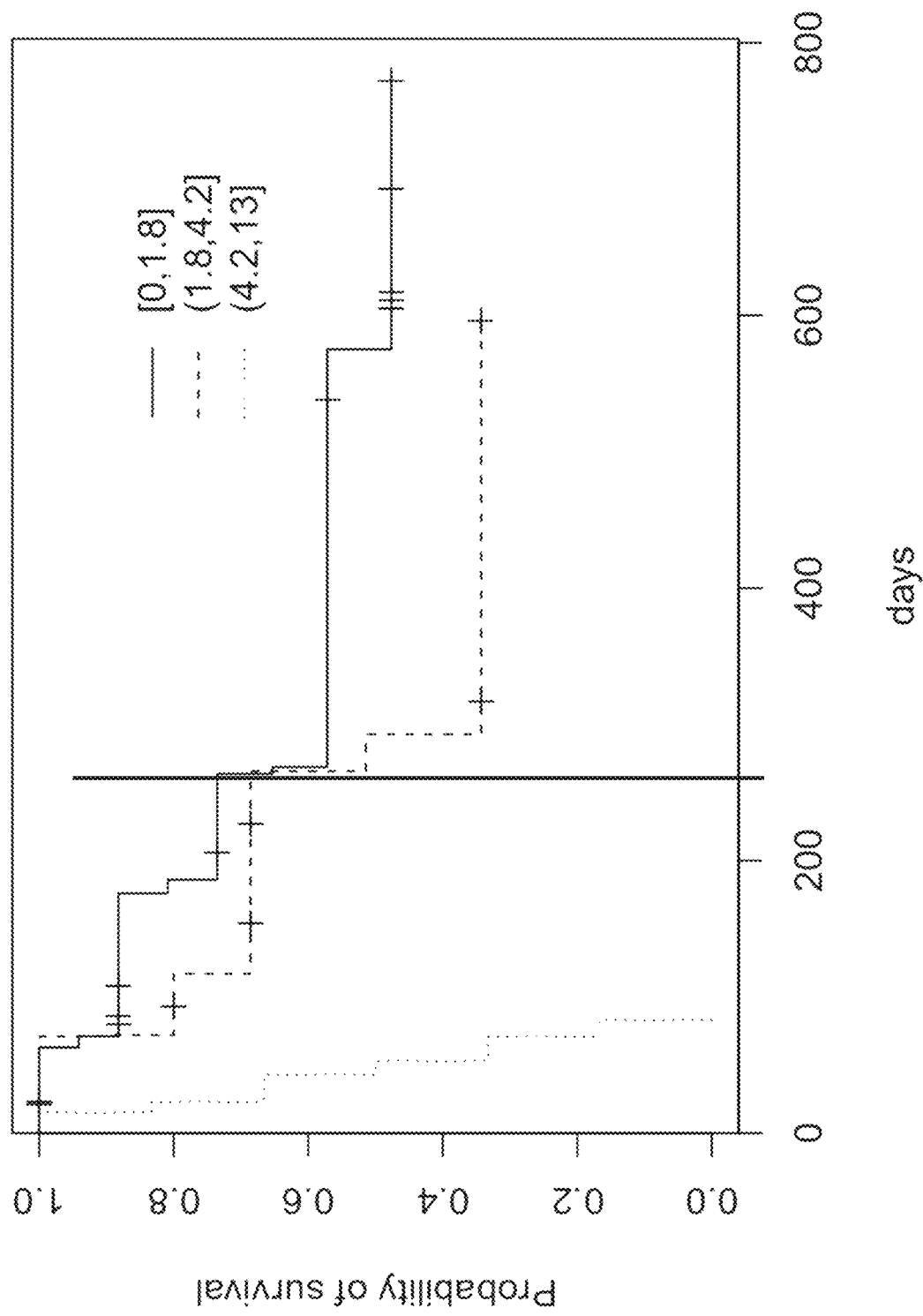
FIG. 4: Kaplan-Meier curves for survival in the three groups defined by the GDF-15 serum level (<1.8, 1.8-4.2, >4.2 ng/ml).

Table 3 shows the result from the Cox proportional hazards model with the group based on GDF-15 as categorical predictor. The group with GDF-15<1.8 ng/ml is used as reference group (not shown in the Table). The two hazard ratios in Table 3 represent the comparison of the group with GDF-15 between 1.8 and 4.2 and the group with GDF-15 >4.2 with the reference group. The hazard for death is increased in both of these groups (compared to the reference group), but to a larger extent in the group with GDF-15 >4.2. FIG. 4 shows the Kaplan-Meier curves for survival in the three groups.

The proportion of responders differed significantly between the groups (responder 1: $X^2_{df=2}$=16.04, P=0.0003). This result was confirmed by the results of Fisher's exact test (P=0.0003). The numbers of deaths and responders per group are given in Table 4. Moreover, Table 5 shows some descriptive statistics of the GDF-15 for each group.

TABLE 1

| | HR | 95% CI | z | p |
|---|---|---|---|---|
| GDF-15 | 1.27 | [1.10, 1.47] | 3.27 | 0.00109 |

Table 1 shows the Hazard ratio (HR) estimates from the Cox proportional hazards model with overall survival (time to death) as outcome variable and GDF-15 as continuous predictor. The analysis included samples from 35 patients.

TABLE 2

| | Estimate (OR) | 95% CI | z | p |
|---|---|---|---|---|
| (Intercept) | 25.281 | [4.219, 364.950] | 2.94 | 0.00324 |
| GDF-15 | 0.389 | [0.159, 0.698] | -2.54 | 0.01120 |

Table 2 shows the Odds ratio (OR) estimates from the Generalized Linear Model with response to treatment (responder 1) as outcome variable and GDF-15 as continuous predictor. The analysis included samples from 29 patients.

TABLE 3

|  | HR | 95% CI | z | p |
|---|---|---|---|---|
| GDF-15-group(1.8, 4.2] | 1.54 | [0.48, 4.92] | 0.73 | 0.466 |
| GDF-15-group(4.2, 13] | 21.52 | [5.20, 89.06] | 4.24 | <0.001 |

Table 3 shows Hazard ratio (HR) estimates from the Cox proportional hazards model with overall survival (time to death) as outcome variable and the group based on GDF-15 as categorical predictor. The analysis included samples from 35 patients.

TABLE 4

| Variable | Levels | $n_{[0,1.8]}$ | $\%_{[0,1.8]}$ | $n_{(1.8,4.2]}$ | $\%_{(1.8,4.2]}$ | $n_{(4.2,13]}$ | $\%_{(4.2,13]}$ | $n_{all}$ | $\%_{all}$ |
|---|---|---|---|---|---|---|---|---|---|
| death | 0 | 11 | 61.1 | 6 | 54.5 | 0 | 0.0 | 17 | 48.6 |
|  | 1 | 7 | 38.9 | 5 | 45.5 | 6 | 100.0 | 18 | 51.4 |
|  | all | 18 | 100.0 | 11 | 100.0 | 6 | 100.0 | 35 | 100.0 |
| responder1 | 0 | 1 | 7.1 | 3 | 33.3 | 6 | 100.0 | 10 | 34.5 |
|  | 1 | 13 | 92.9 | 6 | 66.7 | 0 | 0.0 | 19 | 65.5 |
|  | all | 14 | 100.0 | 9 | 100.0 | 6 | 100.0 | 29 | 100.0 |

Table 4 shows the number of deaths and responders (responder1) in the three groups defined by the GDF-15 (<1.8, 1.8-4.2, >4.2 ng/ml).

TABLE 5

Table 5: The continuous predictor variable GDF-15 (ng/ml) in the three groups defined by the GDF-15 (<1.8, 1.8-4.2, >4.2 ng/ml). The number of patients (n), the median ($\tilde{x}$), the mean ($\bar{x}$), the standard deviation (s), the minimum (Min), and the maximum (Max) are shown.

| Variable | Levels | n | $\tilde{x}$ | $\bar{x}$ | s | Min | Max |
|---|---|---|---|---|---|---|---|
| GDF-15 | [0, 1.8] | 18 | 0.9 | 0.9 | 0.4 | 0.3 | 1.6 |
|  | (1.8, 4.2] | 11 | 2.8 | 2.9 | 0.8 | 2.0 | 4.0 |
|  | (4.2, 13] | 6 | 7.1 | 7.4 | 2.9 | 4.6 | 12.0 |
|  | all | 35 | 1.6 | 2.6 | 2.7 | 0.3 | 12.0 |

Next, in order to compare the statistical results obtained for GDF-15 levels, statistical analysis were also performed for the levels of a known prognostic factor lactate dehydrogenase (LDH) in the patient sera:

Lactate dehydrogenase is considered to be a prognostically relevant marker for solid tumors. This has recently been confirmed by a comprehensive meta-analysis based on a large pool of clinical studies (31,857 patients). A consistent effect of an elevated LDH on OS (HR=1.48, 95% CI=1.43 to 1.53) was found across all disease subgroups and stages. In addition, there was a trend toward a stronger prognostic value of LDH in metastatic disease compared with non-metastatic disease, which was thought to reflect greater tumor burden. While the exact mechanism remains unknown and may also be related to hypoxia and metabolic reprogramming via a Warburg effect, LDH may be interpreted as reflecting high tumor burden or tumor aggressiveness (Zhang, J., Yao, Y.-H., Li, B.-G., Yang, Q., Zhang, P.-Y., and Wang, H.-T. (2015). Prognostic value of pretreatment serum lactate dehydrogenase level in patients with solid tumors: a systematic review and meta-analysis. Scientific Reports 5, 9800). As serum LDH levels have been incorporated into the staging scheme for melanoma, this parameter is routinely measured during clinical diagnostics by the university reference laboratory.

TABLE 6

Table 6: GDF-15 and LDH in responders vs. non-responders

|  | GDF-15 (ng/ml) | | LDH (U/l) | |
|---|---|---|---|---|
|  | Responder (n = 19) | non-responder (n = 10) | Responder (n = 9) | non-responder (n = 16) |
| Median | 1.2 | 4.6 | 371 | 591 |
| Mean | 1.7 | 5.6 | 455 | 1312 |
| Standard deviation | 1.2 | 3.6 | 218 | 1108 |
| ttest (2-sided, type 3) | 0.012 | | 0.061 | |

LDH determination failed in 4 blood samples due to hemolysis.

Figure 5A:
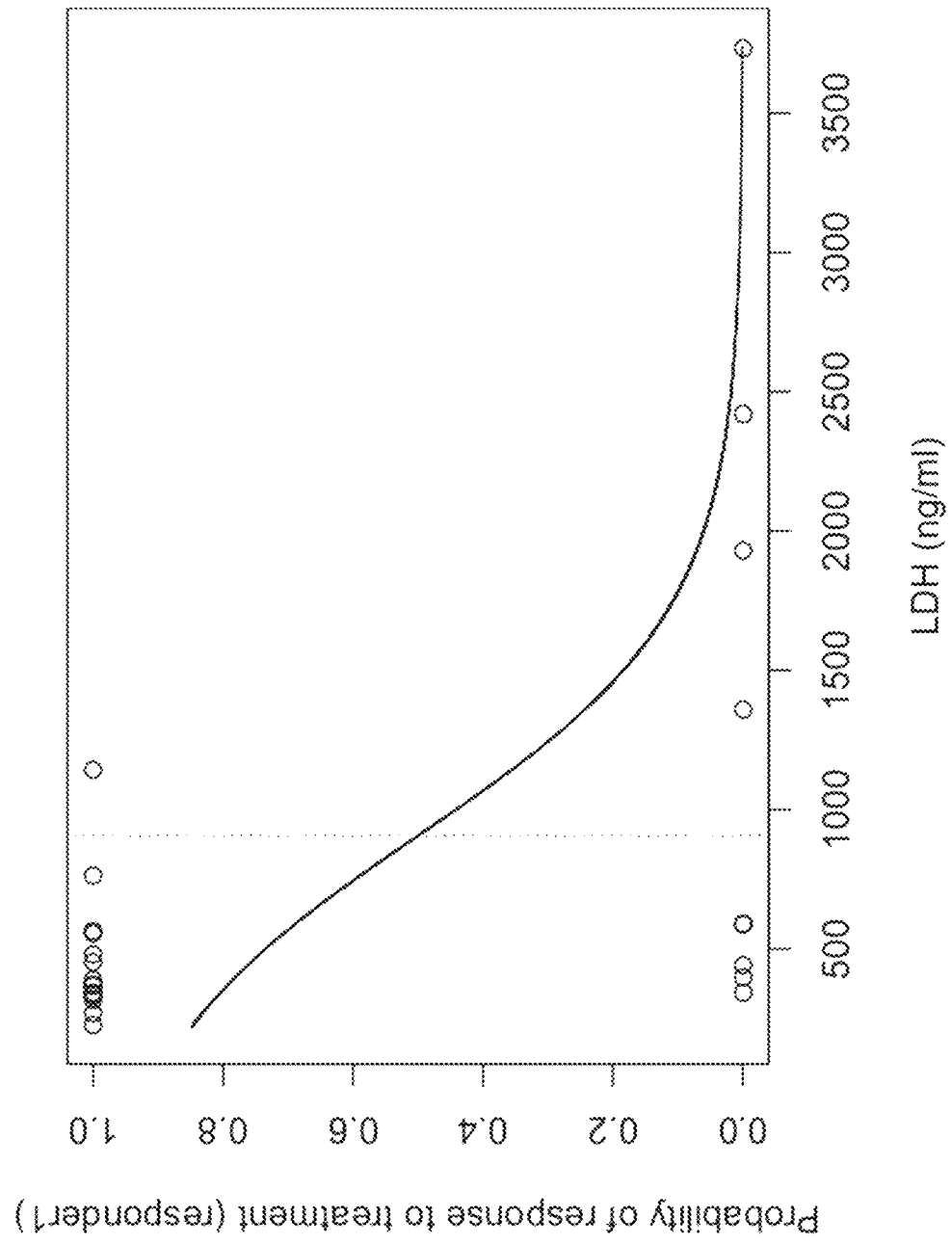
FIGS. 5A-5B.
Figure 5B:
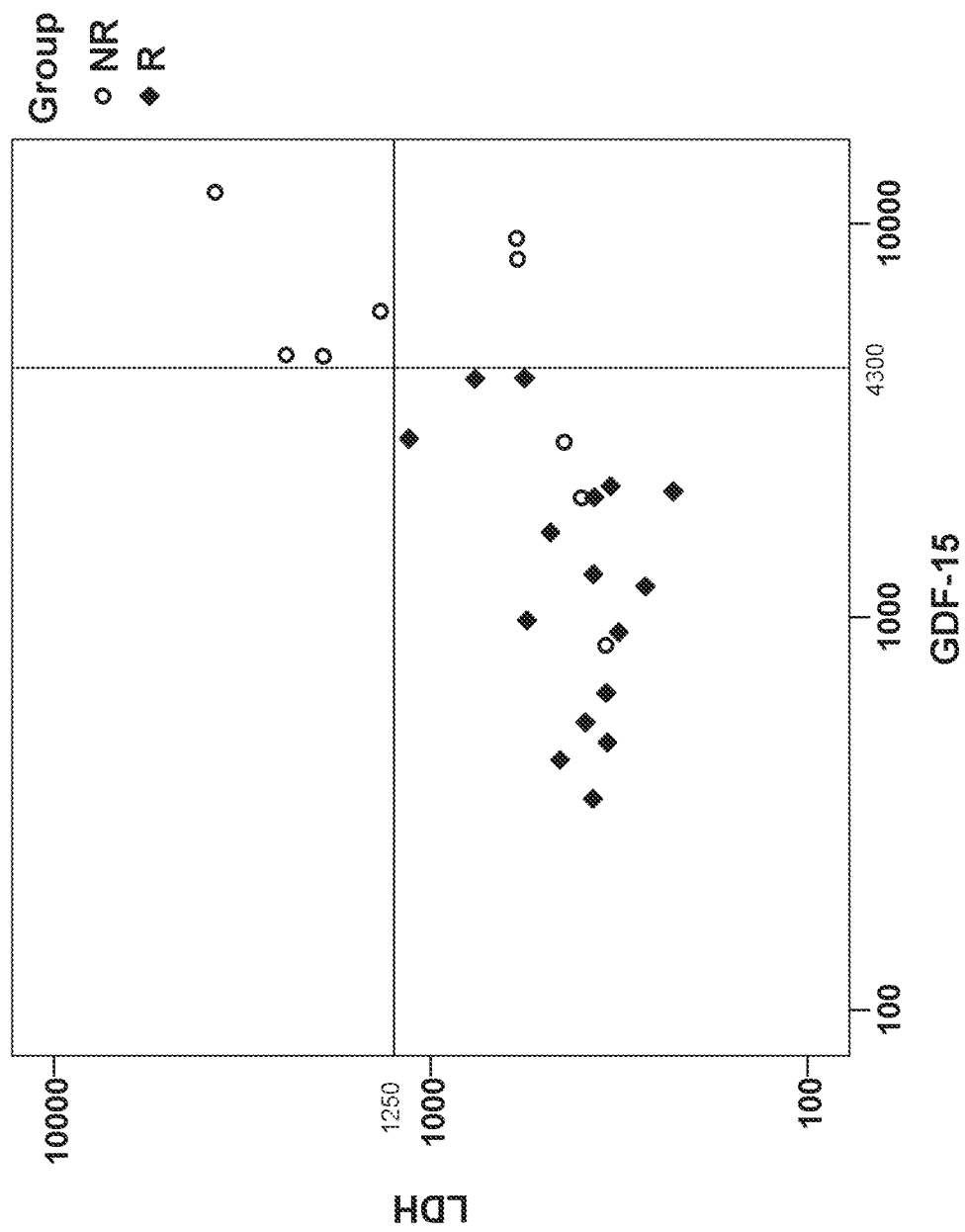

Table 7 is analogue to Table 2, except that LDH was used as continuous predictor of response to treatment (responder1) instead of GDF-15. The probability of response to treatment marginally significantly decreased with increasing values of LDH (OR<1, p<0.1). FIGS. 5A-5B show the corresponding data on responders/non-responders as well as the probability of response to treatment predicted by the model.

In order to determine, whether GDF-15 is the better predictor of response to treatment (responder1) than LDH, two additional models were fitted: a model containing both markers as predictors (which automatically only includes patients with measurements on both markers), and a model with GDF-15 as the only predictor but also only using the patients with a measurement of LDH. Then, Akaike's information criterion (AIC) was calculated for all three models (Table 8). A smaller AIC indicates a more efficient model. In fact, the AIC of the model with GDF-15 was smaller than the AIC of the model with LDH as predictor. The model with GDF-15 only even has a smaller AIC than the model with both predictors, indicating that LDH as an additional predictor does not improve the model. Of course, the model with both predictors cannot explain the response to treatment worse, but as a measure of "model efficiency", the AIC penalizes models with predictors that do not improve the model consider-ably and favours simpler models. An alternative model comparison was done by analysis of deviance (similar to analysis of variance but for generalized linear models), i.e., comparing the difference in the deviance explained between a the more complex model with both predictors and both of the simpler models with only one of the predictors (corresponding to a reduction of the model by either LDH or GDF-15). Removing GDF-15 from the more complex model resulted in a significant reduction in the deviance explained (P=0.02) whereas removing LDH did not (P=0.41).

TABLE 7

Table 7: Odds ratio (OR) estimates from the Generalized Linear Model with response to treatment (responder 1, as defined in file A) as outcome variable and LDH as continuous predictor. The analysis included samples from 25 patients.

|  | Estimate (OR) | 95% CI | z | p |
|---|---|---|---|---|
| (Intercept) | 9.741 | [2.055, 89.308] | 2.44 | 0.0146 |
| LDH | 0.997 | [0.994, 0.999] | −1.79 | 0.0727 |

TABLE 8

Table 8: Model comparison based on Akaike's information criterion (AIC) of which smaller values indicate a more efficient model, df: degrees of freedom. All models included samples from 25 patients.

|  | df | AIC |
|---|---|---|
| Model with LDH and GDF-15 | 3.00 | 25.10 |
| Model with LDH only | 2.00 | 28.55 |
| Model with GDF-15 only | 2.00 | 23.77 |

FIG. 5A shows the probability of response to treatment (responder 1) as predicted by the Generalized Linear Model model using LDH as continuos predictor. Circles show the data, the curve shows the model. The vertical line indicates the LDH concentration where the probability of treatment response is 0.5. The patient cohort was identical. However, reliable determination of LDH levels failed in four patients due to hemolysis. FIG. 5B shows a graphical representation of responders and non-responders and their respective hGDF-15 and LDH levels. When cut-off values are selected to cover all responders, testing based on GDF-15 allows for identification of 6 (out of 9) non-responders whereas analyses based on LDH levels can only discriminate 4 (out of 9) non-responders. For LDH testing, 4 hemolytic samples had to be excluded which causes loss of data.

Summary:

Taken together, the above statistical results of Example 1 showed that the likelihood of a response to the treatment significantly decreases with increasing hGDF-15 levels in the patient sera. For instance, the odds ratio of 0.389 shown in Table 2 indicates that if hGDF-15 serum levels are increased by 1 ng/ml, the likelihood of a response to the treatment decreases to the 0.389-fold value of the original value, i.e. it decreases by about 60%. If hGDF-15 serum levels are increased by 2 ng/ml, the likelihood of a response to the treatment decreases to the 0.389×0.389-fold=0.151-fold value of the original value, i.e. it decreases by about 85%.

The results of Example 1 suggest that hGDF-15 acts to negatively affect the patients' responses to the treatment with immune checkpoint blockers. Thus, according to the invention, an inhibitor of hGDF-15 will be useful to inhibit the negative effects of hGDF-15 on the patients' responses to the treatment with immune checkpoint blockers, and to improve the patients' responses to the treatment with immune checkpoint blockers not only in melanoma, but in all of the solid cancers referred to herein.

Example 2: GDF-15 Levels Inversely Correlate with $CD8^+$ Tumor Infiltrating Lymphocytes (TILs) in Metastases of Different Tumor Entities In order to identify a mechanism of hGDF-15 that contributes to the negative effect of hGDF-15 on the patients' responses, brain metastases from different solid tumors were analyzed for the expression of hGDF-15 and for the presence of cells of the immune system:

Tissue Specimen and Tissue Processing:

Formalin-fixed and paraffin-embedded (FFPE) tissue from archived brain metastases was analyzed, which was collected and processed as tissue micro arrays (TMAs). All specimens were obtained either from the UCT tumor bank (Goethe-University, Frankfurt am Main, Germany, member of the German Cancer Consortium (DKTK), Heidelberg, Germany and German Cancer Research Center (DKFZ), Heidelberg, Germany) or from the cancer registry tumor bank ""Blut-und Gewebebank zur Erforschung des malignen Melanoms" (Department of Dermato-oncolgy, University Hospital Tubingen, Germany). Approval for this study was conferred by two independent ethical committees (Ethics committee UCT Frankfurt/Goethe University Frankfurt am Main, Germany: project numbers: GS 4/09; SNO_01-12; Ethics committee University of Tubingen project number: 408/2013B02). In total, 190 patients with brain metastases were investigated including: melanoma (n=98), NSCLC (n=33), breast carcinoma (n=18), RCC (n=10), SCLC (n=7), colorectal carcinoma (n=7), carcinomas which were not otherwise specified (carcinoma NOS n=11) and specimens of rare tumors summarized as others (n=6). Survival data of 155 patients (survival time after tumor resection) were collected, additionally the number of brain metastases in 169 patients and brain metastases size in a subcohort of 55 melanoma patients was analyzed.

Immunohistochemistry:

Immunohistochemistry for all antibodies was performed using 3 μm thick slides and standard protocols on the automated IHC staining system Discovery XT (RocheNentana, Tucson, Ariz., USA). The following antibodies were used: anti GDF-15 (HPA011191, dilution 1:50, Sigma/Atlas, protocol #730), CD3 (clone A0452, dilution 1:500, DAKO, Glostrup, Denmark), CD8 (clone C8/144B, dilution 1:100, DAKO, Glostrup, Denmark), PD-1 (clone NAT105; dilution 1:50; Abcam, Cambridge, United Kingdom), PD-L1 (E1L3N; dilution 1:200; Cell Signaling, Boston, U.S.A.), FOXP3 (clone 236A/E7; dilution 1:100; eBioscience, San Diego, U.S.A.). Slides were counterstained with hematoxylin and mounted.

Statistical Analyses:

All samples were scored according to the frequency of positive cells related to all cells (as percentage) on the stained TMA core. For hGDF-15 expression, a score as previously described in detail [21,22] was used: frequency 0-1% score 0; 1-10% score 1; 10-25% score 2; 25-50% score 3; >50% score 4; additionally the frequency score was multiplied with the intensity of staining (1 weak staining, 2 moderate staining, 3 strong staining), finally resulting in the ordinal scaled hGDF-15 score (0, 1, 2, 3, 4, 6, 8, 9, 12). Ordinal scaled variables were compared with non-parametric Wilcoxon/Kruskal-Wallis-Test and Dunn's method to correct for multiple testing. For continuous variables, means were compared between different brain metastases entities using ANOVA, followed by Tukey-Kramer HSD post-hoc Test. For correlation analyses of brain metastases size and marker expression, a linear fit was performed followed by ANOVA, in case of ordinal scaled variables, Spearman's rho correlation analysis was used. A significance level of p<0.05 was set for all statistical analyses.

All statistical analyses were performed using JMP8 and JMP11 (SAS, Cary, U.S.A.), additional graphics were created with Prism 6 (GraphPad Software, La Jolla, U.S.A.).

Figure 6:
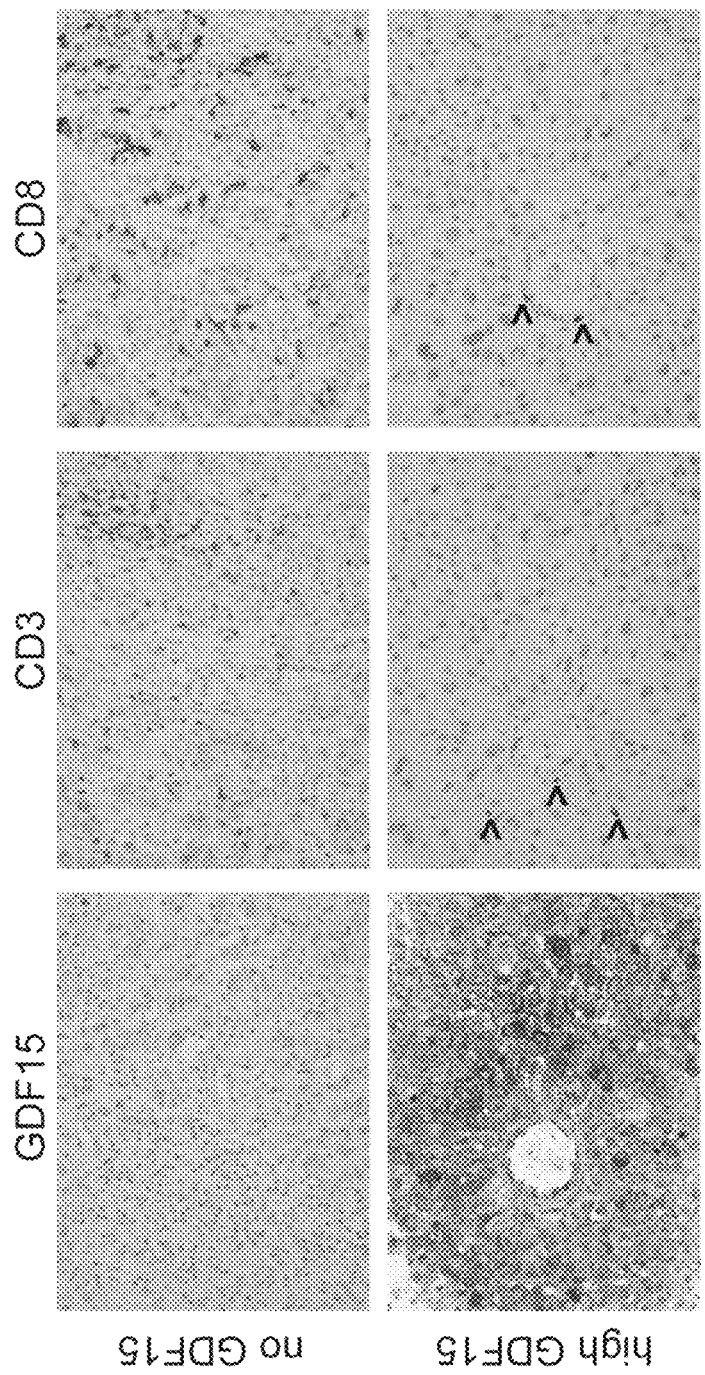
FIG. 6: This Figure shows exemplary tissue sections from melanoma brain metastases having no (upper panel) or high (lower panel) GDF-15 immunoreactivity, which were stained by immunohistochemistry for GDF-15 and for the T-cell marker proteins CD3 and CD8, respectively, as indicated in the Figure. CD3 and CD8-positive cells are indicated by arrows in the high GDF-15 samples. The CD3 and CD8 stainings were made from the same area of serial sections (however not from the identical section).

Results:

FIG. 6 shows exemplary tissue sections from melanoma brain metastases having high no (upper panel) or high (lower panel) GDF-15 immunoreactivity, which were stained by immunohistochemistry for GDF-15 and for the T-cell marker proteins CD3 and CD8, respectively, as indicated in the Figure. In the section with no GDF-15 expression, the numerous infiltrating immune cells are seen as dark spots. In the picture showing the metastasis expressing high levels of GDF-15, the scarce infiltrating immune cells are depicted by arrows (CD3 and CD8-positive cells are indicated by arrows). As can be seen from the Figure, it was surprisingly found that in the tissue section with high hGDF-15 immunoreactivity (lower panel), the number of $CD3^+$ and $CD8^+$ cells was strongly reduced compared to the tissue section with no hGDF-15 immunoreactivity (upper panel). Of note, other markers stained like PD-L1, PD-1 all showed a positive correlation with the number of tumor-infiltrating $CD3^+$ and $CD8^+$ T cells.

Figure 7A:
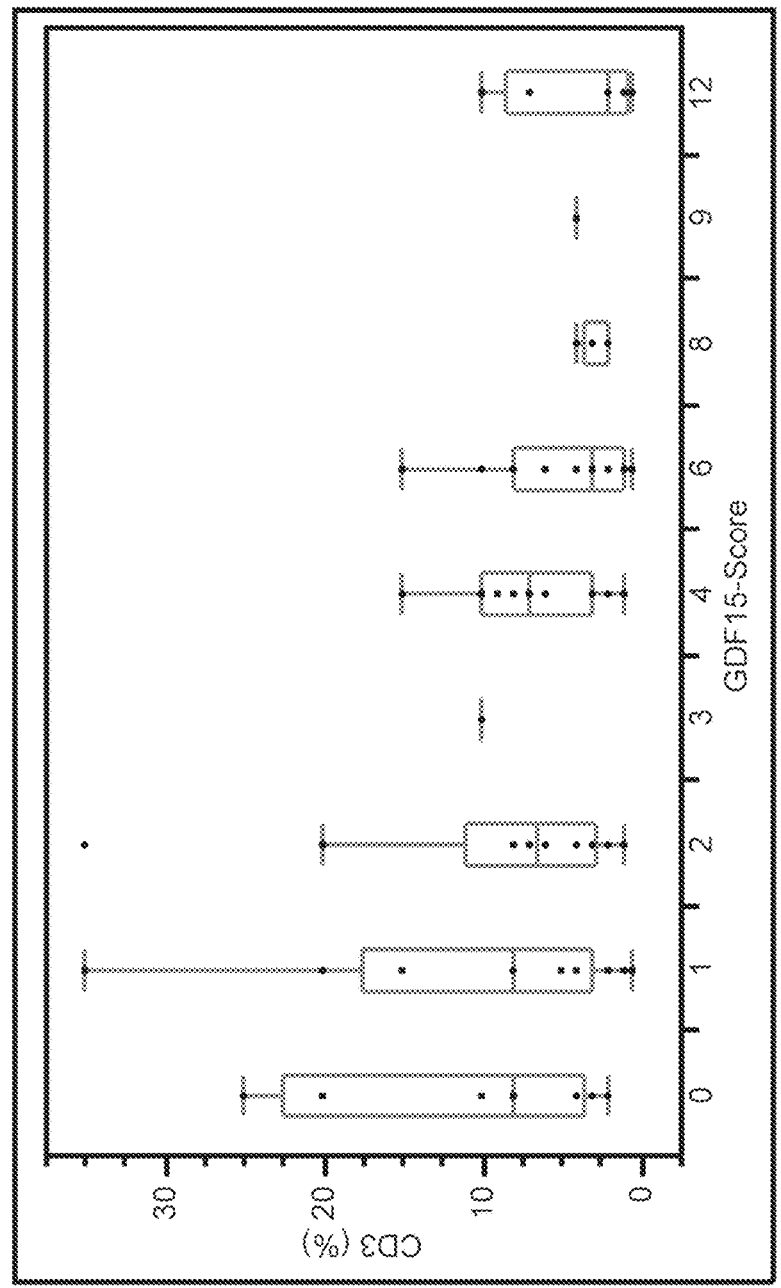
FIGS. 7A-7B: This Figure shows a plot of the percentage of $CD3^+$ cells against the GDF-15 score across different melanoma brain metastases (7A) and a plot of the percentage of $CD8^+$ cells against the GDF-15 score across different melanoma brain metastases (7B).

Therefore, it was next analyzed whether there exists an inverse correlation between hGDF-15 levels and the percentage of $CD3^+$ T cells across different melanoma brain metastases. FIG. 7A shows a plot of the percentage of $CD3^+$ cells against the GDF-15 score (obtained as described above in the "statistical analyses" section). As indicated in FIG. 7A, there was a statistically significant inverse correlation between the percentage of $CD3^+$ cells and the GDF-15 score (p=0.0015).

Figure 7B:
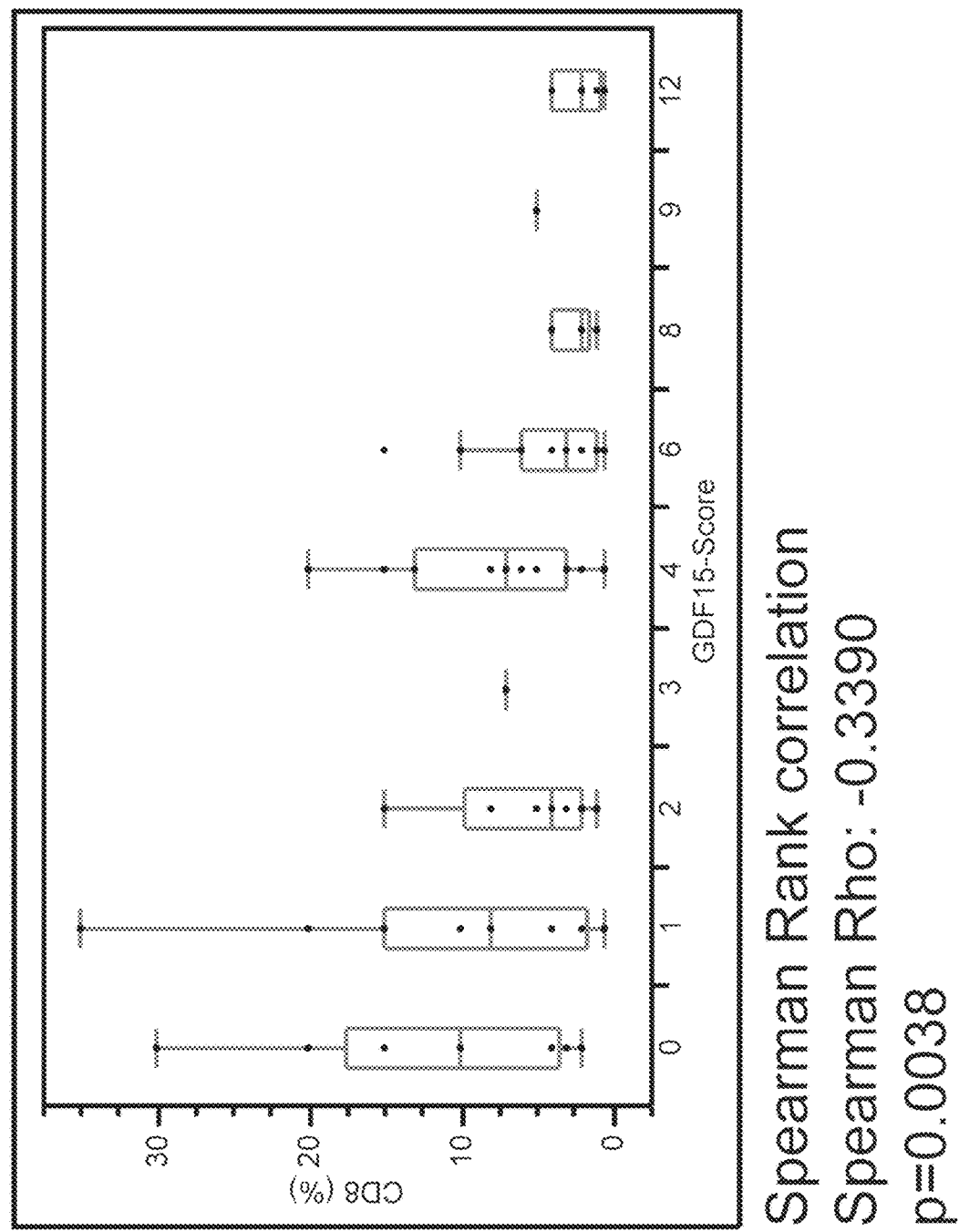

Similarly, it was also analyzed whether there exists an inverse correlation between hGDF-15 levels and the percentage of $CD8^+$ T cells across different melanoma brain metastases. FIG. 7B shows a plot of the percentage of $CD8^+$ cells against the GDF-15 score (obtained as described above in the "statistical analyses" section). As indicated in FIG. 7B, there was a statistically significant inverse correlation between the percentage of $CD8^+$ cells and the GDF-15 score (p=0.0038).

Correlating GDF-15 with FOXP3, in contrast, gave no statistically significant result according to Spearman's rank correlation coefficient (rho) test (p=0.8495 across different tumor entities; p=0.2455 when assessing only melanoma metastases).

Figure 8:
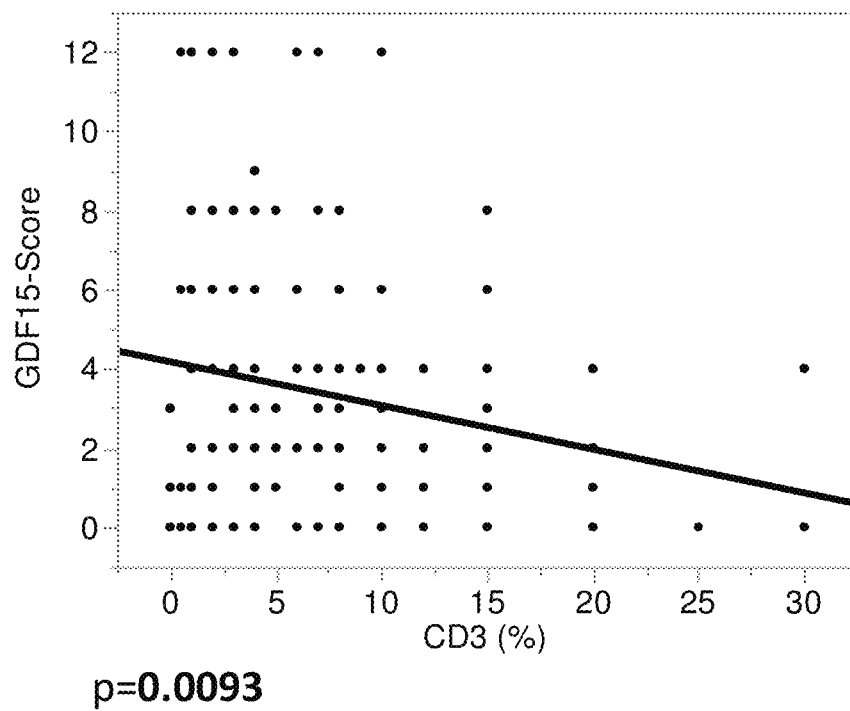
FIG. 8: This Figure shows a plot of the GDF-15 score against the percentage of $CD8^+$ and $CD3^+$ T cells, respectively, in brain metastases from different tumor entities (melanoma, CRC, RCC, NSCLC and SCLC).
Figure 8:
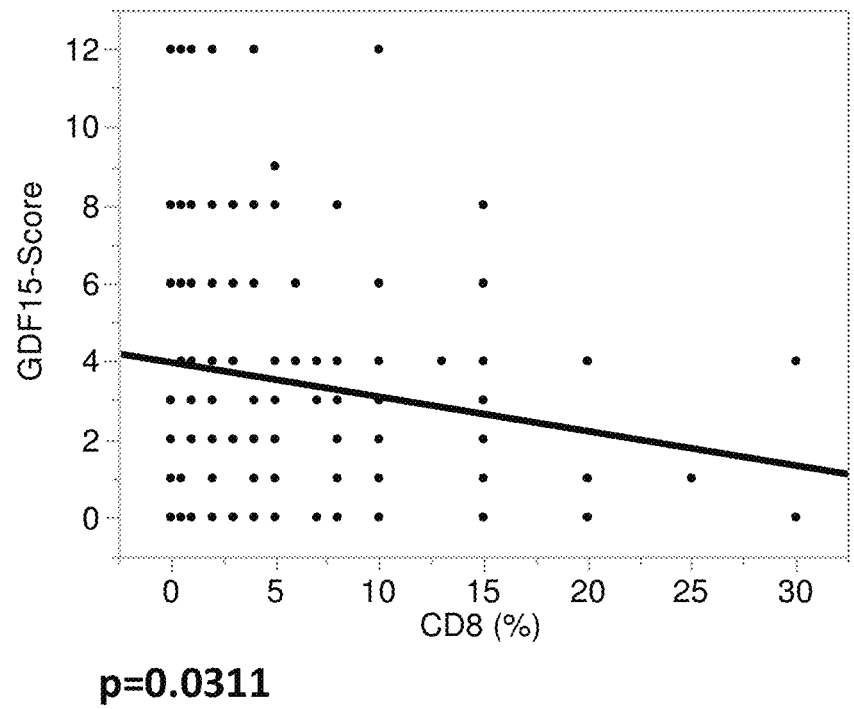

Finally, it was also analyzed whether there exists an inverse correlation between hGDF-15 levels and the percentages of $CD8^+$ and $CD3^+$ T cells across brain metastases from different tumor entities. FIG. 8 shows a plot of the GDF-15 score against the percentage of $CD8^+$ and $CD3^+$ T cells, respectively, in 168 (for CD3) or, respectively, 169 (for CD8) brain metastases from different tumor entities (melanoma, CRC, RCC, breast cancer, NSCLC and SCLC). The plot was obtained as described above in the "statistical analyses" section. As indicated in FIG. 8, there was a statistically significant inverse correlation between the percentage of $CD8^+$ cells and the GDF-15 score (p=0.0311) as well as a statistically significant inverse correlation between the percentage of $CD3^+$ cells and the GDF-15 score (p=0.0093). Other markers (PD-L1, PD-1, FOXP3) again showed positive correlations with CD3 and CD8 T cell infiltration.

Summary:

The above results show that there is not only an inverse correlation of hGDF-15 with the percentage of T-cells expressing the general T-cell marker protein CD3 in the metastases, but also an inverse correlation with the percentage of $CD8^+$ T lymphocytes in the metastases. This is noteworthy, because the presence of $CD8^+$ T lymphocytes was previously shown to be specifically required for tumor regression after immune checkpoint inhibition with an anti-PD-1 antibody (Tumeh et al., Nature. 2014 Nov. 27; 515 (7528):568-71).

Thus, according to the invention, therapeutic inhibition of hGDF-15 can be used to increase the percentage of $CD8^+$ T lymphocytes in solid tumors including tumor metastases. This increase of $CD8^+$ T lymphocytes in the solid tumors can be used for therapy of the solid tumors. In a non-limiting aspect of the invention, a particularly favorable therapeutic combination is the combination of an hGDF-15 inhibitor with an immune checkpoint blocker. An advantageous effect of this combination is that inhibition of hGDF-15 will increase the percentage of $CD8^+$ T lymphocytes in the solid tumors and thereby lead to a synergistic therapeutic effect with immune checkpoint inhibition. The invention can thus be applied to all of the solid tumors as referred to in the preferred embodiments.

Example 3: GDF-15 Decreases Adhesion of T Cells to Endothelial Cells

The inventors next set out to determine how hGDF-15 affects the percentage of T cells in the solid tumors.

A step which is required for the invasion of T cells from the blood stream into the tumor tissue is that the T cells must first adhere to the endothelium before they can enter the tumor. In order to simulate this step and to assess whether this step could be affected by hGDF-15, the inventors used a model system which measures the adhesion of T cells to Human Umbilical Vein Endothelial Cells (HUVEC):

T Cell Flow/Adhesion Experiment (on HUVEC):

Day 1:
  a. μ-slides VI 0.4 (ibidi GmbH, Germany) were coated with fibronectin (100 μg/mL): 30 μL per loading port. They were incubated for 1 h at 37° C. (or a pre-coated slide was used).
  b. Fibronectin was aspirated, followed by a wash with HUVEC medium.
  c. HUVECs were trypsinized from a 6-well plate (count: $2\times10^5$/mL (2 mL total))
  d. They were washed and diluted to $1\times10^6$ cells/mL
  e. 30 μL of HUVECs were applied in loading ports of the μ-slide VI and checked under a microscope
  f. The μ-slide VI was covered with a lid and incubated at 37° C., 5% $CO_2$i Day 2:
  a. HUVECs were activated with TNFα (10 ng/mL) and IFNγ (10 ng/mL) in channels 2-5 (see table below): All media were aspirated from the channels and replaced with cytokine-containing pre-warmed media.

Day 3:
  a. T cells were isolated (negative isolation of pan T cells).
  b. T cells were pre-incubated in well 1 ($1\times10^6$ cells/mL) with or without GDF-15 (100 ng/mL) for 1 h.
  c. HUVECs were pre-incubated in channels 4 and 5 with GDF-15 (100 ng/mL) for 1 h: All medium in loading ports was aspirated, and both loading ports were filled with pre-warmed medium containing GDF15.
  d. A stage top incubator next to the microscope was pre-warmed, and a gas-mix was connected (5% $CO_2$, 16% $O_2$, 79% $N_2$).

e. 3×50 mL syringes were prepared:
  i. T cells (1×10$^6$ cells/mL): 1 mL
  ii. T cells GDF15 (1×10$^6$ cells/mL): 1 mL
  iii. Medium
f. Syringe 1 was connected to channel 1 (see table below) and the flow was started (0.5 dyn/cm$^2$: 0.38 mL/min=22.8 mL/h).
g. T cells were flowed for 3 min and in the meantime, 10 fields of view were predefined on the microscope.
h. Each field of view was video-imaged for 5 s.
i. The remaining channels were assessed in analogy to channel 1 (f-h) with the T cell samples as indicated in the table below.

| Channel # | endothelial cells | T cells in flow | comments |
|---|---|---|---|
| 1 | HUVEC unstimulated | T cells | [negative control] |
| 2 | HUVEC stimulated | T cells | [positive control] |
| 3 | HUVEC stimulated | T cells GDF-15 | |
| 4 | HUVEC stimulated GDF-15 | T cells | |
| 5 | HUVEC Stimulated GDF-15 | T cells GDF-15 | |

Recombinant GDF-15 was obtained from Invigate GmbH, Jena, Germany.

Statistical Analysis:

All data were compared using Mann-Whitney test for testing of non-normally distributed data. Values of p<0.05 were considered to be statistically significant.

Results:

The results of the experiment are shown in FIGS. 9A-9D. These Figures show analyses of several adhesion parameters, namely
  a. the number of rolling T cells per field of view per second (9A; the data were obtained from channel #3 ("GDF-15") and channel #2 ("control")), which reflects a form of moderate adhesion of the T cells to the endothelial cells,
  b. the rolling speed of the T cells (measured in pixels per 0.2 seconds) (9B; the data were obtained from channel #3 ("GDF-15") and channel #2 ("control")), which increases with decreasing adhesion between the T cells and the endothelial cells, and
  c. the number of adhering cells per field of view (9C; the data were obtained from channel #3 ("GDF-15") and channel #2 ("control"); and 9D).

Figure 9A:
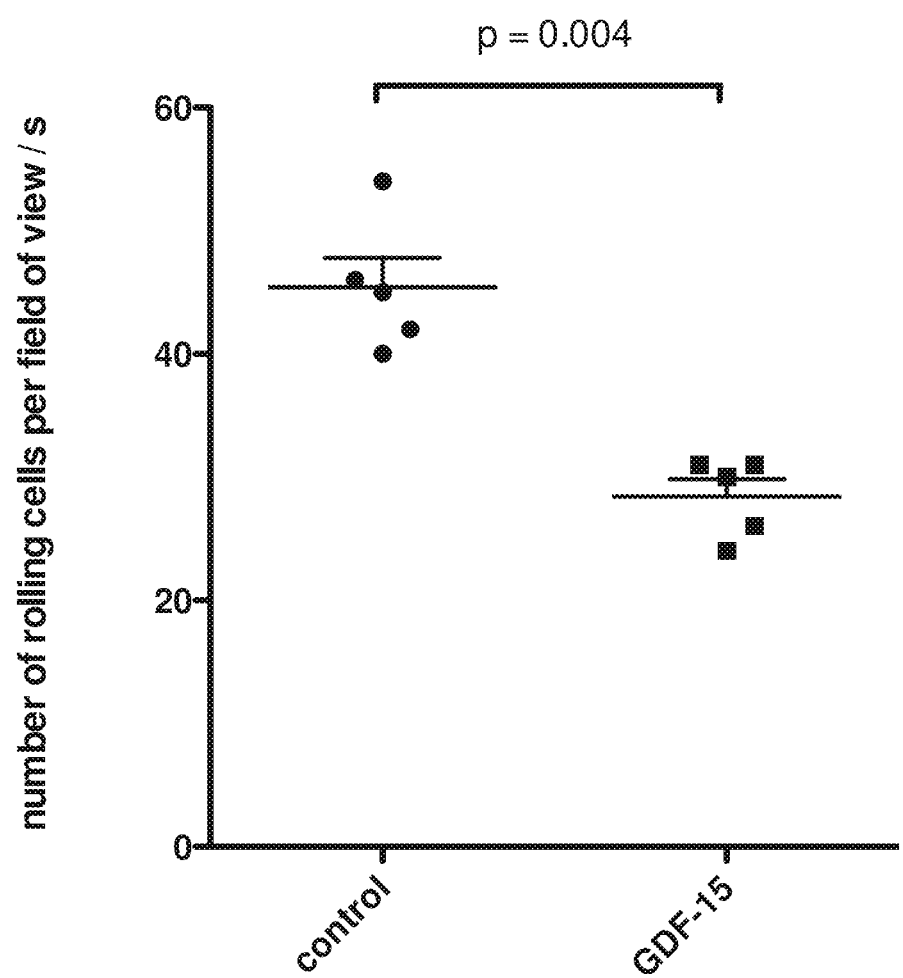
FIGS. 9A-9D.
Figure 9B:
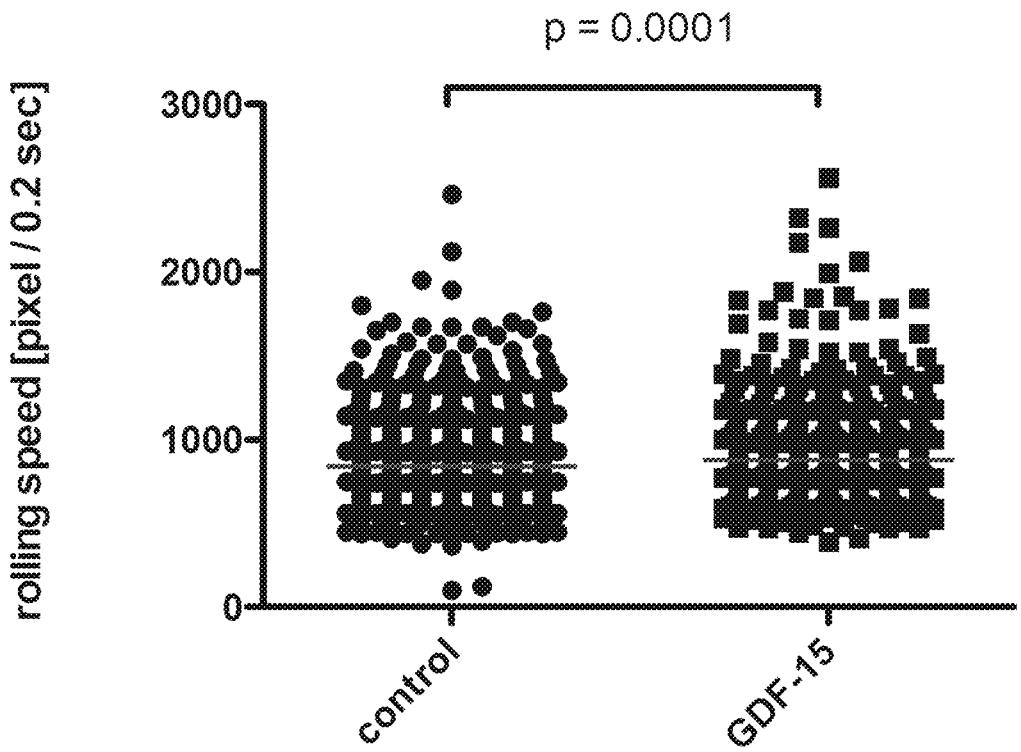
Figure 9C:
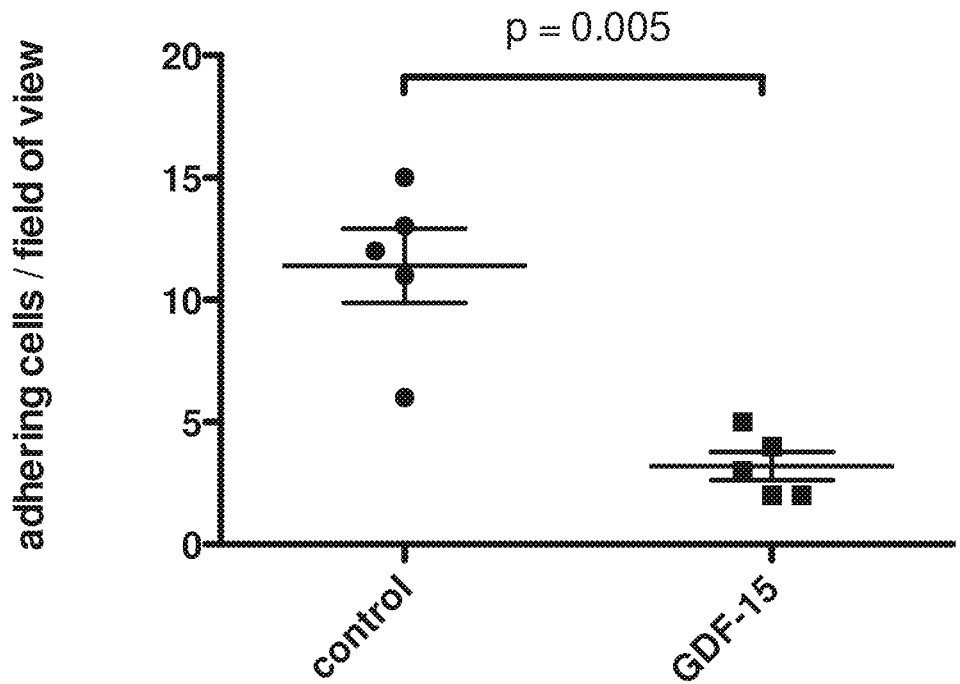

As can be seen from FIG. 9C, it was found that treatment of the T cells with hGDF-15 significantly decreases the adhesion to the endothelial cells, as reflected in the number of adhering cells per field of view. Similar results were obtained when analyzing adhesion by counting the numbers of rolling T cells (FIG. 9A). Furthermore, and consistent with the above results, it was found that treatment of the T cells with hGDF-15 significantly increases the rolling speed, indicating a decrease in the interaction time between the T cells and the endothelial cells, and also indicating a reduced adhesion between the T cells and the endothelial cells (FIG. 9B).

Figure 9D:
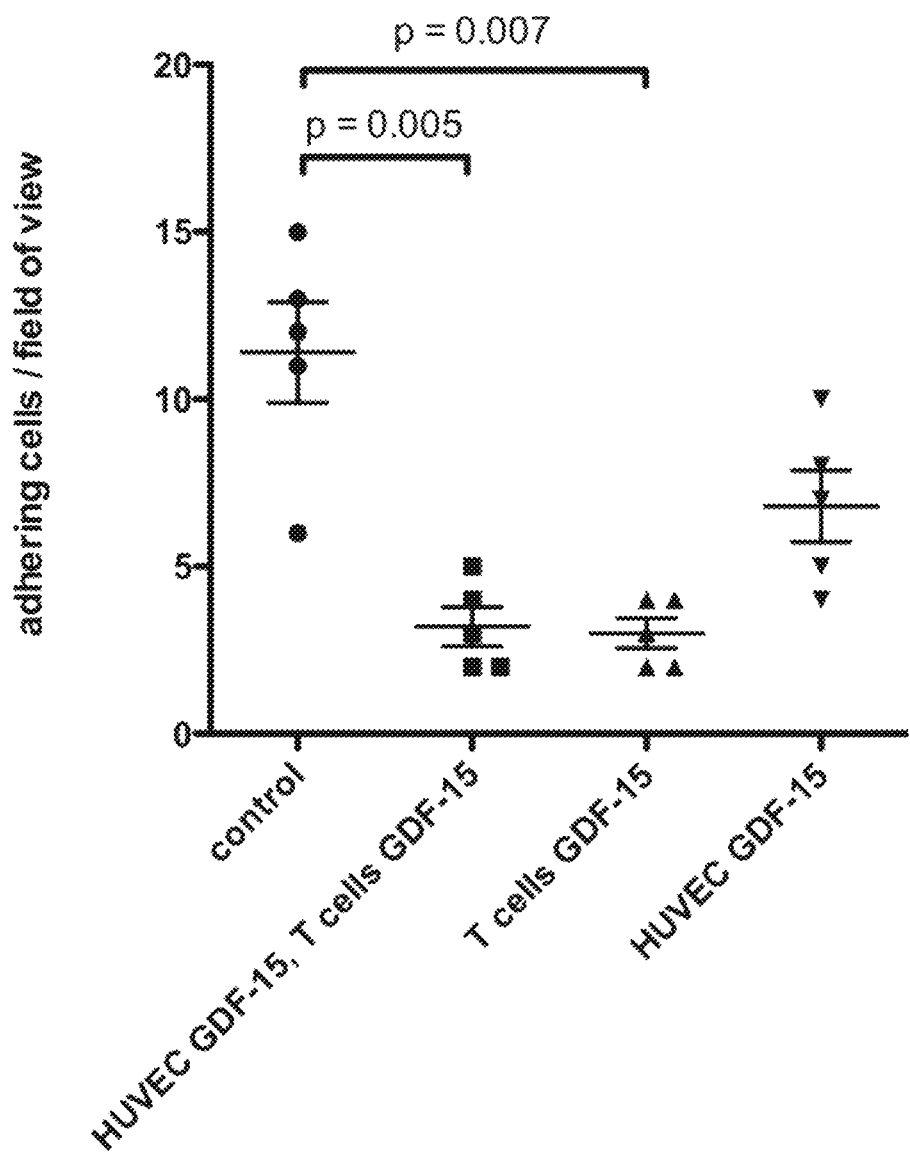

The inventors next analyzed which cells were targeted by hGDF-15 (FIG. 9D). In the sample where only HUVEC were treated with hGDF-15, a moderate decrease in the adhesion of the T cells to the endothelial cells (HUVECs) was observed. In contrast, a strong decrease in the adhesion of the T cells to the endothelial cells (HUVECs) was observed when either only the T cells were treated with hGDF-15, or when both the T cells and the endothelial cells (HUVECs) were treated with hGDF-15. These results indicate that hGDF-15 acts both on the T cells and on the endothelial cells, but they also indicate that the main adhesion effect of hGDF-15 is an effect on the T cells.

Next the inventors tested whether effects of hGDF-15, which is secreted by tumor cells, on T-cell adhesion could be inhibited with an hGDF-15 inhibitor. In order to test this, the inventors used an hGDF-15-secreting melanoma cell line, UACC257:

T Cell Flow/Adhesion Experiment (on HUVEC) in the Presence or Absence of GDF-15 in Tumor Cell Supernatant:

Day 1:
  a. One μ-slide VI 0.4 (ibidi GmbH, Germany; from now on referred to as μ-slide) were coated with fibronectin (100 μg/mL): 30 μL per loading port. They were incubated for 1 h at 37° C. (or a pre-coated slide was used).
  b. Fibronectin was aspirated, followed by a wash with HUVEC medium.
  c. HUVECs were trypsinized from a 6-well plate (count: 2×10$^5$/mL (2 mL total))
  d. They were washed and diluted to 1×10$^6$ cells/mL
  e. 30 μL of HUVECs were applied in loading ports of the μ-slide and checked under a microscope
  f. The μ-slide was covered with a lid and incubated at 37° C., 5% CO$_2$.

Day 2:
  a. HUVECs were activated with TNFα (10 ng/mL) and IFNγ (10 ng/mL) in channels 2-5 of the μ-slide (see table below): All media were aspirated from the channes and replaced with cytokine-containing pre-warmed media.

Day 3:
  a. T cells were isolated (negative isolation of pan T cells).
  b. In parallel 24 wells of an 96-well ELISA-plate (Nunc maxisorb) were coated with 200 μL anti-GDF-15 (10 μg/mL diluted in PBS), incubated for 45 min and then washed with PBS.
  c. To deplete supernatant from the melanoma cell line UACC257 which secrets GDF-15 (data not shown) from GDF-15 the supernatant was incubated in wells of the ELISA-plate (see b.) that were pre-coated with anti-GDF-15.
  d. As a control supernatant of the melanoma cell line UACC257 was incubated in wells of the ELISA-plate (see b.) that were not pre-coated with anti-GDF-15.
  e. T cells were pre-incubated in a 12-well cell culture plate (1×10$^6$ cells/mL) with GDF-15 (100 ng/mL), without GDF-15, in supernatant of the melanoma cell line UACC257 depleted from GDF-15 (see c.) or in supernatant of the melanoma cell line UACC257 containing GDF-15 (see d.) for 1 h.
  f. A stage top incubator next to the microscope was pre-warmed, and a gas-mix was connected (5% CO$_2$, 16% O$_2$, 79% N$_2$).
  g. 4×2 mL tubes of a microfluidic flow system were prepared:
    i. T cells (1×10$^6$ cells/mL): 1 mL
    ii. T cells GDF15 (1×10$^6$ cells/mL): 1 mL
    iii. T cells UACC 257 (containing GDF-15)
    iv. T cells UACC 257 depleted from GDF-15
  h. Tube 1 was connected to channel 1 (see table below) and the flow was started (0.4 mL/min=24 mL/h).
  i. T cells were flowed for 3 min and in the meantime, 5 fields of view were predefined on the microscope.
  j. Each field of view was video-imaged for 5 s.

k. The remaining channels were assessed in analogy to channel 1 (f-h) with the T cell samples as indicated in the table below.

| channel # | endothelial cells | T cells in flow | comments |
|---|---|---|---|
| 1 | HUVEC unstimulated | T cells | [negative control] |
| 2 | HUVEC stimulated | T cells | [positive control] |
| 3 | HUVEC stimulated | T cells GDF-15 | |
| 4 | HUVEC stimulated | T cells UACC 257 | |
| 5 | HUVEC stimulated | T cells UACC 257 depleted from GDF-15 with anti GDF-15 | |

Recombinant GDF-15 was obtained from Invigate GmbH, Jena, Germany.

Figure 10A:
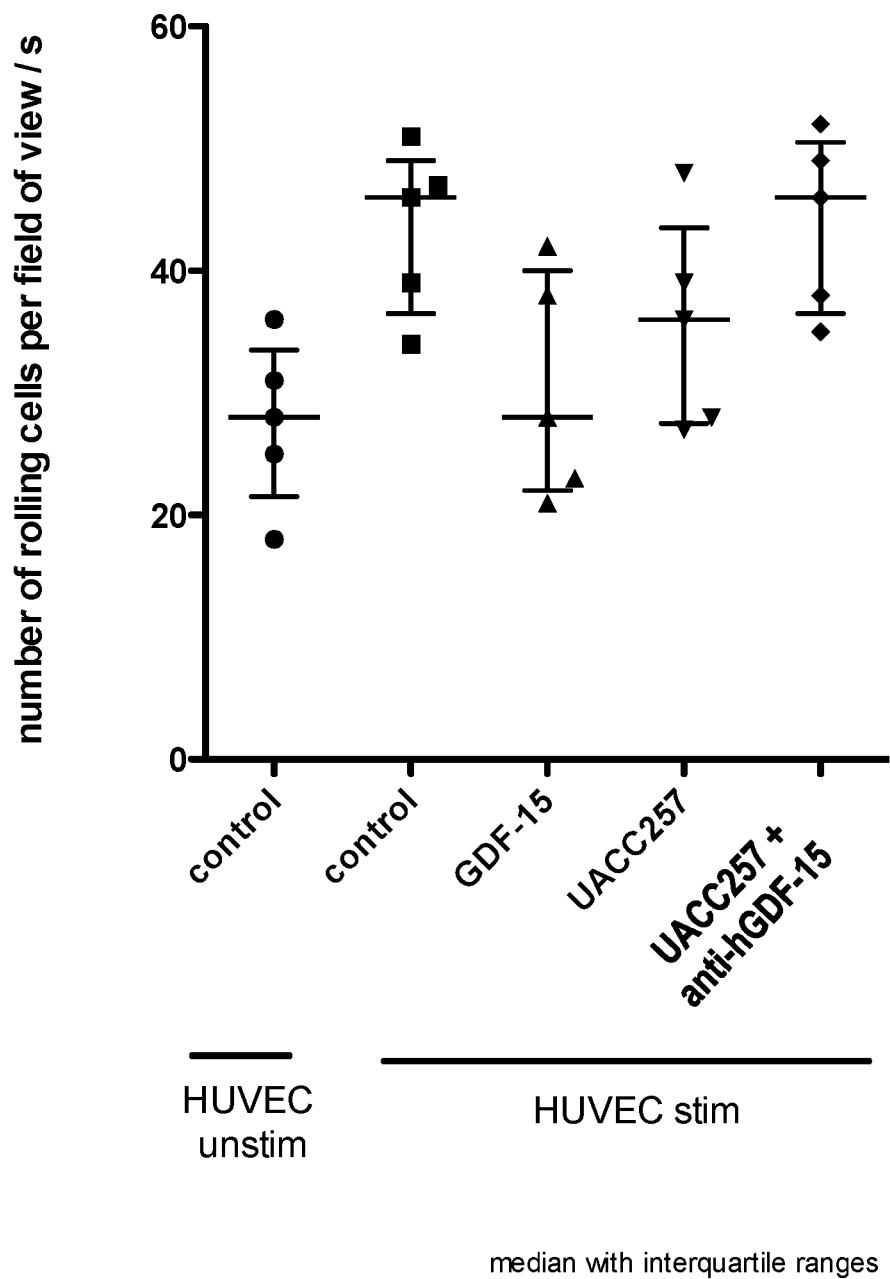
FIGS. 10A-10B.

Results:

The results of the experiment are shown in FIG. 10A. This Figure shows analyses of the number of rolling T cells per field of view per second. The data were obtained from channel #1 (control T cells on unstimulated HUVEC as "neg. control"), channel #2 (control T cells on stimulated HUVEC as "pos. control"), channel #3 ("GDF-15") channel #4 ("UACC 257": T cells cultured in the supernatant of UACC 257 melanoma cells containing secreted GDF-15) and channel #5 ("UACC257+anti-hGDF-15": T cells cultured in the supernatant of UACC 257 melanoma cells depleted from secreted GDF-15 with anti GDF-15 B1-23)

In comparison to T cells flown over unstimulated HUVEC ("neg. control"; median=28 rolling cells per field of view per second) flowing of T cells over stimulated HUVEC ("pos. control") increased the number of rolling cells per field of view per second (median=46). Treatment of the T cells with hGDF-15 substantially decreases the number of rolling cells per field of view per second (median=29). Also, pre-incubation of the T cells with supernatant of the melanoma cell line UACC257 that secretes GDF-15 substantially decreases the number of rolling cells per field of view per second (median=36) as compared to T cells flowing over stimulated HUVEC ("pos. control"). I contrast to this, pre-incubation of the T cells with supernatant of the melanoma cell line UACC257 depleted from secreted GDF-15 with anti GDF-15 B1-23 resulted in numbers of rolling cells per field of view per second (median=45) that were comparable to T cells flowing over stimulated HUVEC ("pos. control").

Thus, according to the invention, hGDF-15 inhibitors can be used to increase adhesion of T-cells including CD8+ cells to endothelial cells, e.g. in the treatment of solid cancers.

Furthermore, the above assay provides a simple in vitro system which can be used to determine whether a substance of interest is an hGDF-15 inhibitor.

Summary:

This example shows that GDF-15, including GDF-15 secreted by tumor cells, decreases adhesion of T cells to endothelial cells. Therefore, according to the invention, a treatment with hGDF-15 inhibitors can be used to increase adhesion of T cells including CD8+ T cells to endothelial cells. Such treatment will increase entry of T cells including CD8+ T cells from the blood stream into solid cancers. The increased percentage of CD8+ T cells in solid cancers, which will result from such treatment with hGDF-15 inhibitors, is advantageous for, and can be used in, cancer therapy, e.g. cancer immunotherapy. Since the entry of CD8+ T cells into solid cancers and the presence of these CD8+ T cells in the solid cancers is particularly advantageous for therapeutic approaches using immune checkpoint blockers, a particularly advantageous use of hGDF-15 inhibitors according to the invention is their use in combination with immune checkpoint blockers.

Flow-Adhesion Assay Including Antibody Neutralization by Antibodies H1L5 (Humanized B1-23) and 01G06 and 03G05 (Humanized Anti-GDF-15 Antibodies Engineered According to Sequences According to WO 2014/100689)

This experiment was performed in order to further confirm the effects observed above, including the finding that hGDF-15 inhibitors can be used to increase T cell adhesion to endothelial cells or the rolling of T cells.

Experimental Procedures:

The flow/adhesion assay was conducted as described above in the present Example. T-cells were pre-incubated with 100 ng/ml GDF-15 for 1 hour or with 100 ng/ml GDF-15, which was pre-incubated with 10 µg/ml antibody for 1 hour. The following Anti-GDF-15 antibodies were used: H1L5 (Humanized B1-23), 01G06 and 03G05 (Humanized Anti-GDF-15 Antibodies Engineered According to Sequences from WO 2014/100689).

Figure 10B:
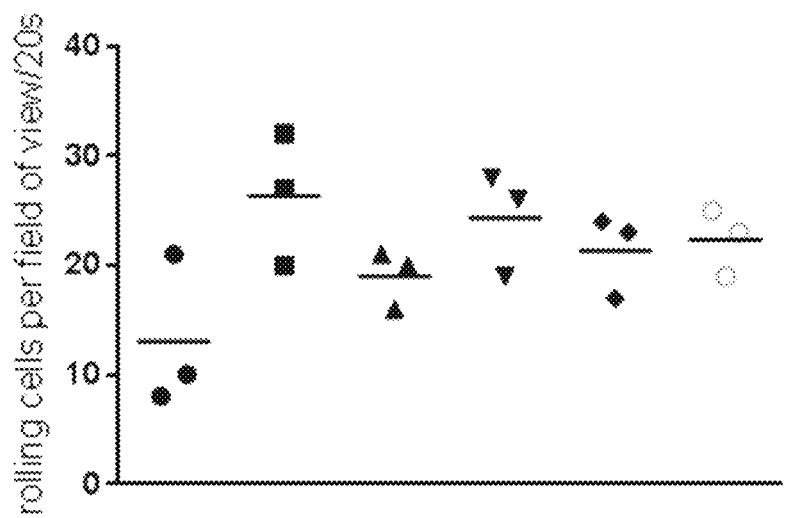

Results:

The results are shown in FIG. 10B. In comparison to T cells flown over unstimulated HUVEC (negative control), flowing of T cells over stimulated HUVEC (positive control) increased the number of rolling cells per field of view per 20 seconds. Treatment of the T cells with hGDF-15 substantially decreased the number of rolling cells per field of view per 20 seconds. In contrast to this, pre-incubation of the T cells with hGDF-15, which was pre-incubated with the anti GDF-15 antibodies H1L5 (Humanized B1-23), 01G06 or 03G05, resulted in numbers of rolling cells per field of view per 20 seconds that were substantially increased compared to the sample where no anti-GDF-15 antibody was added. This effect was present for all of the tested anti-GDF-15 antibodies and was most pronounced for the H1L5 (Humanized B1-23) antibody, which almost completely reverted the effect of hGDF-15 on the rolling of the T cells.

Conclusions

Thus, according to the invention, hGDF-15 inhibitors can be used to increase adhesion of T-cells including CD8+ cells to endothelial cells, or the rolling of said T-cells including CD8+ cells. In accordance with the invention, hGDF-15 inhibitors will increase the percentage of CD8+ cells in solid cancers and can be used for the treatment of these cancers. These hGDF-15 inhibitors may be—but are not limited to—any known anti-GDF-15 antibodies such as the antibodies H1L5 (Humanized B1-23), 01G06 and 03G05.

Example 4: Evaluation of Anti-Tumor Efficacy of Test Antibody in Combination with Adjuvant Immunization in Syngeneic MC38$^{tg\ hGDF-15+}$ Tumor-Bearing Mice In order to evaluate whether inhibition of human growth & differentiation factor (GDF)-15 can improve the response to an immunotherapy, and in particular a response to an immunotherapy which requires CD8+ T-cells in the tumor, murine MC38 colon cancer cells were transfected to express human GDF-15 at levels similar to those found in human cancer cell lines. As assessed by enzyme-linked immunosorbent assay (ELISA, R&D Systems, Mouse GDF-15 DuoSet ELISA), MC38 cells did not express detectable levels of murine GDF-15 (detection limit: 7.81 pg/ml).

On day 0, 9 week-old female C57BL/6J mice (provided by Charles River Laboratories, BP 0109, F 69592

L'Arbresle, Cedex) were anesthetized and subcutaneously inoculated with 2×10⁵ colon MC38$^{tg\ hGDF-15}$ cells. Treatment with anti GDF-15 antibody (20 mg/kg of body weight, i.e. about 400 µg per mouse in 100 µl of phosphate-buffered saline with 0.5% bovine serum albumin) was initiated on day 0 (about 6 h after tumor cell inoculation) and repeated on days 3, 7, 10, 14, 17, and 21. On day 13, when tumors had reached a volume between 100 and 150 mm³, animals were randomized across the different treatment groups, and the respective animals were intraperitoneally injected with adjuvant (100 µg Polyinosinic:polycytidylic acid (Poly-ICLC (Hiltonol®, Oncovir, Wash. D.C., USA)) and 50 µg of InVivoMAb anti-murine(m)CD40 antibody (clone FGK4.5/FGK45)) in a total volume of 50 µl phosphate-buffered saline.

Due to its structural similarity to double-stranded RNA, which is present in some viruses and stimulates TLR3, Poly-ICLC simulates an infection. The agonistic anti-CD40 antibody provides an additional signal to antigen-presenting cells. "Licensing" of dendritic cells via stimulation of CD40 supports the activation of antigen-specific CD8⁺ T cells. Adjuvant treatment thus serves to induce tumor-specific immune cells in mice kept under specific pathogen-free conditions (Yadav Metal., Nature. 2014 Nov. 27; 515(7528): 572-6).

This adjuvant treatment therefore represents a model system for a cancer immunotherapy which requires immune cells in the tumor, and in particular CD8⁺ T-cells in the tumor. Thus, it is a model system which is suitable to further confirm that a treatment with an hGDF-15 inhibitor such as an anti-hGDF-15 antibody synergizes with cancer immunotherapy, including a cancer immunotherapy that requires CD8⁺ T-cells in the tumor.

To summarize, the following animal groups (10 mice per group) were investigated:
  vehicle group without adjuvant immunization
  group treated with anti hGDF-15 antibody B1-23 without adjuvant immunization
  vehicle group with adjuvant immunization
  group treated with anti hGDF-15 antibody B1-23 with adjuvant immunization Tumor size was measured 3 times per week by caliper-based measurement of tumor length and width.

Mice were sacrificed once their tumor volume exceeded 2,000 mm³ as calculated by the formula V=length×width²/2. Likewise, mice were sacrificed when their condition was found to deteriorate beyond the limits commonly accepted for animal welfare (weight loss≥15%, loss of mobility, prostrate behavior, bad condition of fur).

Figure 11:
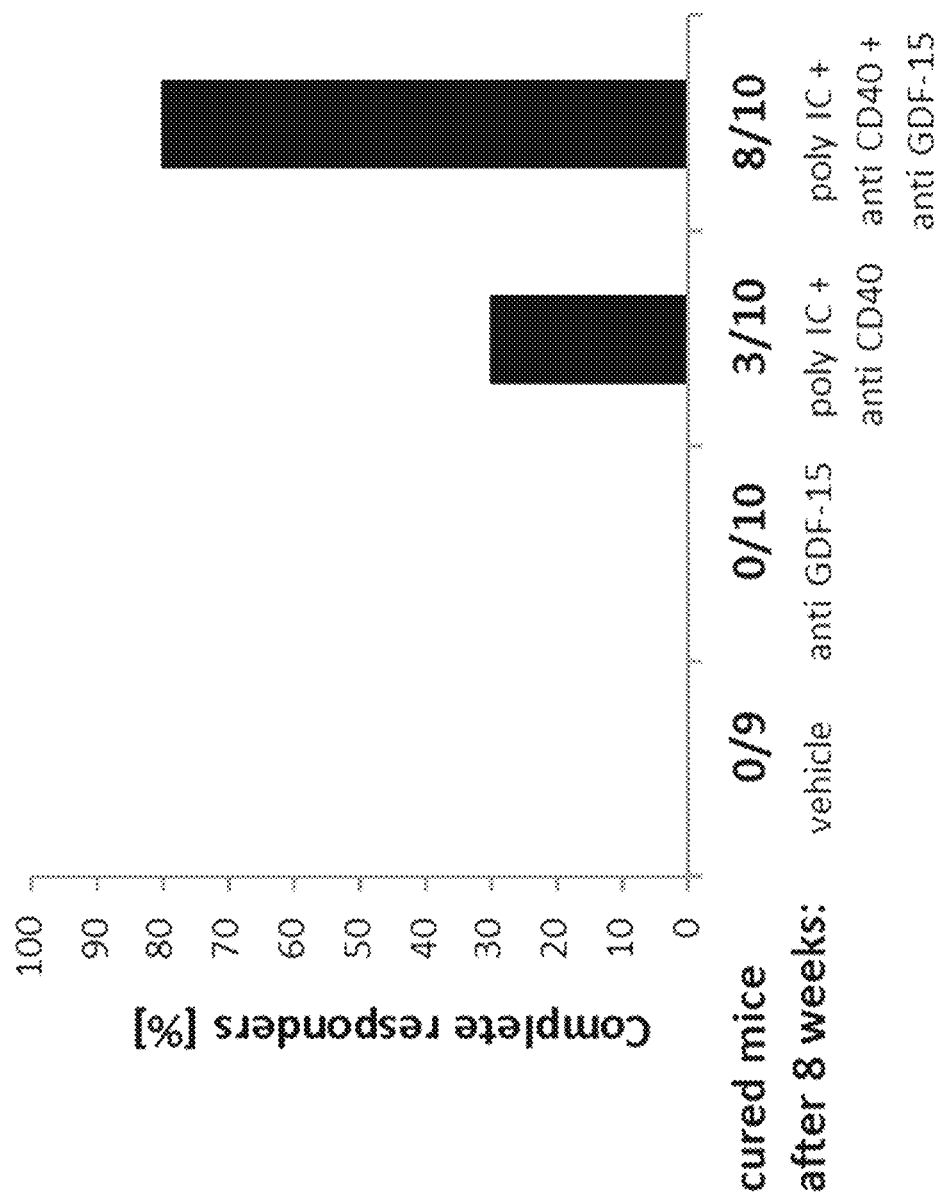
FIG. 11: C57BL/6J mice were subcutaneously inoculated with $2 \times 10^5$ colon MC38$^{tghGDF-15}$ cells. Treatment with anti GDF-15 antibody (20 mg/kg of body weight) was initiated on day 0 and repeated on days 3, 7, 10, 14, 17, and 21. On day 13, animals bearing similarly sized tumors (100-150 mm$^3$) were either treated or not with Poly-ICLC (also abbreviated as "Poly-IC") and anti CD40 antibody. Mice rejecting the pre-established tumor were followed for 57 days. Tumor-bearing mice were sacrificed according to the criteria for animal welfare.

For the surviving mice, the presence of tumors was determined by physical examination until day 57 past tumor inoculation. The results are shown in FIG. 11.

In a previous study performed by the inventors, it had been shown that a treatment with an anti-GDF-15 antibody alone can be advantageously used to treat cancer but did not completely eradicate the tumors, i.e. did not cure the cancer. Similarly, in FIG. 11, neither the vehicle-treated mice nor the mice which were treated with anti-hGDF-15 alone were cured. The treatment with the adjuvant (i.e. with poly ICLC and the anti-CD40 antibody) cured 3 out of 10 mice. Notably, when the treatment with the adjuvant was combined with the treatment with the anti-hGDF-15 antibody, 8 out of 10 mice were cured. Thus, the treatment with the anti-hGDF-15 antibody strong synergized with the treatment with the adjuvant.

Conclusions:

The results obtained in this model system further confirm that hGDF-15 inhibitors synergize with cancer immunotherapy, and in particular with cancer immunotherapy that requires the activation of immune cells such as CD8⁺ T-cells which then exert the cytotoxic activity in the tumor tissue. The results also further confirm that the increase in the percentage of CD8⁺ T-cells in the cancer, which is caused by the uses of hGDF-15 inhibitors according to the invention, can advantageously be used in cancer therapy.

Under the chosen experimental conditions the murine immune model system has very little time to build-up an antigen-specific CD8⁺ T cell response to a fast-growing cancer. Thus, an adjuvant was used to further support the spontaneous immune response in the murine system. In contrast, in human patients, where cancers develop over a longer period of time (e.g. several years), antigen-specific T cells directed against cancer antigens are typically already present at diagnosis, i.e. priming of an immune response usually occurs even before the cancer is diagnosed. These cancer antigen-specific CD8⁺ T cells already exist in humans but to a much lesser extent in the murine model system. Therefore, according to the invention, the uses of hGDF-15 inhibitors according to the invention will be even more effective in humans than in the present murine model system. Accordingly, hGDF-15 inhibitors can effectively be used for the treatment of human cancer patients according to the invention, e.g. to increase in the percentage of CD8⁺ T-cells in a solid cancer, and they will synergize with other cancer immune therapies in humans, and in particular with cancer immune therapies which require CD8⁺ T-cells in the cancer, including cancer immunotherapies with immune checkpoint blockers such as anti-PD-1 and anti-PD-L1 antibodies.

Example 5: GDF-15 Serum Levels Define Survival of Melanoma Patients Treated with Anti PD-1

The study in this Example was performed in order to further validate the results obtained in the study of Example 1, e.g. the finding that hGDF-15 influences the patients' response to immune checkpoint blockers, by an additional independent study.

The following terms were used in connection with this study:
  "Censored"=The patient was removed from the study cohort when no further follow-up data were available.
  "Event"=The patient had died.
  "Survival"=The patient was alive at follow-up.

Patients from the Department of Dermatology, University of Tubingen, Germany, with histologically confirmed melanoma were identified in the Central Malignant Melanoma Registry (CMMR) database which prospectively records patients from more than 60 dermatological centers in Germany. 99 patients, with (a) archived serum samples, (b) available follow-up data, (c) history or presence of loco regional or distant metastasis at the time point of blood draw and (d) experimental treatment with anti PD-1 antibody were selected. The aims and methods of data collection by the CMMR have previously been published in detail (Lasithiotakis, K G et al., Cancer/107/1331-9. 2006). Data obtained for each patient included age, gender, the date of the last follow-up, and the date and cause of death, if applicable. All patients had given written informed consent to have clinical data recorded by the CMMR registry. The institutional ethics committee Tubingen has approved the study (ethic vote 125/2015BO2). Eligible patients were aged 18 years or older and had histologically or cytologically confirmed unresectable stage III or stage IV melanoma not amenable to local therapy and showed disease progression despite having received prior therapies according to the current guidelines. Patients with BRAFV600 mutant tumors had received the recommended first-line or an experimental treatment including BRAF or MEK inhibitor therapy or both. Prior treatment with ipilimumab, if applicable, was considered to have failed when patients had received a minimum of two doses, 3 mg/kg once every 3 weeks, but showed confirmed disease progression within 24 weeks of the last ipilimumab dose. Before administration of anti PD-1, resolution or improvement of ipilimumab-related adverse events to grade 0-1 and prednisone dose 10 mg/day or less was demanded for at least 2 weeks before the first dose of study drug. Eligible patients had Eastern Cooperative Oncology Group (ECOG) performance status 0 or 1; measurable disease per Response Evaluation Criteria in Solid Tumors, version 1.1 (RECIST v1.1); and values within the prespecified range for absolute neutrophil count (≥1500 cells per mL), platelets (≥100 000 cells per mL), haemoglobin (≥90 g/L), serum creatinine (≤−1·5 upper limit of normal [ULN]), serum total bilirubin (≤1·5 ULN or direct bilirubin ULN for patients with total bilirubin concentrations >1·5 ULN), aspartate and alanine aminotransferases (≤2·5 ULN or ≤5 ULN for patients with liver metastases), international normalised ratio or prothrombin time (≤−1·5 ULN if not using anticoagulants), and activated partial thromboplastin time (≤−1·5 ULN if not using anticoagulants). Patients had a washout period of at least 4 weeks between the last dose of the most recent therapy and the first dose of pembrolizumab or nivolumab.

Analysis of hGDF-15 Serum Levels by Enzyme-Linked Immunosorbent Assay (ELISA):

Human GDF-15 serum levels were measured by Enzyme-Linked Immunosorbent Assay (ELISA).

Buffers and Reagents:
Buffered blocking solution: 1% BSA (fraction V pH 7.0, PM, Pasching, Austria) in PBS
Wash solution: PBS-Tween (0.05%)
Standard: human GDF-15 (stock concentration 120 µg/ml, from R&D Systems)
Capture antibody: Human GDF-15 MAb (Clone 147627) from R&D Systems, Mouse IgG2B (catalog #MAB957, from R&D Systems, stock concentration 360 µg/ml)
Detection antibody: Human GDF-15 Biotinylated Affinity Purified PAb, Goat IgG (catalog #BAF940, from R&D Systems, stock concentration 9 µl/ml)
Streptavidin-HRP (Catalog #DY998, from R&D Systems)
Substrate solution: 10 ml 0.1 M NaOAc pH6.0+100 µl TMB+2 µl $H_2O_2$
Stop solution: 1 M $H_2SO_4$ Analysis Procedure:
1. Plate Preparation:
   e. The capture antibody was diluted to the working concentration of 2 µg/ml in PBS. A 96-well microplate (Nunc Maxisorp®) was immediately coated with 50 µl per well of the diluted capture antibody excluding the outer rows (A and H). Rows A and H were filled with buffer to prevent evaporation of the samples during the experiment. The plate was gently tapped to ensure that the bottom of each well was thoroughly covered. The plate was placed in a humid chamber and incubated overnight at room temperature (RT).
   f. Each well was aspirated and washed three times with PBS-Tween (0.05%).
   g. 150 µl of blocking solution was added to each well, followed by incubation at RT for 1 hour.
   h. Each well was aspirated and washed three times with PBS-Tween (0.05%).
2. Assay Procedure:
   d. Standards were prepared. GDF-15 was diluted in buffered blocking solution to a final concentration of 1 ng/ml (4.17 µl GDF+496 µl buffered blocking solution). 1:2 serial dilutions were made.
   e. Duplicate samples 1:20 (6 µl+114 µl buffered blocking solution) were prepared.
   f. 50 µl of diluted samples or standards were added per well, followed by incubation for 1 hour at RT.

|   | 1   | 2   | 3   | 4  | 5  | 6    | 7 | 8   | 9    | 10 | 11 | 12  |
|---|-----|-----|-----|----|----|------|---|-----|------|----|----|-----|
| A | 0   | 0   | 0   | 0  | 0  | 0    | 0 | 0   | 0    | 0  | 0  | 0   |
| B | s1  | s2  | ... |    |    |      |   |     |      |    |    | s12 |
| C | s1  | s2  | ... |    |    |      |   |     |      |    |    | s12 |
| D | s13 | s14 | ... |    |    |      |   |     |      |    |    | s24 |
| E | s13 | s14 | ... |    |    |      |   |     |      |    |    | s24 |
| F | St  | and | ard |    |    |      |   |     | dil  | uti | on | s   |
| G |     |     |     |    | se | rial |   |     |      |    |    |     |
| H | 0   | 0   | 0   | 0  | 0  | 0    | 0 | 0   | 0    | 0  | 0  | 0   | i. Each well was aspirated and washed three times with PBS-Tween (0.05%).
   j. The detection antibody was diluted to a final concentration of 50 ng/ml (56 µl+10 ml blocking buffer). 50 µl of the diluted detection antibody was added to each well, followed by incubation for 1 hour at RT.
   k. Each well was aspirated and washed three times with PBS-Tween (0.05%).
   l. Streptavidin-HRP was diluted 1:200 (50 µl+10 ml blocking buffer). 50 µL of the working dilution of Streptavidin-HRP was added to each well, followed by incubation for 20 min at RT.
   m. Each well was aspirated and washed three times with PBS-Tween (0.05%).
   n. The substrate solution was prepared. 50 µL of substrate solution was added to each well, followed by incubation for 20 min at RT.
   o. 50 µL of stop solution was added to each well.
   p. The optical density of each well was determined immediately, using a microplate reader set to 450 nm.
3. Calculation of GDF-15 Serum Titer:
   d. Each sample/GDF-15 standard dilution was applied in duplicate. To determine GDF-15 titer, the average of the duplicates was calculated and the background (sample without GDF-15) subtracted.
   e. To create a standard curve, values from the linear range were plotted on an X-Y-diagram (X axis: GDF-15 concentration, Y axis: OD450), and a linear curve fit was applied. GDF-15 serum titer of the test samples was calculated by interpolating from the OD450 values of the standard dilutions with known concentration.
   f. To calculate the final GDF-15 concentration of the samples, the distinct dilution factor was considered. Samples yielding OD values below or above the standard range were re-analyzed at appropriate dilutions.

Comparison of hGDF-15 Serum Levels with Patient Data:
Next, the measured hGDF-15 serum levels were compared with patient response data obtained from the study.

Statistical Correlation of hGDF-15 Serum Levels with Patient Data:

Data:

The data analysis was based on a data file containing data from samples from 99 patients containing the columns (variables) Sample designation, GDF-15 (ng/ml), days (to death or censoring), and Ongoing (an index variable for ongoing life).

Outcome Variables (Endpoints):
a. Overall survival (time to death). This endpoint is composed of the event indicator for death (1=dead/ 0=alive), which was derived from the data file, and the time to death or censoring (last time the patient was known to be alive), corresponding to the variable "days".

Response to treatment, e.g. whether a patient was a responder or not (coded as 1=r)

Figure 12:
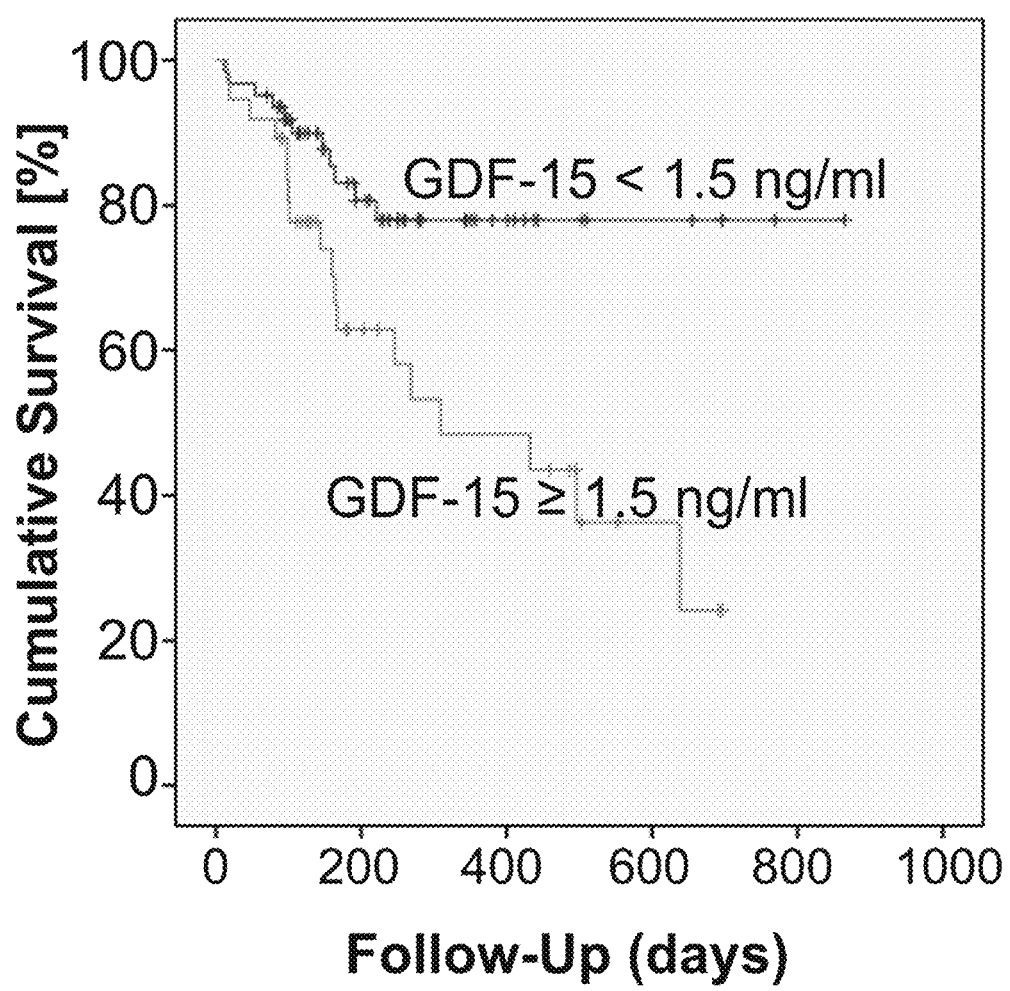
FIG. 12: Cumulative survival in patient groups having GDF-15 levels of <1.5 ng/ml and ≥1.5 ng/ml, respectively.
Figure 13:
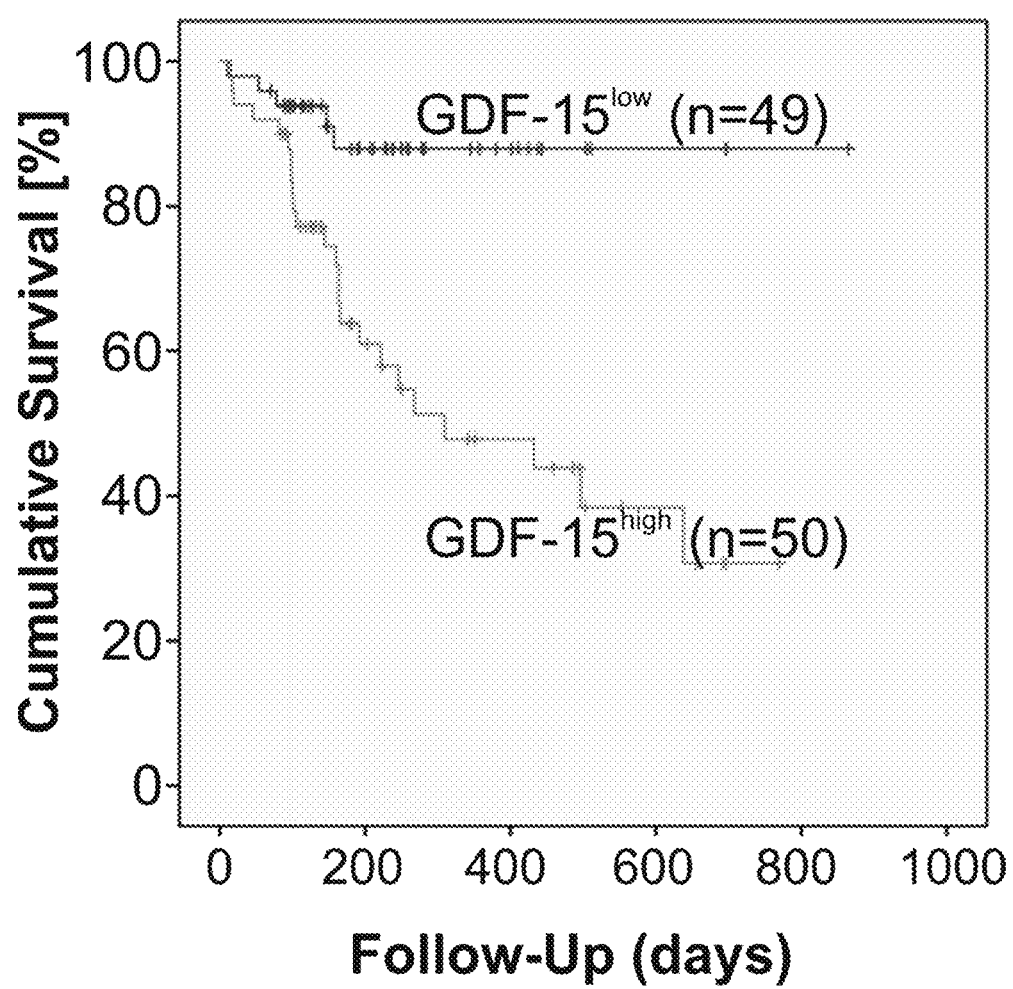
FIG. 13: Cumulative survival in patient groups having high GDF-15 levels (i.e. the 50 patients with the highest GDF-15 levels) and low GDF-15 levels (i.e. the 49 patients with the lowest GDF-15 levels), respectively (median split of the total study cohort).

Data Analysis:

Follow-up time for survival analysis was defined from the date of blood sampling to the last follow-up (i.e. the last information obtained from the patient) or death. All blood samples were taken within days prior to the treatment with the anti-PD1 antibody. For the analysis of OS, patients who were alive at the last follow-up were censored while patients who had died were considered an "event". Cumulative survival probabilities according to Kaplan-Meier were calculated together with 95% confidence intervals (CIs) and compared using two-sided log-rank test statistics. p-values for overall survival were calculated by two-sided log rank statistics. One model was fitted with a grouping variable based on GDF-15 as categorical predictor (groups were: <1.5 ng/ml (n=62), ≥1.5 ng/ml (n=37) or GDF-15$^{low}$ (n=49), GDF-15$^{high}$ (n=50), based on a median split). The resulting Kaplan-Meier curves are shown in FIGS. 12 and 13 where censoring is indicated by vertical lines. Additionally, the following tables contain a summary of the cases (Table 9), patient survival data for patient groups having GDF-15 levels of <1.5 ng/ml and ≥1.5 ng/ml (Tables 10 and 11) and total statistical comparisons of the patient groups having GDF-15 levels of <1.5 ng/ml and ≥1.5 ng/ml (Table 12).

TABLE 9

Summary of Cases

| | Number | Number of events | Censored H* | % Survival |
|---|---|---|---|---|
| GDF-15 < 1.5 ng/ml | 62 | 11 | 51 | 82.3% |
| GDF-15 ≥ 1..5 ng/ml | 37 | 18 | 19 | 51.4% |
| Total | 99 | 29 | 70 | 70.7% |

*H = event-free

TABLE 10

Mean and Median for Survival (number of days of survival)

| | Mean | | | | Median | |
|---|---|---|---|---|---|---|
| | Estimate | Standard error | 95%-Confidence interval lower limit | 95%-Confidence interval upper limit | Estimate | Standard error |
| <1.5 ng/ml | 701.928 | 44.172 | 615.350 | 788.506 | n/d. | n/d. |

TABLE 10-continued

Mean and Median for Survival (number of days of survival)

| | Mean | | | | Median | |
|---|---|---|---|---|---|---|
| | Estimate | Standard error | 95%-Confidence interval lower limit | 95%-Confidence interval upper limit | Estimate | Standard error |
| ≥1.5 ng/ml | 381.683 | 48.882 | 285.875 | 477.491 | 309.000 | 127.570 |
| Total | 569.056 | 44.477 | 481.882 | 656.231 | n/d. | n/d. |

$^a$After censoring the estimate is limited to the longest known survival.
n/d: No median survival data could be calculated due to the presence of >50% survivors in the group.

TABLE 11

Mean and Median for Duration of Survival (number of days of survival)

| | Median$^a$ 95%-confidence interval | |
|---|---|---|
| | lower limit | upper limit |
| <1.5 ng/ml | n/d. | n/d. |
| ≥1.5 ng/ml | 58.963 | 559.037 |
| Total | n/d. | n/d. |

$^a$After censoring the estimate is limited to the longest known survival.
n/d: No median survival data could be calculated due to the presence of >50% survivors in the group.

TABLE 12

Total comparisons

| | Chi-square | df* | Significance |
|---|---|---|---|
| Log Rank (Mantel-Cox) | 8.129 | 1 | .004 |

*df = degrees of freedom
Test on equal distribution of survival for different levels of GDF-15 (<1.5 ng/ml, ≥1.5 ng/ml)

Results and Conclusions:

The above statistical results of this Example further confirmed the results of Example 1. For instance, it was confirmed that the likelihood of a response to the treatment, as indicated by the survival of the patients, significantly decreases with increasing hGDF-15 levels in the patient sera. For example, Table 12 shows that the survival between the two patient groups having GDF-15 levels of <1.5 ng/ml and ≥1.5 ng/ml, respectively, was significantly different, as evidenced by a significance level of 0.004. Similarly, Table 9 demonstrates that a higher percentage of patients (82.3%) survived in the group having GDF-15 levels of <1.5 ng/ml, and Tables 10 and 11 and FIGS. 12 and 13 demonstrate that for patients having GDF-15 levels of <1.5 ng/ml, survival times were remarkably longer than in patients having GDF-15 levels of ≥1.5 ng/ml.

Thus, the results of this Example further confirm that hGDF-15 acts to negatively affect the patients' responses to the treatment with immune checkpoint blockers. Thus, according to the invention, an inhibitor of hGDF-15 will be useful to inhibit the negative effects of hGDF-15 on the patients' responses to the treatment with immune checkpoint blockers, and to improve the patients' responses to the treatment with immune checkpoint blockers not only in melanoma, but in all of the solid cancers referred to herein.

Example 6: In Human Non-Small Cell Lung Cancer (NSCLC) Patients Treated with an Anti-PD1 Antibody, Median hGDF-15 Serum Levels in Patients with Progressive Disease are Higher than in Patients Showing a Partial Response This Example was performed in order to further validate the results obtained in the study of Example 1, e.g. the finding that hGDF-15 influences the patients' response to immune checkpoint blockers, in an additional independent study in a different solid cancer.

Patients:

NSCLC patients were treated with anti-PD1 antibodies in accordance with the approved drug label of the anti-PD1 antibodies. The patients included patients who were pre-treated with other cancer therapies. Due to the fact that a complete response is rarely observed in NSCLC patients, the patient group included patients showing progressive disease and showing a partial response upon PD-1 treatment, but no patients showing a complete response upon PD-1 treatment.

Serum Samples:

Serum samples were taken from the patients prior to the treatment with the anti-PD1 antibodies.

Analysis of hGDF-15 Serum Levels by Enzyme-Linked Immunosorbent Assay (ELISA):

hGDF-15 serum levels in the serum samples were analyzed by Enzyme-Linked Immunosorbent Assay (ELISA), as described in Example 1.

Results:

hGDF-15 serum levels from 5 patients showing a partial response upon treatment with anti-PD-1, and from 5 patients showing progressive disease upon treatment with anti-PD-1, were obtained. Notably, the median hGDF-15 serum level in the patients showing a partial response was 0.55 ng/ml, whereas the median hGDF-15 serum level in the patients showing progressive disease was 1.56 ng/ml. Thus, the median hGDF-15 serum level in the patients showing a progressive disease was about 2.8-fold higher than in the patients showing a partial response.

Conclusions:

The results of this Example further confirm that hGDF-15 levels negatively correlate with the patients' response to immune checkpoint blockers. The results of this Example also further confirm that hGDF-15 acts to negatively affect the patients' responses to the treatment with immune checkpoint blockers such as PD-1. Thus, according to the invention, an inhibitor of hGDF-15 will be useful to inhibit the negative effects of hGDF-15 on the patients' responses to the treatment with immune checkpoint blockers, and to improve the patients' responses to the treatment with immune checkpoint blockers not only in melanoma, but also in lung cancers such as NSCLC and in all of the other solid cancers referred to herein.

Example 7: hGDF-15 Serum Levels do not Significantly Correlate with the Mutational Burden of the Tumors The mutational burden is a known positive prognostic factor for a response of cancer patients to immune checkpoint blockers. Generally, cancer cells harbor genomic mutations which give rise to cancer cell antigens that are specific to the cancer cells and different from the antigens of non-cancerous cells. A high mutational burden leads to a high number of such cancer cell-specific antigens. In cancers harboring such a high number of cancer cell-specific antigens, the stimulation of the immune response by immune checkpoint blockers is considered to be particularly effective, because more cancer cell-specific antigens are available as target antigens for the immune response.

Figure 14A:
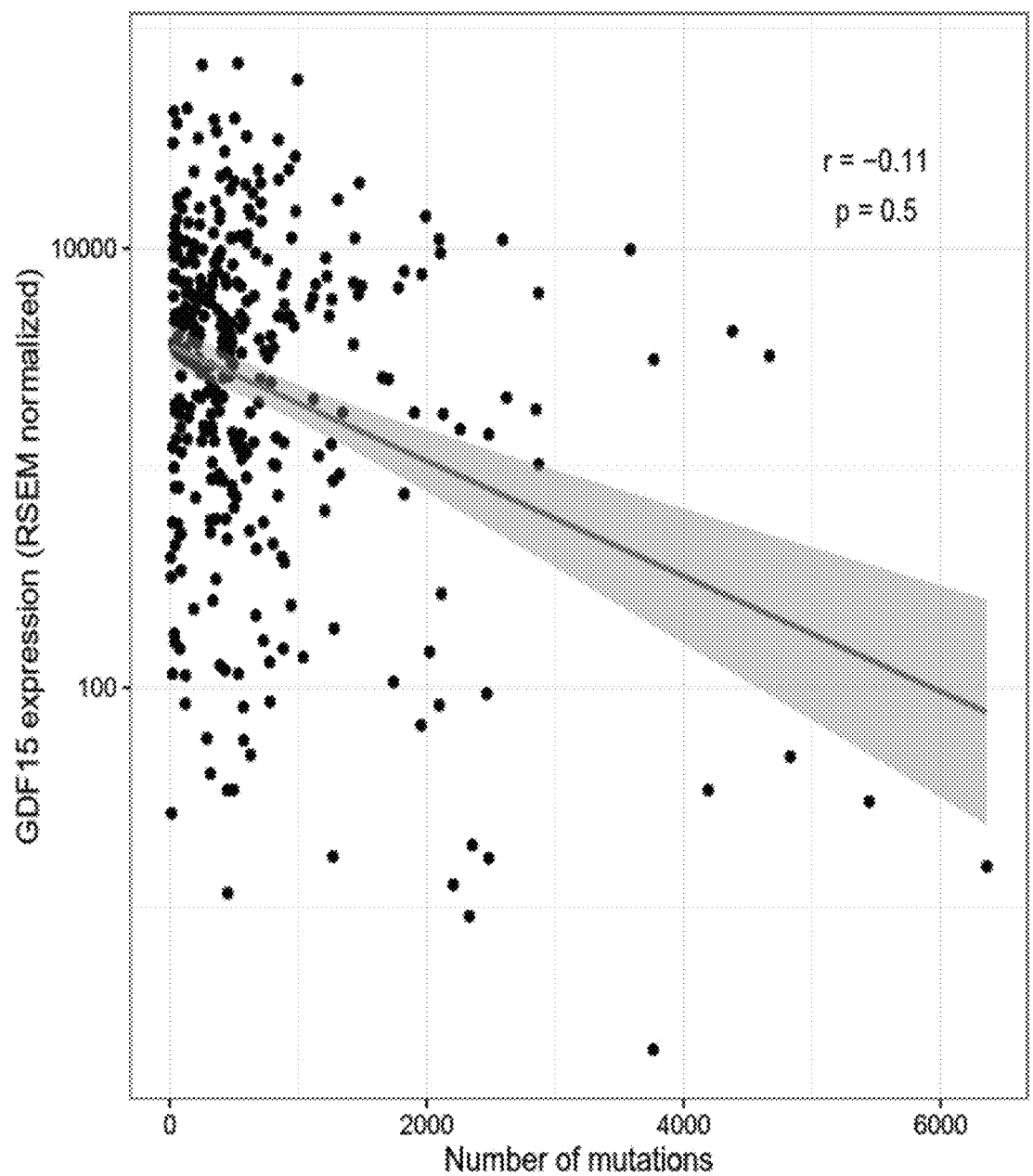
FIGS. 14A-14B: hGDF-15 Serum Levels do not Significantly Correlate with the Mutational Burden of the Tumors.
Figure 14B:
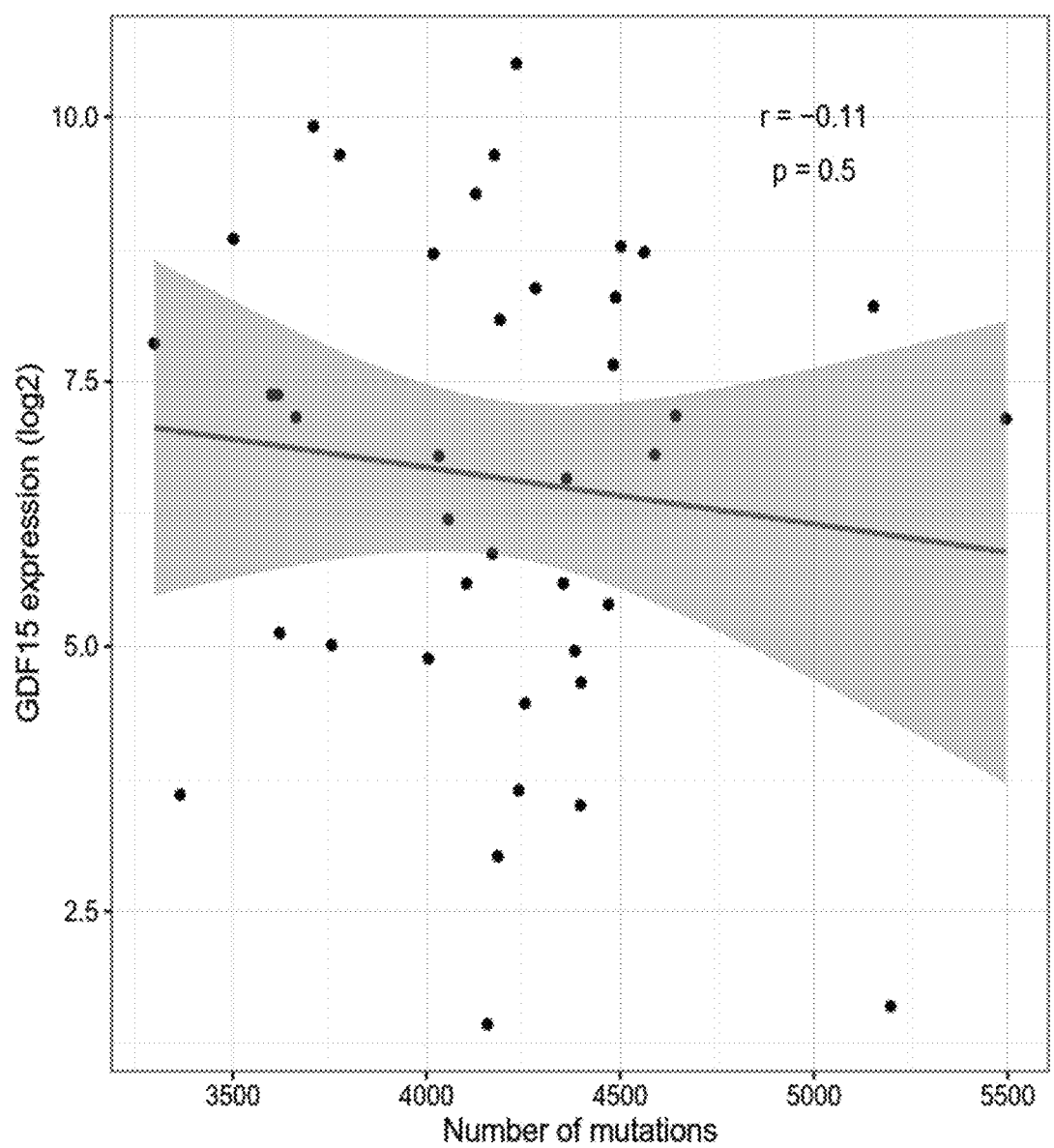

In order to further confirm that hGDF-15 is not merely a surrogate marker for the mutational burden of the tumors, and in order to further confirm that a treatment with hGDF-15 inhibitors acts via a mechanism that is independent from the mutational burden of the tumors, hGDF-15 mRNA levels in cancer samples from cancer patients were plotted against the number of somatic mutations which were identified in the cancers. The somatic mutations were determined by use of exome sequencing. The data were analyzed by using the UZH webtool from the University Hospital Zurich (Cheng P F et al.: Data mining The Cancer Genome Atlas in the era of precision cancer medicine. Swiss Med Wkly. 2015 Sep. 16; 145:w14183.) The results are shown in FIGS. 14A-14B. FIG. 14A shows a plot for cancer patient data obtained from the Cancer Genome Atlas (TGCA) considering only patients with high-grade malignant melanoma (the Cancer Genome Atlas is described in the reference of Cheng P F et al.: Data mining The Cancer Genome Atlas in the era of precision cancer medicine. Swiss Med Wkly. 2015 Sep. 16; 145: w14183). GDF-15 expression was evaluated by normalization using the RSEM ("RNA Seq by expectation maximization") software package (Li B and Dewey C N: RSEM: accurate transcript quantification from RNA-Seq data with or without a reference genome. BMC Bioinformatics. 2011 Aug. 4; 12:323. doi: 10.1186/1471-2105-12-323). FIG. 14B shows a plot for cancer patient data from 40 additional metastatic malignant melanoma patients from the University Hospital Zurich, which were separately analyzed.

Notably, both FIGS. 14A and 14B show a p value of 0.5, indicating that there is no significant correlation between the mutational burden in the cancers and the levels of hGDF-15. These results further confirm that hGDF-15 is not merely a surrogate marker for the mutational burden of the tumors, and that a treatment with hGDF-15 inhibitors acts via a mechanism that is independent from the mutational burden of the tumors.

Figure 15:
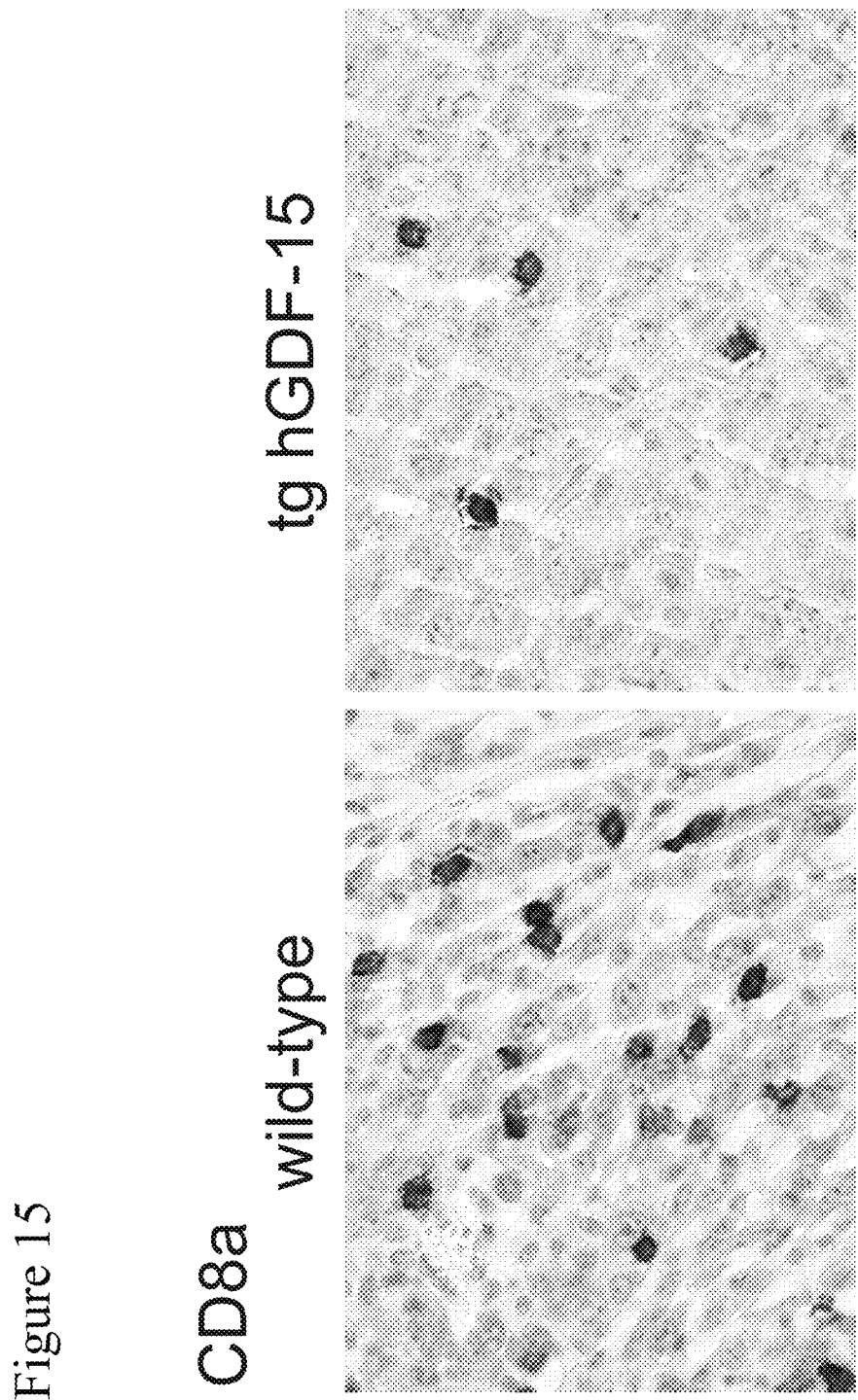
FIG. 15: Immunocytochemistry pictures for CD8a in mice harboring wild-type tumors or tumors overexpressing transgenic (tg) hGDF15 are shown. Tissue sections were stained with anti-CD8a (1:100 dilution; 4SM15 antibody purchased from eBioscience).

Example 8: $CD8^+$ T-Cell Infiltration in Wild-Type Tumors or Human GDF-15 (Over)Expressing Tumors In a pilot study using either wild-type or human GDF-15 (over)expressing MC38 colon cancer cells implanted in the right flank of immunocompetent syngeneic mice C57BL/6, GDF-15 overexpression was associated with reduced immune cell infiltration. Immunocytochemistry pictures for CD8a in mice sacrificed after 29 days harboring wild-type tumors or tumors overexpressing transgenic (tg) hGDF15 are shown in FIG. 15. As can be seen from the Figure, the wild-type tumors contained more CD8a-positive cells than the tumors overexpressing transgenic (tg) hGDF15.

These results further support the finding that according to the present invention, hGDF-15 decreases the percentage of $CD8^+$ T cells in solid cancers, and that conversely, hGDF-15 inhibitors such as anti-GDF-15 antibodies can be used to increase the percentage of $CD8^+$ T-cells in a solid cancer in a human patient.

INDUSTRIAL APPLICABILITY

The combinations of inhibitors, the compositions and the kits according to the present invention may be industrially manufactured and sold as products for the claimed methods and uses (e.g. for treating a cancer as defined herein), in

REFERENCES

Arbabi Ghahroudi M et al.: "Selection and identification of single domain antibody fragments from camel heavy-chain antibodies." FEBS Lett. 1997 Sep. 15; 414(3):521-6.

Ausubel et al.: "Current Protocols in Molecular Biology." Greene Publishing Associates and Wiley Interscience; New York 1992.

Bauskin A R et al.: "The propeptide mediates formation of stromal stores of PROMIC-1: role in determining prostate cancer outcome." Cancer Res. 2005 Mar. 15; 65(6):2330-6.

Brown D A et al.: "Macrophage inhibitory cytokine 1: a new prognostic marker in prostate cancer." Clin Cancer Res. 2009 Nov. 1; 15(21):6658-64.

Cheng P F et al.: Data mining The Cancer Genome Atlas in the era of precision cancer medicine. Swiss Med Wkly. 2015 Sep. 16; 145:w14183.

Chothia C et al.: Conformations of immunoglobulin hypervariable regions. Nature. 1989 Dec. 21-28; 342(6252): 877-83.

Clackson T et al.: "Making antibody fragments using phage display libraries." Nature. 1991 Aug. 15; 352(6336):624-8.

Mei Cong, Ph.D. et al.: Advertorial: "Novel Bioassay to Assess PD-1/PD-L1 Therapeutic Antibodies in Development for Immunotherapy Bioluminescent Reporter-Based PD-1/PD-L1 Blockade Bioassay." (http://www.genengnews.com/gen-articles/advertorial-novel-bioassay-to-assess-pd-1-pd-l1-therapeutic-antibodies-in-development-for-immun/5511/).

Cully M: "Combinations with checkpoint inhibitors at wavefront of cancer immunotherapy." Nat Rev Drug Discov. 2015 June; 14(6):374-5.

Eisenhauer et al.: New response evaluation criteria in solid tumours: revised RECIST guideline (version 1.1). Eur. J. Cancer. 45, No. 2, January 2009, pp 228-47.

Giudicelli V et al.: IMGTN-QUEST, an integrated software program for immunoglobulin and T cell receptor V-J and V-D-J rearrangement analysis. Nucleic Acids Res. 2004 Jul. 1; 32(Web Server issue):W435-40.

Gouttefangeas C et al.: "Flow Cytometry in Cancer Immunotherapy: Applications, Quality Assurance and Future." (2015) In: Cancer Immunology: Translational Medicine from Bench to Bedside (N. Rezaei editor). Springer. Chapter 25: pages 471-486; and the methods according to Harlow and Lane: "Antibodies: A Laboratory Manual" Cold Spring Harbor Laboratory Press, Cold Spring Harbor, N.Y. 1988.

Holliger P et al.: ""Diabodies": small bivalent and bispecific antibody fragments." Proc Natl Acad Sci USA. 1993 Jul. 15; 90(14):6444-8.

Holt L J et al.: "Domain antibodies: proteins for therapy." Trends Biotechnol. 2003 November; 21(11):484-90.

Huang C Y et al.: "Molecular alterations in prostate carcinomas that associate with in vivo exposure to chemotherapy: identification of a cytoprotective mechanism involving growth differentiation factor 15." Clin Cancer Res. 2007 Oct. 1; 13(19):5825-33.

Jackson and Linsley: "Recognizing and avoiding siRNA off-target effects for target identification and therapeutic application." Nat Rev Drug Discov. 2010 January; 9(1): 57-67.

Johnen H et al.: "Tumor-induced anorexia and weight loss are mediated by the TGF-beta superfamily cytokine MIC-1." Nat Med. 2007 November; 13(11):1333-40.

Jones P T et al.: "Replacing the complementarity-determining regions in a human antibody with those from a mouse." Nature. 1986 May 29-Jun. 4; 321(6069):522-5.

Kabat et al.: Sequences of proteins of immunological interest, U.S. Dept. of Health and Human Services, Public Health Service, National Institutes of Health, Bethesda, Md. 1983.

Kanasty R et al., "Delivery materials for siRNA therapeutics.", Nat Mater. 2013 November; 12(11):967-77.

Knoepfel S A et al., "Selection of RNAi-based inhibitors for anti-HIV gene therapy." World J Virol. 2012 Jun. 12; 1(3):79-90.

Köhler G and Milstein C: "Continuous cultures of fused cells secreting antibody of predefined specificity." Nature. 1975 Aug. 7; 256(5517):495-7.

Lasithiotakis, K G et al., Cancer/107/1331-9. 2006.

Li B and Dewey C N: RSEM: accurate transcript quantification from RNA-Seq data with or without a reference genome. BMC Bioinformatics. 2011 Aug. 4; 12:323. doi: 10.1186/1471-2105-12-323.

Marks J D et al.: "By-passing immunization. Human antibodies from V-gene libraries displayed on phage." J Mol Biol. 1991 Dec. 5; 222(3):581-97.

Mimeault M and Batra S K: "Divergent molecular mechanisms underlying the pleiotropic functions of macrophage inhibitory cytokine-1 in cancer." J Cell Physiol. 2010 September; 224(3):626-35.

Paul, W. E. (Ed.).: "Fundamental Immunology" 2nd Ed. Raven Press, Ltd., New York 1989.

Remington's Pharmaceutical Sciences, Ed. A R Gennaro, 20th edition, 2000, Williams & Wilkins, P A, USA.

R Core Team (2014). R: A language and environment for statistical computing. R Foundation for Statistical Computing, Vienna, Austria. URL http://www.R-project.org/.

Riechmann L et al.: "Reshaping human antibodies for therapy." Nature. 1988 Mar. 24; 332(6162):323-7.

C. Robert et al. N Engl J Med 2015; 372:2521-2532.

Roth P et al.: "GDF-15 contributes to proliferation and immune escape of malignant gliomas." Clin Cancer Res. 2010 Aug. 1; 16(15):3851-9.

Saerens D et al.: "Single-domain antibodies as building blocks for novel therapeutics." Curr Opin Pharmacol. 2008 October; 8(5):600-8. Epub 2008 Aug. 22.

Sambrook et al.: "Molecular Cloning: A Laboratory Manual.", 2nd Ed., Cold Spring Harbor Laboratory Press, Cold Spring Harbor, N.Y. 1989.

Siegel D L: "Recombinant monoclonal antibody technology." Transfus Clin Biol. 2002 January; 9(1):15-22.

Stefanescu R. et al., Eur. J. Mass Spectrom. 13, 69-75 (2007)

Suckau et al. Proc Natl Acad Sci USA. 1990 December; 87(24): 9848-9852.

Tumeh et al., PD-1 blockade induces responses by inhibiting adaptive immune resistance. Nature. 2014 Nov. 27; 515 (7528):568-71.

Van der Burg S H, et al.: "Immunoguiding, the final frontier in the immunotherapy of cancer." (2014) In Cancer Immunotherapy meets oncology (C M Britten, S Kreiter, M. Diken & H G Rammensee eds). Springer International Publishing Switzerland p37-51 ISBN: 978-3-319-05103-1.

Weinberg R. et al.: The Biology of Cancer. Garland Science: New York 2006. 850p.

Yadav M et al.: Predicting immunogenic tumour mutations by combining mass spectrometry and exome sequencing. Nature. 2014 Nov. 27; 515(7528):572-6.

Zhang, J., Yao, Y.-H., Li, B.-G., Yang, Q., Zhang, P.-Y., and Wang, H.-T. (2015). Prognostic value of pretreatment serum lactate dehydrogenase level in patients with solid tumors: a systematic review and meta-analysis. Scientific Reports 5, 9800

Zhou et al. Growth differentiation factor-15 suppresses maturation and function of dendritic cells and inhibits tumor-specific immune response. PLoS One. 2013 Nov. 13; 8(11):e78618.

WO 2005/099746
WO 2009/021293
WO 2014/049087
PCT/EP2015/056654
WO 2014/100689

The invention claimed is:

1. A method of increasing the percentage of CD8+ T-cells in a melanoma in a patient in need thereof, the method comprising administering to the patient a combination of:
a human growth and differentiation factor 15 (hGDF-15) inhibitor, wherein the hGDF-15 inhibitor is a monoclonal antibody capable of binding to hGDF-15, or an antigen-binding portion thereof; and
and an immune checkpoint blocker selected from the group consisting of an anti-PD-1 antibody and an anti-PD-L1 antibody.

2. The method of claim 1, wherein the level of hGDF-15 in a blood sample obtained from the patient before treatment is at least 1.2 ng/ml, 1.5 ng/ml, or 1.8 ng/ml.

3. The method of claim 1, wherein the melanoma is stage III or stage IV melanoma.

4. The method of claim 3, wherein the melanoma is unresectable stage III melanoma or stage IV melanoma not amenable to local therapy.

5. The method of claim 1, wherein:
(i) the antibody or antigen-binding portion thereof binds to a conformational or discontinuous epitope on hGDF-15, comprised by the amino acid sequences of SEQ ID No: 25 and SEQ ID No: 26, and/or
(ii) the antibody or antigen-binding portion thereof comprises a heavy chain variable domain which comprises a CDR1 region comprising the amino acid sequence of SEQ ID NO: 3, a CDR2 region comprising the amino acid sequence of SEQ ID NO: 4 and a CDR3 region comprising the amino acid sequence of SEQ ID NO: 5, and wherein the antibody or antigen-binding portion thereof comprises a light chain variable domain which comprises a CDR1 region comprising the amino acid sequence of SEQ ID NO: 6, a CDR2 region comprising the amino acid sequence ser-ala-ser and a CDR3 region comprising the amino acid sequence of SEQ ID NO: 7.

6. The method of claim 1, wherein the immune checkpoint blocker is selected from the group consisting of nivolumab, pembrolizumab, pidilizumab, AMP-22, and BMS-936559.

7. The method of claim 1, further comprising administering to the patient polyinosinic:polycytidylic acid.

8. The method of claim 1, further comprising administering to the patient an anti-CD40 antibody.

9. The method of claim 1, wherein the hGDF-15 inhibitor increases the percentage of CD8+T-cells in the melanoma by increasing the adhesion of CD8+T-cells to endothelial cells and thereby increasing entry of the CD8+T-cells from the blood stream into the melanoma.

10. A method of treating a melanoma in a patient in need thereof, the method comprising administering to the patient a combination of:
a human growth and differentiation factor 15 (hGDF-15) inhibitor, wherein the hGDF-15 inhibitor is a monoclonal antibody capable of binding to hGDF-15, or an antigen-binding portion thereof; and
and an immune checkpoint blocker selected from the group consisting of an anti-PD-1 antibody and an anti-PD-L1 antibody.

11. The method of claim 10, wherein the level of hGDF-15 in a blood sample obtained from the patient before treatment is at least 1.2 ng/ml, 1.5 ng/ml, or 1.8 ng/ml.

12. The method of claim 10, wherein the melanoma is stage III or stage IV melanoma.

13. The method of claim 12, wherein the melanoma is unresectable stage III melanoma or stage IV melanoma not amenable to local therapy.

14. The method of claim 10, wherein:
(i) the antibody or antigen-binding portion thereof binds to a conformational or discontinuous epitope on hGDF-15, comprised by the amino acid sequences of SEQ ID No: 25 and SEQ ID No: 26, and/or
(ii) the antibody or antigen-binding portion thereof comprises a heavy chain variable domain which comprises a CDR1 region comprising the amino acid sequence of SEQ ID NO: 3, a CDR2 region comprising the amino acid sequence of SEQ ID NO: 4 and a CDR3 region comprising the amino acid sequence of SEQ ID NO: 5, and wherein the antibody or antigen-binding portion thereof comprises a light chain variable domain which comprises a CDR1 region comprising the amino acid sequence of SEQ ID NO: 6, a CDR2 region comprising the amino acid sequence ser-ala-ser and a CDR3 region comprising the amino acid sequence of SEQ ID NO: 7.

15. The method of claim 10, wherein the immune checkpoint blocker is selected from the group consisting of nivolumab, pembrolizumab, pidilizumab, AMP-22, and BMS-936559.

16. The method of claim 10, further comprising administering to the patient polyinosinic:polycytidylic acid.

17. The method of claim 10, further comprising administering to the patient an anti-CD40 antibody.

18. The method of claim 10, wherein the hGDF-15 inhibitor increases the percentage of CD8+T-cells in the melanoma by increasing the adhesion of CD8+T-cells to endothelial cells and thereby increasing entry of the CD8+ T-cells from the blood stream into the melanoma.

* * * * *